US007803802B2

(12) United States Patent
Huang et al.

(10) Patent No.: US 7,803,802 B2
(45) Date of Patent: Sep. 28, 2010

(54) SUBSTITUTED AMIDE BETA SECRETASE INHIBITORS

(75) Inventors: Ying Huang, East Brunswick, NJ (US); Guoqing Li, Belle Mead, NJ (US); Andrew W Stamford, Chatham Township, NJ (US)

(73) Assignee: Schering Corporation, Kenilworth, NJ (US)

( * ) Notice: Subject to any disclaimer, the term of this patent is extended or adjusted under 35 U.S.C. 154(b) by 641 days.

(21) Appl. No.: 11/185,419

(22) Filed: Jul. 20, 2005

(65) Prior Publication Data

US 2006/0040994 A1 Feb. 23, 2006

Related U.S. Application Data

(60) Provisional application No. 60/590,102, filed on Jul. 22, 2004.

(51) Int. Cl.
*A61K 31/497* (2006.01)
*C07D 241/02* (2006.01)

(52) U.S. Cl. .................................... 514/252.1; 544/408

(58) Field of Classification Search ....................... None
See application file for complete search history.

(56) References Cited

U.S. PATENT DOCUMENTS

| | | | |
|---|---|---|---|
| 6,683,091 | B2 | 1/2004 | Asberom et al. |
| 2002/0019424 | A1 | 2/2002 | Mutel et al. |
| 2004/0116414 | A1 | 6/2004 | Tung et al. |

FOREIGN PATENT DOCUMENTS

| | | |
|---|---|---|
| EP | 1299349 | 4/2003 |
| WO | WO 89/03842 | 5/1989 |
| WO | WO 00/07995 | 2/2000 |
| WO | WO 00/50391 | 8/2000 |
| WO | WO 02/02505 | 1/2002 |
| WO | WO 02/02506 | 1/2002 |
| WO | WO 02/02512 | 1/2002 |
| WO | WO 02/02518 | 1/2002 |
| WO | WO 02/02520 | 1/2002 |
| WO | WO 02/088101 | 11/2002 |
| WO | WO 03/013527 | 2/2003 |
| WO | WO 03/018543 | 3/2003 |
| WO | WO 03/035613 | 5/2003 |
| WO | WO 03/066592 | 8/2003 |
| WO | WO 2004/004396 | 1/2004 |
| WO | WO 0108391 * | 11/2005 |

OTHER PUBLICATIONS

Dorwald F. A. Side Reactions in Organic Synthesis, 2005, Wiley: VCH, Weinheim p. IX of Preface.*
Vippagunta et. al. Advanced Drug Delivery Reviews 48 (2001) 3-26.*
Borisy, et. al., Proceedings of the National Academy of Sciences of the United States of America, 100(13) 7977-7982.*
Fox, et. al.; Neuropsychiatr. Dis. Treat. Jun. 2006; 2(2): 121-125.*
International Search Report (PCT/US2005/025780) Mail Date Dec. 22, 2005—4 pages.

* cited by examiner

*Primary Examiner*—James O Wilson
*Assistant Examiner*—Jeffrey H Murray
(74) *Attorney, Agent, or Firm*—Keith D. MacMillan; William Lee

(57) ABSTRACT

Disclosed are novel compounds of the formula

I

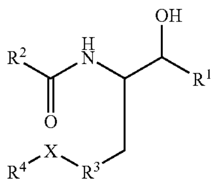

or a pharmaceutically acceptable salt or solvate thereof, wherein $R^1$, $R^2$, $R^3$, $R^4$ and X are as defined in the specification.

Also disclosed are pharmaceutical compositions comprising the compounds of formula I.

Also disclosed are methods of treating cognitive or neurodegenerative diseases such as Alzheimer's disease.

Also disclosed are methods of treating a cognitive or neurodegenerative disease comprising administering to a patient I need of such treatment a combination of at least one compound of formula I and at least one compound selected from the group consisting of β-secretase inhibitors other than those of formula I, HMG-CoA reductase inhibitors, gamma-secretase inhibitors, non-steroidal anti-inflammatory agents, N-methyl-D-aspartate receptor antagonists, cholinesterase inhibitors and anti-amyloid antibodies.

19 Claims, No Drawings

SUBSTITUTED AMIDE BETA SECRETASE INHIBITORS

CROSS REFERENCE TO RELATED APPLICATION

This Application claims the benefit of U.S. Provisional Application No. 60/590,102 filed Jul. 22, 2004.

FIELD OF THE INVENTION

This invention relates to substituted amide beta secretase inhibitors, pharmaceutical compositions comprising said compounds, their use in the treatment of cardiovascular diseases, cognitive and neurodegenerative diseases, and their use as inhibitors of the Human Immunodeficiency Virus, plasmepsins, cathepsin D and protozoal enzymes.

BACKGROUND

Alzheimer's disease (AD) is a progressive neurodegenerative disease that is ultimately fatal. Disease progression is associated with gradual loss of cognitive function related to memory, reasoning, orientation and judgment. Behavioral changes including confusion, depression and aggression also manifest as the disease progresses. The cognitive and behavioral dysfunction is believed to result from altered neuronal function and neuronal loss in the hippocampus and cerebral cortex. The currently available AD treatments are palliative, and while they ameliorate the cognitive and behavioral disorders, they do not prevent disease progression. Therefore there is an unmet medical need for AD treatments that halt disease progression.

Pathological hallmarks of AD are the deposition of extracellular β-amyloid (Aβ) plaques and intracellular neurofibrillary tangles comprised of abnormally phosphorylated protein tau. Individuals with AD exhibit characteristic Aβ deposits, in brain regions known to be important for memory and cognition. It is believed that Aβ is the fundamental causative agent of neuronal cell loss and dysfunction which is associated with cognitive and behavioral decline. Amyloid plaques consist predominantly of Aβ peptides comprised of 40-42 amino acid residues, which are derived from processing of amyloid precursor protein (APP). APP is processed by multiple distinct protease activities. Aβ peptides result from the cleavage of APP by β-secretase at the position corresponding to the N-terminus of Aβ, and at the C-terminus by γ-secretase activity. APP is also cleaved by α-secretase activity resulting in the secreted, non-amyloidogenic fragment known as soluble APP.

An aspartyl protease known as BACE-1 has been identified as the β-secretase activity responsible for cleavage of APP at the position corresponding to the N-terminus of Aβ peptides.

Accumulated biochemical and genetic evidence supports a central role of Aβ in the etiology of AD. For example, Aβ has been shown to be toxic to neuronal cells in vitro and when injected into rodent brains. Furthermore inherited forms of early-onset AD are known in which well-defined mutations of APP or the presenilins are present.

Substituted amine BACE-1 inhibitors are disclosed in, WO 04/04396, WO 02/02505, WO 02/02506, WO 02/02512, WP 02/02518 and WO 02/02520. Renin inhibitors comprising a (1-amino-2 hydroxy-2-heterocyclic)ethyl moiety are disclosed in WO 89/03842. WO 02/088101 discloses BACE inhibitors functionally described as being comprised of four hydrophobic moieties, as well as series of compounds preferably comprising a heterocyclic or heteroaryl moiety.

SUMMARY OF THE INVENTION

The present invention relates to compounds having the structural formula I

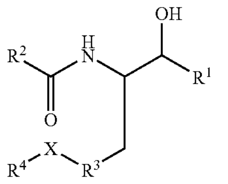

I or a pharmaceutically acceptable salt or solvate thereof, wherein $R^1$ is

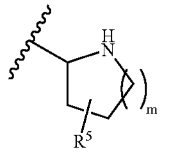

or

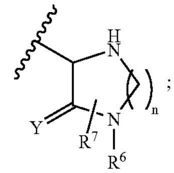

;

$R^2$ is hydrogen, alkyl or cycloalkyl;

$R^3$ is arylene, heteroarylene, heterocyclylene or cycloalkylene;

$R^4$ is hydrogen, —C(O)-alkyl, alkyl, cycloalkyl, cycloalkylalkyl, aryl, aralkyl, alkoxyalkyl, heterocyclyl, heterocyclylalkyl, heteroaralkyl or heteroaryl;

$R^5$ and $R^7$ are 1 to 4 moieties, each moiety being independently selected from hydrogen, —OH, alkyl, cycloalkyl, aryl, heteroaryl, aralkyl, heteroaralkyl, aralkoxy, heteroaralkoxy and alkoxy, with the proviso that when $R^5$ and $R^7$ are —OH, aralkoxy, heteroaralkoxy and alkoxy, $R^5$ and $R^7$ are not attached to a ring carbon adjacent to a ring nitrogen;

$R^6$ is hydrogen, alkyl, cycloalkyl, cycloalkylalkyl, aryl, heteroaryl, aralkyl, heteroaralkyl, heterocyclyl, heterocyclylalkyl, —C(O)$R^8$, —C(O)O$R^{11}$, —S(O)$R^8$, —S($O_2$)$R^8$ or —CN; with the proviso that when Y is =O, $R^6$ cannot be —C(O)$R^8$, —C(O)O$R^{11}$, —S(O)$R^8$, —S($O_2$)$R^8$ or —CN;

$R^8$ is hydrogen, alkyl, cycloalkyl, aryl, heteroaryl, cycloalkylalkyl, aralkyl, heteroaralkyl, heterocyclyl, heterocyclylalkyl, alkenyl, alkynyl or —N($R^9$)($R^{10}$);

$R^9$ and $R^{10}$ are independently selected from the group consisting of hydrogen, alkyl, cycloalkyl, cycloalkylalkyl, aryl, heteroaryl, heterocyclyl, aralkyl, heteroaralkyl, heterocyclylalkyl, alkenyl and alkynyl;

or $R^9$ and $R^{10}$ together with the nitrogen to which they are attached, form a 3-7 membered heterocyclyl ring;

$R^{11}$ is alkyl, cycloalkyl, aryl, heteroaryl, cycloalkylalkyl, aralkyl, heteroaralkyl, heterocyclyl, heterocyclylalkyl, alkenyl or alkynyl;

X is a bond connecting $R^3$ and $R^4$, O—, —S—, alkylene, -alkyleneNH—, -alkyleneNHC(O)—, -alkyleneNHSO$_2$—, —NH—, —NHC(O)—, or —NHSO$_2$—;

Y is =O or (H, H);

m is 0, 1, 2, or 3;

and n is 1, 2, or 3;

wherein each alkyl is optionally substituted with 1 to 3 moieties selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl; and wherein each arylene, heteroarylene, heterocyclylalkyl, heterocyclylene, cycloalkylene, cycloalkyl, cycloalkylalkyl, aryl, heteroaryl, heterocyclyl, aralkyl, heteroaralkyl, aralkoxy or heteroaralkoxy is optionally substituted with 1 to 4 moieties selected from the group consisting of —$CF_3$, alkyl, alkenyl, alkynyl, aryl, heteroaryl, aralkyl, alkylaryl, heteroaralkyl, arylalkenyl, heteroarylalkenyl, arylalkynyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—$NH_2$, —C(=NH)—$NH_2$, —C(=NH)—NH(alkyl), $Y_1Y_2N$—, $Y_1Y_2N$-alkyl-, $Y_1Y_2NC(O)$—, $Y_1Y_2NSO_2$— and —$SO_2NY_1Y_2$, wherein $Y_1$ and $Y_2$ can be the same or different and are independently selected from the group consisting of hydrogen, alkyl, aryl, cycloalkyl, —C(O)alkyl and aralkyl, with the proviso that cycloalkyl, cycloalkylene, heterocyclyl and heterocyclylene can be substituted with =O.

Compounds represented by formula I are beta-secretase inhibitors useful for the prevention and treatment of Alzheimer's disease.

In another aspect, the invention relates to a pharmaceutical composition comprising at least one compound of formula I and a pharmaceutically acceptable carrier.

In another aspect, the invention comprises administering at least one compound of formula I to a patient in need of such treatment.

More specifically, the invention comprises: the method of treating a cardiovascular disease such as hypertension, renal failure, congestive heart failure or another disease modulated by renin inhibition; the method of treating Human Immunodeficiency Virus; the method of treating a cognitive or neurodegenerative disease such as Alzheimer's Disease; the method of inhibiting plasmepsins I and II for treatment of malaria; the method of inhibiting Cathepsin D for the treatment of Alzheimer's Disease, breast cancer, and ovarian cancer; and the method of inhibiting protozoal enzymes, for example inhibition of plasmodium falciparnum, for the treatment of fungal infections. Said method of treatment comprise administering at least one compound of formula I to a patient in need of such treatment. In particular, the invention comprises the method of treating Alzheimer's Disease comprising administering at least one compound of formula I to a patient in need of such treatment.

In another aspect, the invention comprises the method of treating Alzheimer's Disease comprising administering to a patient in need of such treatment a combination of at least one compound of formula I and a cholinesterase inhibitor or a muscarinic $m_1$ agonist or $m_2$ antagonist.

In a final aspect, the invention relates to a kit comprising in separate containers in a single package pharmaceutical compositions for use in combination, in which one container comprises a compound of formula I in a pharmaceutically acceptable carrier and a second container comprises a cholinesterase inhibitor or a muscarinic $m_1$ agonist or $m_2$ antagonist in a pharmaceutically acceptable carrier, the combined quantities being an effective amount to treat a cognitive disease or neurodegenerative disease such as Alzheimer's Disease.

DETAILED DESCRIPTION

Referring to formula I, above, preferred compounds of the invention are those with the following stereochemistry:

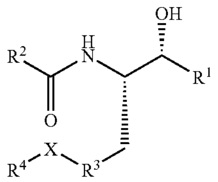

In preferred compounds of formula I, $R^1$ can be

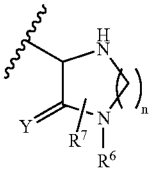

wherein n is 2 and $R^6$ and $R^7$ are defined herein.

$R^2$ is preferably is alkyl, more preferably methyl.

$R^3$ is arylene or halo-substituted arylene, more preferably phenylene or halo-substituted phenylene, specifically a halo-substituted phenylene, where said halo is preferably fluoride.

$R^4$ is hydrogen, —C(O)-alkyl, alkyl, aryl, aralkyl, substituted aryl, substituted aralkyl, alkoxyalkyl, heteroaralkyl, substituted heteroaryl, substituted heteroaralkyl, alkoxyalkyl, heterocyclyl, heterocyclylalkyl, substituted heterocyclyl, substituted heterocyclylalkyl or heteroaryl.

Or in the alternative, $R^4$ is preferably hydrogen, methyl, ethyl, propyl, butyl, pentyl, hexyl, —C(O)Oethyl,

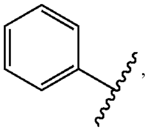 , 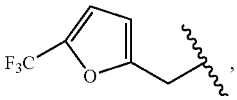 ,

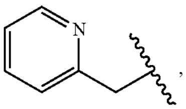 , 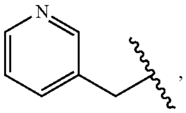 ,

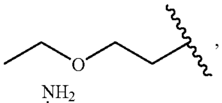 , 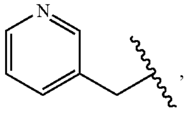 ,

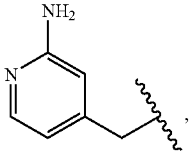 , 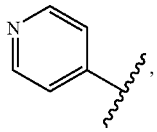 ,

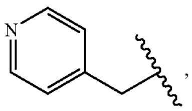 , 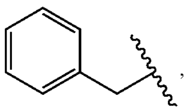 ,

-continued

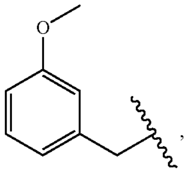, 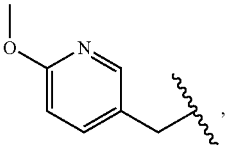,

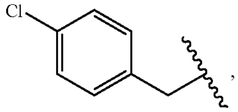, 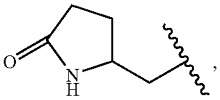,

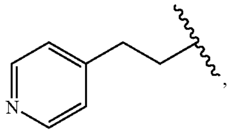, 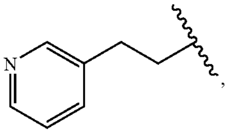,

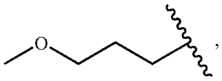, 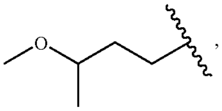,

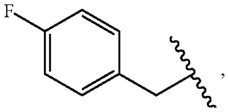, 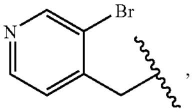,

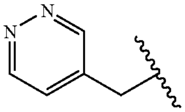, 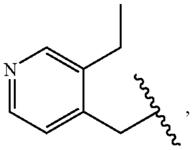,

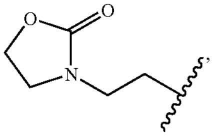, 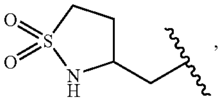,

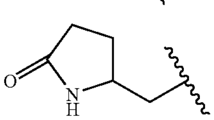, 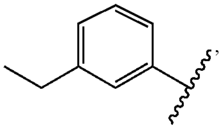,

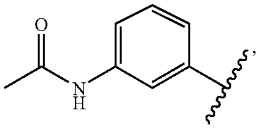, 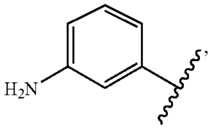,

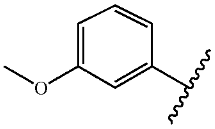 or 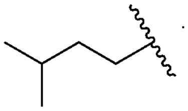.

Preferably, $R^5$ and $R^7$ independently are alkyl substituted by a cycloalkyl group alkyl or substituted by an aryl or heteroaryl group.

In a preferred embodiment of the compounds of formula I, $R^6$ can be aralkyl, preferably

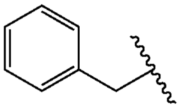.

Or in the alternative $R^6$ is —$S(O)_2$—$R^8$ or more preferably, $R^6$ is

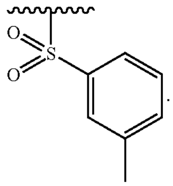.

Preferably X is a bond connecting $R^3$ and $R^4$, O, alkylene, -alkyl-$NHSO_2$— or -alkyl-NHC(O)—; Y is O and n is 2.

In a particular preferred embodiment of the compound of formula I, $R^1$ is

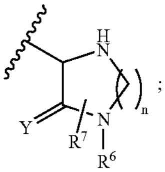;

n is 2;

$R^2$ is alkyl;

$R^3$ is phenylene or halo-substituted phenylene;

$R^4$ is hydrogen, —C(O)-alkyl, alkyl, aryl, aralkyl, substituted aryl, substituted aralkyl, alkoxyalkyl, heteroaralkyl, substituted heteroaryl, substituted heteroaralkyl, alkoxyalkyl, heterocyclyl, heterocyclylalkyl, substituted heterocyclyl, substituted heterocyclylalkyl or heteroaryl;

$R^5$ and $R^7$ are hydrogen, alkyl substituted by a cycloalkyl group, alkyl substituted by an aryl or heteroaryl group;

$R^6$ is aralkyl or —$S(O)_2R^8$;

$R^8$ is

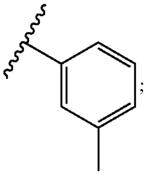;

X is a bond connecting $R^3$ and $R^4$, O, alkylene, -alkyl-$NHSO_2$— or -alkyl-NHC(O)—;

and

Y is O.

In the above-preferred embodiment, $R^2$ is preferably methyl;

$R^3$ preferably is

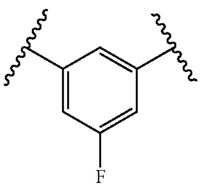 or 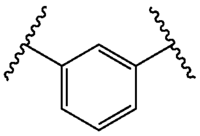;

$R^4$ is preferably hydrogen, methyl, ethyl, propyl, butyl, pentyl, hexyl, —C(O)Oethyl,

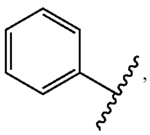, 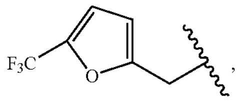, 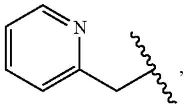, 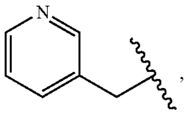, 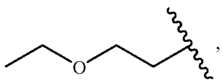, 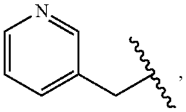, 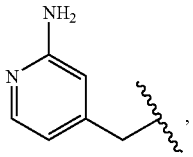, 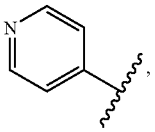, 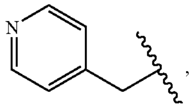, 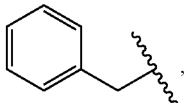, 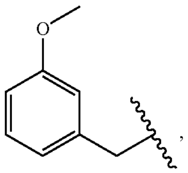, 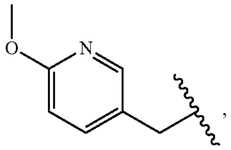, 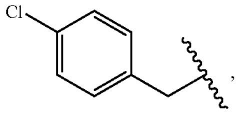, 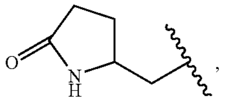, 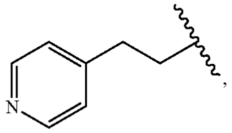, 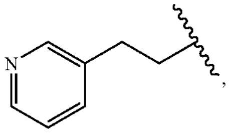, 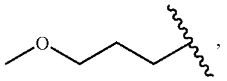, 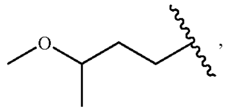, 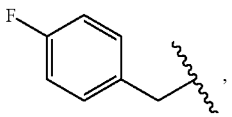, 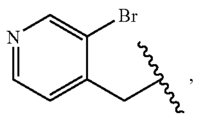, 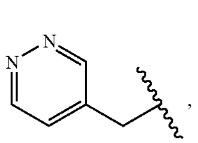, 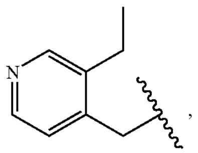, 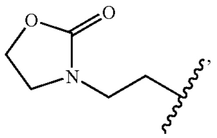, 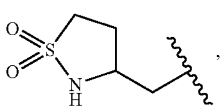, -continued

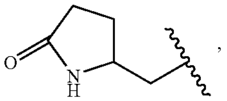, 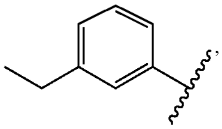, 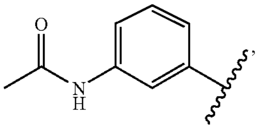, 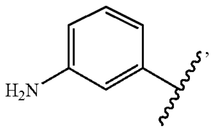, 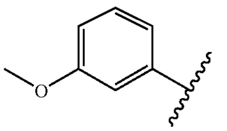 or 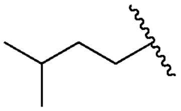.

$R^6$ is preferably

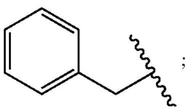;

$R^7$ is preferably hydrogen;

and preferably X is a bond connecting $R^3$ and $R^4$, O, alkylenyl, -alkyl-$NHSO_2$— or -alkyl-NHC(O)—; Y is O and n is 2.

It is noted that the carbons of formula I may be replaced with 1 to 3 silicon atoms so long as all valency requirements are satisfied.

Except where stated otherwise, the following definitions apply throughout the present specification and claims. These definitions apply regardless of whether a term is used by itself or in combination with other terms. Hence the definition of "alkyl" applies to "alkyl" as well as to the "alkyl" portions of "alkoxy", "cycloalkyl" and so forth.

As used above, and throughout the specification, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. Non-limiting examples of suitable alkyl groups include methyl, ethyl, n-propyl, isopropyl, n-butyl, t-butyl, n-pentyl, heptyl, nonyl and decyl. Substituted alkyl groups include but are not limited to fluoromethyl, trifluoromethyl and cyclopropylmethyl.

"Alkylene" means a difunctional group obtained by removal of a hydrogen atom from an alkyl group that is defined above. Non-limiting examples of alkylene include methylene and ethylene.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. The term "substituted alkenyl" means that the alkenyl group may be substituted by one or more substituents which may be the same or different, each substituent being independently selected from the group consisting of halo, alkyl aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl. Non-limiting examples of suitable alkynyl groups include ethynyl, propynyl, 2-butynyl, 3-methylbutynyl, n-pentynyl, and decynyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein, or two substituents on adjacent carbons can be linked together to form

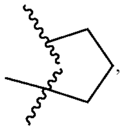, 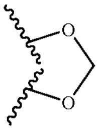 or 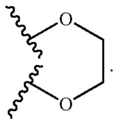.

Non-limiting examples of suitable aryl groups include phenyl and naphthyl.

"Arylene" means a difunctional group obtained by removal of a hydrogen atom from an aryl group that is defined above. Non-limiting examples of arylene include phenylene and naphthylene.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Heteroarylene" means a difunctional group obtained by removal of a hydrogen atom from a heteroaryl group that is defined above. Non-limiting examples of pyridylene, pyrazinylene, furanylene, thienylene and pyrimidinylene.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like. Further non-limiting examples of cycloalkyl include the following

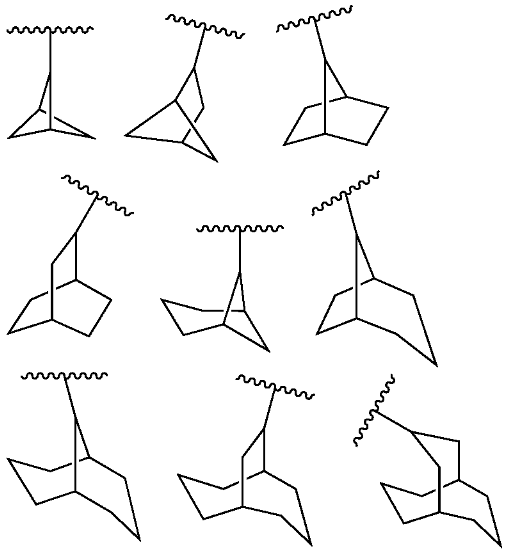

-continued

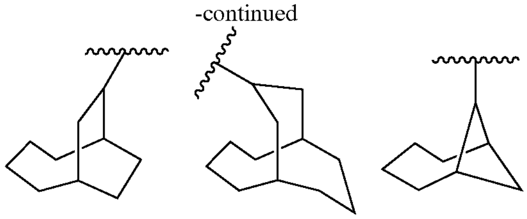

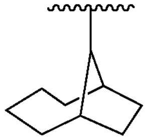

and

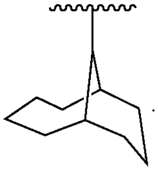

"Cycloalkylene" means a difunctional group obtained by removal of a hydrogen atom from a cycloalkyl group that is defined above. Non-limiting examples of cycloalkylene include cyclobutylene and cyclopropylene.

"Halo" means fluoro, chloro, bromo or iodo. Preferred are fluoro, chloro and bromo.

"Ring system substituent" means a substituent attached to an aromatic or non-aromatic ring system which, for example, replaces an available hydrogen on the ring system. Ring system substituents may be the same or different, each being independently selected from the group consisting of $—CF_3$, alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, =O, $—C(=N—CN)—NH_2$, $—C(=NH)—NH_2$, —C(=NH)—NH(alkyl), $Y_1Y_2N—$, $Y_1Y_2N$-alkyl-, $Y_1Y_2NC(O)—$, $Y_1Y_2NSO_2—$ and $—SO_2NY_1Y_2$, wherein $Y_1$ and $Y_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moieties are methylene dioxy, ethylenedioxy, $—C(CH_3)_2—$ and the like which form moieties such as, for example:

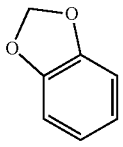

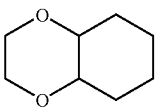

and

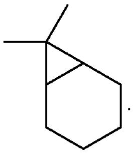

"Heterocyclyl" (or heterocycloalkyl) means a non-aromatic saturated monocyclic or multicyclic ring system comprising about 3 to about 10 ring atoms, preferably about 4 to about 7 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Heterocyclylene" means a difunctional group obtained by removal of a hydrogen atom from an heterocyclyl group that is defined above. Non-limiting examples of heterocyclylene include piperidylene, pyrrolidinylene, piperazinylene, morpholinylene, thiomorpholinylene, thiazolidinylene, 1,4-dioxanylene, tetrahydrofuranylene and tetrahydrothiophenylene.

It should be noted that in hetero-atom containing ring systems of this invention, there are no hydroxyl groups on carbon atoms adjacent to a N, O or S, nor is there an N or S group on a carbon adjacent to another heteroatom. Thus, for example, in the ring:

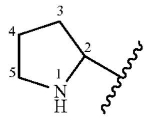

there is no —OH attached directly to carbons marked 2 and 5.

Those skilled in the art will recognize that certain compounds of formula I are tautomeric, and all such tautomeric forms are contemplated herein as part of the present invention. For example, the moieties:

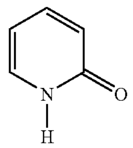

and

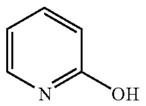

are considered equivalent in certain embodiments of this invention.

Similarly, "heteroarylalkyl or heteroaralkyl" and "cycloalkylalkyl" mean a heteroaryl- or cycloalkyl-group in which the heteroaryl, cycloalkyl and alkyl are as previously described. Preferred groups contain a lower alkyl group. The bond to the parent moiety is through the alkyl.

"Arylalkenyl" means a group derived from aryl and alkenyl as defined herein. Preferred arylalkenyls are those wherein aryl is phenyl and the alkenyl consists of about 3 to about 6 atoms. The arylalkenyl can be optionally substituted by one or more ring system substituents. The bond to the parent moiety is through a non-aromatic carbon atom.

"Arylalkynyl" means a group derived from aryl and alkynyl as defined herein. Preferred arylalkynyls are those wherein aryl is phenyl and the alkynyl consists of about 3 to about 6 atoms. The arylalkynyl can be optionally substituted by one or more ring system substituents. The bond to the parent moiety is through a non-aromatic carbon atom.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable heteroaralkyl groups include pyridylmethyl, and quinolin-3-ylmethyl. The bond to the parent moiety is through the alkyl.

"Heteroaralkylthio" means a heteroaralkyl-S— group in which the heteroaralkyl is as previously described. Preferred heteroaralkylthios contain a lower alkyl group. The bond to the parent moiety is through the sulfur.

"Heteroarylalkenyl" means a heteroaryl-alkenyl group in which the heteroaryl and the alkenyl are as previously described. Preferred heteroarylalkenyls contain a lower alkenyl group. The bond to the parent moiety is through the alkenyl.

"Heteroarylalkynyl" means a heteroaryl-alkynyl group in which the heteroaryl and the alkynyl are as previously described. Preferred heteroarylalkynyls contain a lower alkynyl group. The bond to the parent moiety is through the alkynyl.

"Heterocyclylalkyl" means a heterocyclyl-alkyl group in which the heterocyclyl and the alkyl are as previously described. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, butanoyl and cyclohexanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Alkoxyalkyl" means an alkoxy-alkyl group in which the alkoxy and alkyl groups are as previously described. Non-limiting examples of suitable alkoxyalkyl groups include ethoxyethyl, methoxymethyl and ethoxymethyl. The bond to the parent moiety is through the alkyl group.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkoxy" means an aralkyl-O— group in which the aralkyl group is as previously described. Non-limiting examples of suitable aralkoxy groups include benzyloxy and 1- or 2-naphthalenemethoxy. The bond to the parent moiety is through the ether oxygen.

"Alkylheteroaryl" means an alkyl-heteroaryl group in which the alkyl and heteroaryl groups are as previously described. The bond to the parent moiety is through the heteroaryl.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—C(O)— group in which the alkyl group is as previously described. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group in which the aryl group is as previously described. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group in which the aralkyl group is as previously described. Non-limiting example of a suitable aralkoxycarbonyl group is benzyloxycarbonyl. The bond to the parent moiety is through the carbonyl.

"Alkylsulfonyl" means an alkyl-$S(O_2)$— group in which the alkyl group is as previously described. Preferred groups are those in which the alkyl group is lower alkyl. The bond to the parent moiety is through the sulfonyl.

"Arylsulfonyl" means an aryl-$S(O_2)$— group in which the aryl group is as previously described. The bond to the parent moiety is through the sulfonyl.

"Cycloalkylalkyl" means a cycloalkyl-alkyl-group in which the cycloalkyl and alkyl group is as previously described. Preferred groups are those in which the alkyl group is lower alkyl. The bond to the parent moiety is through the alkyl.

"Heteroaralkoxy" means a heteroaralkyl-O— group in which the heteroaralkyl group is as previously described. The bond to the parent moiety is through the ether oxygen.

"Heteroarylsulfonyl" means a heteroaryl-$S(O_2)$— group in which the heteroaryl group is as previously described. The bond to the parent moiety is through the sulfonyl.

"Heteroarylthio" means a heteroaryl-S— group in which the heteroaryl group is as previously described. The bond to the parent moiety is through the sulfur.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The suffix "ene" on alkyl, aryl, hetercycloalkyl, etc. indicates a divalent moiety, e.g., —$CH_2CH_2$— is ethylene, and

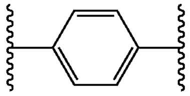

is para-phenylene.

It is understood that multicyclic divalent groups, for example, arylheterocycloalkylene, can be attached to other groups via bonds that are formed on either ring of said group. For example,

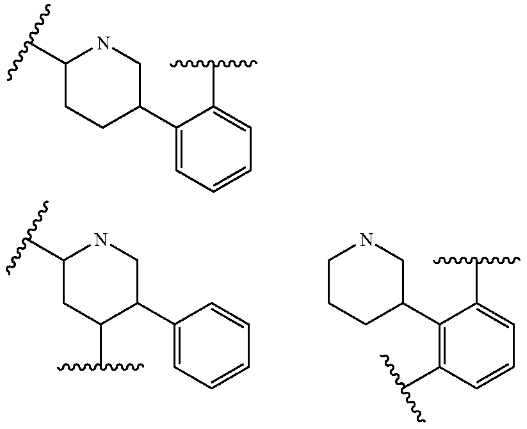

The term “optionally substituted” means optional substitution with the specified groups, radicals or moieties, in available position or positions.

Substitution on a cycloalkylalkyl, heterocycloalkylalkyl, arylalkyl, or heteroarylalkyl moiety includes substitution on the ring portion and/or on the alkyl portion of the group.

When a variable appears more than once in a group, e.g., $R^8$ in $—N(R^8)_2$, or a variable appears more than once in the structure of formula I, e.g., $R^{15}$ may appear in both $R^1$ and $R^3$, the variables can be the same or different.

With reference to the number of moieties (e.g., substituents, groups or rings) in a compound, unless otherwise defined, the phrases “one or more” and “at least one” mean that there can be as many moieties as chemically permitted, and the determination of the maximum number of such moieties is well within the knowledge of those skilled in the art. With respect to the compositions and methods comprising the use of “at least one compound of formula I,” one to three compounds of formula I can be administered at the same time, preferably one.

The wavy line  as a bond generally indicates a mixture of, or either of, the possible isomers, e.g., containing (R)- and (S)-stereochemistry. For example,

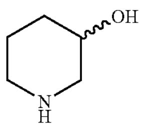 means containing both

-continued

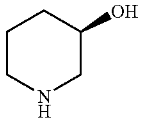 and 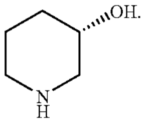

Lines drawn into the ring systems, such as, for example:

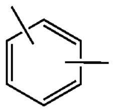

indicate that the indicated line (bond) may be attached to any of the substitutable ring carbon atoms.

As well known in the art, a bond drawn from a particular atom wherein no moiety is depicted at the terminal end of the bond indicates a methyl group bound through that bond to the atom, unless stated otherwise. For example:

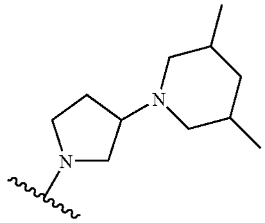 represents

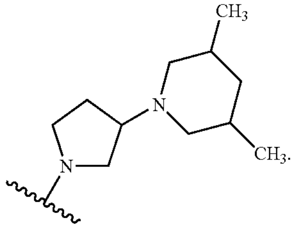

Polymorphic forms of the compounds of formula I, and of the salts, solvates and prodrugs of the compounds of formula I, are intended to be included in the present invention.

The term “isolated” or “in isolated form” for a compound refers to the physical state of said compound after being isolated from a synthetic process or natural source or combination thereof. The term “purified” or “in purified form” for a compound refers to the physical state of said compound after being obtained from a purification process or processes described herein or well known to the skilled artisan, in sufficient purity to be characterizable by standard analytical techniques described herein or well known to the skilled artisan.

It should also be noted that any heteroatom with unsatisfied valences in the text, schemes, examples and Tables herein is assumed to have the hydrogen atom(s) to satisfy the valences.

When a functional group in a compound is termed “protected”, this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1\text{-}C_8)$alkyl, $(C_2\text{-}C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1\text{-}C_2)$alkylamino$(C_2\text{-}C_3)$alkyl (such as β-dimethylaminoethyl), carbamoyl-$(C_1\text{-}C_2)$alkyl, N,N-di$(C_1\text{-}C_2)$alkylcarbamoyl-$(C_1\text{-}C_2)$alkyl and piperidino-, pyrrolidino- or morpholino$(C_2\text{-}C_3)$alkyl, and the like.

Similarly, if a compound of Formula (I) contains an alcohol functional group, a prodrug can be formed by the replacement of the hydrogen atom of the alcohol group with a group such as, for example, $(C_1\text{-}C_6)$alkanoyloxymethyl, 1-($(C_1\text{-}C_6)$alkanoyloxy)ethyl, 1-methyl-1-($(C_1\text{-}C_6)$alkanoyloxy)ethyl, $(C_1\text{-}C_6)$alkoxycarbonyloxymethyl, N—$(C_1\text{-}C_6)$alkoxycarbonylaminomethyl, succinoyl, $(C_1\text{-}C_6)$alkanoyl, α-amino$(C_1\text{-}C_4)$alkanyl, arylacyl and α-aminoacyl, or α-aminoacyl-α-aminoacyl, where each α-aminoacyl group is independently selected from the naturally occurring L-amino acids, $P(O)(OH)_2$, $—P(O)(O(C_1\text{-}C_6)alkyl)_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1\text{-}C_{10})$alkyl, $(C_3\text{-}C_7)$cycloalkyl, benzyl, or R-carbonyl is a natural α-aminoacyl or natural α-aminoacyl, $—C(OH)C(O)OY^1$ wherein $Y^1$ is H, $(C_1\text{-}C_6)$alkyl or benzyl, $—C(OY^2)Y^3$ wherein $Y^2$ is $(C_1\text{-}C_4)$alkyl and $Y^3$ is $(C_1\text{-}C_6)$alkyl, carboxy$(C_1\text{-}C_6)$alkyl, amino$(C_1\text{-}C_4)$alkyl or mono-N— or di-N,N-$(C_1\text{-}C_6)$alkylaminoalkyl, $—C(Y^4)Y^5$ wherein $Y^4$ is H or methyl and $Y^5$ is mono-N— or di-N,N-$(C_1\text{-}C_6)$alkylamino morpholino, piperidin-1-yl or pyrrolidin-1-yl, and the like.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compounds of formula I form salts which are also within the scope of this invention. Reference to a compound of formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula I may be formed, for example, by reacting a compound of formula I with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

Compounds represented by formula I can be beta-secretase inhibitors useful for the prevention and treatment of Alzheimer's disease.

An aspect of this invention is a method of treating a mammal (e.g., human) having a disease or condition mediated or exacerbated by BACE-1 (an aspartyl protease) by administering a therapeutically effective amount of at least one compound of Formula I, or a pharmaceutically acceptable salt or solvate of said compound to the mammal.

"Effective amount" or "therapeutically effective amount" is meant to describe an amount of compound or a composition of the present invention effective in inhibiting BACE-1 and thus producing the desired therapeutic effect in a suitable patient.

A preferred dosage is about 0.001 to 1000 mg/kg of body weight/day of the compound of Formula I or a pharmaceutically acceptable salt or solvate thereof. An especially preferred dosage is about 0.01 to 30 mg/kg of body weight/day of a compound of Formula I, or a pharmaceutically acceptable salt or solvate of said compound.

Still yet another aspect of this invention is a method of treating a cognitive or neurodegenerative disease, such as Alzheimer's disease, comprising administering to a mammal in need of such treatment a therapeutically effective amount of at least one compound of Formula I, or a pharmaceutically acceptable salt or solvate of said compound.

A further aspect of this invention is a method for treating a cognitive or neurodegenerative disease such as Alzheimer's disease, comprising administering to a mammal a therapeutically effective amount of at least one compound of Formula I, or a pharmaceutically acceptable salt or solvate of said compound.

This invention is also directed to pharmaceutical compositions, which comprise at least one compound of Formula I, or a pharmaceutically acceptable salt or solvate of said compound and at least one pharmaceutically acceptable carrier.

This invention is also directed to pharmaceutical compositions for the treatment of neurodegenerative diseases such as Alzheimer's disease which comprise an effective treating amount of at least one compound of Formula I, or a pharmaceutically acceptable salt or solvate of said compound and at least one pharmaceutically acceptable carrier.

A preferred dosage is about 0.001 to 1000 mg/kg of body weight/day of the compound of Formula I or a pharmaceutically acceptable salt or solvate thereof. An especially preferred dosage is about 0.01 to 30 mg/kg of body weight/day of a compound of Formula I, or a pharmaceutically acceptable salt or solvate of said compound.

Still yet another aspect of this invention is a method of treating a cognitive or neurodegenerative disease, such as Alzheimer's disease, comprising administering to a mammal in need of such treatment a therapeutically effective amount of at least one compound of Formula I, or a pharmaceutically acceptable salt or solvate of said compound.

A further aspect of this invention is a method for treating a cognitive or neurodegenerative disease such as Alzheimer's disease, comprising administering to a mammal a therapeutically effective amount of at least one compound of Formula I, or a pharmaceutically acceptable salt or solvate of said compound.

This invention is also directed to pharmaceutical compositions, which comprise at least one compound of Formula I, or a pharmaceutically acceptable salt or solvate of said compound and at least one pharmaceutically acceptable carrier.

This invention is also directed to pharmaceutical compositions for the treatment of neurodegenerative diseases such as Alzheimer's disease which comprise an effective treating amount of at least one compound of Formula I, or a pharmaceutically acceptable salt or solvate of said compound and at least one pharmaceutically acceptable carrier.

For the combination aspect, the use of any β-secretase inhibitor other than those of formula I is contemplated; β-secretase inhibitory activity can be determined by the procedures described below. Useful β-secretase inhibitors are those disclosed in, but are not limited to, WO 02/02505, WO 02/02506, WO 02/02512, WP 02/02518, WO 02/02520 and WO 02/088101.

Still yet other aspects of this invention are combinations of a compound of Formula I, or a pharmaceutically acceptable salt or solvate of said compound and other compounds as described below.

Accordingly, included within the invention is a method for treating neurodegenerative diseases such as Alzheimer's, comprising administering to a mammal (e.g., a female or male human)

a. an amount of a first compound, said first compound being a compound of Formula I, or a pharmaceutically acceptable salt or solvate of said compound; and b. an amount of a second compound, said second compound being a cholinesterase inhibitor.

Cholinesterase inhibitors for use in the combination include acetyl- and/or butyrylchlolinesterase inhibitors. Examples of cholinesterase inhibitors include tacrine, donepezil, rivastigmine, galantamine, pyridostigmine and neostigmine.

Accordingly, included within the invention is a method for treating neurodegenerative diseases such as Alzheimer's, comprising administering to a mammal (e.g., a female or male human)

a. an amount of a first compound, said first compound being a compound of Formula I, or a pharmaceutically acceptable salt or solvate of said compound; and b. an amount of a second compound, said second compound being an anti-amyloid antibody. Anti amyloid antibodies are described, for example, in Hock et al, *Nature Medicine,* 8 (2002), p. 1270-1275.

Accordingly, included within the invention is a method for treating neurodegenerative diseases such as Alzheimer's, comprising administering to a mammal (e.g., a female or male human)

a. an amount of a first compound, said first compound being a compound of Formula I, or a pharmaceutically acceptable salt or solvate of said compound; and b. an amount of a second compound, said second compound being an anti-inflammatory compound. Examples of anti-inflammatory compounds include but are non limited to non-steroidal anti-inflammatory drugs such as diclofenac (Voltaren, Cataflam), diflunisal (Dolobid), etodolac (Lodine), flurbiprofen (Ansaid), ibuprofen (Motrin, Advil), indomethacin (Indocin), ketoprofen (Orudis, Oruvail), ketorolac (Toradol), nabumetone (Relafen), naproxen (Naprosyn, Alleve), oxaprozin (Daypro), piroxicam (Feldene), sulindac (Clinoril), tolmetin (Tolectin), celecoxib (Celebrex) and rofecoxib (Vioxx).

Accordingly, included within the invention is a method for treating neurodegenerative diseases such as Alzheimer's, comprising administering to a mammal (e.g., a female or male human)

a. an amount of a first compound, said first compound being a compound of Formula I, or a pharmaceutically acceptable salt or solvate of said compound; and b. an amount of a second compound, said second compound being a gamma secretase inhibitor. Gamma-secretase inhibitors for use in the combination of this invention can be determined by procedures known in the art. Typical gamma-secretase inhibitors include, but are not limited to, those described in WO 03/013527, U.S. Pat. No. 6,683,091, WO 03/066592, U.S. Ser. No. 10/663,042, filed Sep. 16, 2003, WO 00/247671, WO 00/050391, WO 00/007995 and WO 03/018543.

Accordingly, included within the invention is a method for treating neurodegenerative diseases such as Alzheimer's, comprising administering to a mammal (e.g., a female or male human)

a. an amount of a first compound, said first compound being a compound of Formula I, or a pharmaceutically acceptable salt or solvate of said compound; and b. an amount of a second compound, said second compound being a HMG-CoA reductase inhibitor compound. HMG-CoA reductase inhibitors for use in combination with compounds of formula I include the "stains," e.g., atorvastatin, lovastatin, simvistatin, pravastatin, fluvastatin and rosuvastatin.

Accordingly, included within the invention is a method for treating neurodegenerative diseases such as Alzheimer's, comprising administering to a mammal (e.g., a female or male human)

a. an amount of a first compound, said first compound being a compound of Formula I, or a pharmaceutically acceptable salt or solvate of said compound; and b. an amount of a second compound, said second compound being a N-methyl-D-aspartate receptor antagonist. A suitable N-methyl-D-aspartate receptor antagonist is, for example, memantine.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 1000 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 50 mg/day, in two to four divided doses.

The amount and frequency of administration of the compounds of the combinations (beta secreatse inhibitors other than those of formula I, NSAIDS, statin drugs, cholinesterase inhibitors, etc.), and/or the pharmaceutically acceptable salts thereof will be regulated according to the judgment of the attending clinician considering such factors as age, condition and size of the patient as well as severity of the symptoms being treated.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

When a compound of formula I is used in combination with a β-secretase inhibitors other than those of formula I, an HMG-CoA reductase inhibitor, a gamma-secretase inhibitor, a non-steroidal anti-inflammatory agent, an N-methyl-D-aspartate receptor antagonist, a cholinesterase inhibitor or an anti-amyloid antibody to treat a cognitive disorder or neurodegenerative disorder, the active components may be co-administered simultaneously or sequentially, or a single pharmaceutical composition comprising a compound of formula I and one of the other agents in a pharmaceutically acceptable carrier can be administered. The components of the combination can be administered individually or together in any conventional oral or parenteral dosage form such as capsule, tablet, powder, cachet, suspension, solution, suppository, nasal spray, etc. The dosage of the β-secretase inhibitors other than those of formula I, HMG-CoA reductase inhibitor, gamma-secretase inhibitor, non-steroidal anti-inflammatory agent, N-methyl-D-aspartate receptor antagonist, cholinesterase inhibitor or anti-amyloid antibody can be determined from published material, and may range from 0.001 to 100 mg/kg body weight.

When separate pharmaceutical compositions of a compound of formula I and a β-secretase inhibitors other than those of formula I, an HMG-CoA reductase inhibitor, a gamma-secretase inhibitor, a non-steroidal anti-inflammatory agent, an N-methyl-D-aspartate receptor antagonist, a cholinesterase inhibitor or an anti-amyloid antibody are to be administered, they can be provided in a kit comprising in a single package, one container comprising a compound of formula I in a pharmaceutically acceptable carrier, and a separate container comprising the other agent in a pharmaceutically acceptable carrier, with the compound of formula I and the other agent being present in amounts such that the combination is therapeutically effective. A kit is advantageous for administering a combination when, for example, the components must be administered at different time intervals or when they are in different dosage forms.

The invention also includes multi-agent compositions, kits and methods of treatment, e.g., a compound of formula I can be administered in combination with an HMG-CoA reductase inhibitor and a non-steroidal anti-inflammatory agent.

Compounds of Formula I can be produced by processes known to those skilled in the art using either solution phase or solid phase synthesis as shown in the following reaction schemes, in the preparations and examples below, but those skilled in the art will recognize that other procedures can also be suitable.

In the Schemes and in the Examples below, the following abbreviations are used:

methyl: Me; ethyl: Et; propyl: Pr; butyl: Bu; benzyl: Bn
ethyl acetate: EtOAc
benzyloxycarbonyl: Cbz
N,N-dimethylformamide: DMF:
1-(3-dimethylaminopropyl)-3-ethylcarbodiimide hydrochloride: EDC or EDCI
room temperature: RT
hour: h
minute: min
retention time: $t_R$
trifluoroacetic acid: TFA
tetrahydrofuran: THF
1-hydroxybenzotriazole: HOBt
methanol: MeOH
ethanol: EtOH
diethyl ether: $Et_2O$
acetic acid: AcOH
dimethylsulfoxide: DMSO
lithium diisopropylamide: LDA
tert-dimethylsilyl chloride: TBSCI
tert-dimethylsilyl: TBS
triphenyl phosphine: $PPh_3$
diisopropyl azodicarboxylate: DIAD
copper(I) bromide-dimethyl sulfide: $CuBr-Me_2S$
tertiary butyloxycarbonyl: Boc
Palladium tetrakis (Triphenylphosphine): $Pd(PPh_3)_4$
Triphenylphosphine: $PPh_3$
Tetrabutylammonium fluoride: TBAF
Triethylamine: $Et_3N$, $NEt_3$ or TEA
Lithium borohydride: $LiBH_4$
(trimethylsilyl) diazomethane: $TMSCHN_2$
benzyl bromide: BnBr
Lithium aluminum hydride: LAH or $LiAlH_4$
Di-tert-butyl dicarbonate: $(Boc)_2O$
4-dimethylaminopyridine: DMAP
butyllithium: BuLi
Benzyl chloride: BnCl
oxalyl chloride: $(COCl)_2$
Palladium diphenylphosphinoferrocene chloride: $Pd(dppf)Cl_2$
Preparative thin layer chromatography: PTLC
high pressure liquid chromatography: HPLC
liquid chromatography mass spectrometry: LCMS
thin layer chromatography: TLC
Boron trifluoride diethyl etherate: $BF_3-Et_2O$
Triethylsilane: $Et_3SiH$
N,N diisopropylethylamine: DIEA
Diisopropylamine: DIPA
Acetic anhydride: $Ac_2O$
dimethylacetamide: DMA General Schemes:
General Scheme 1
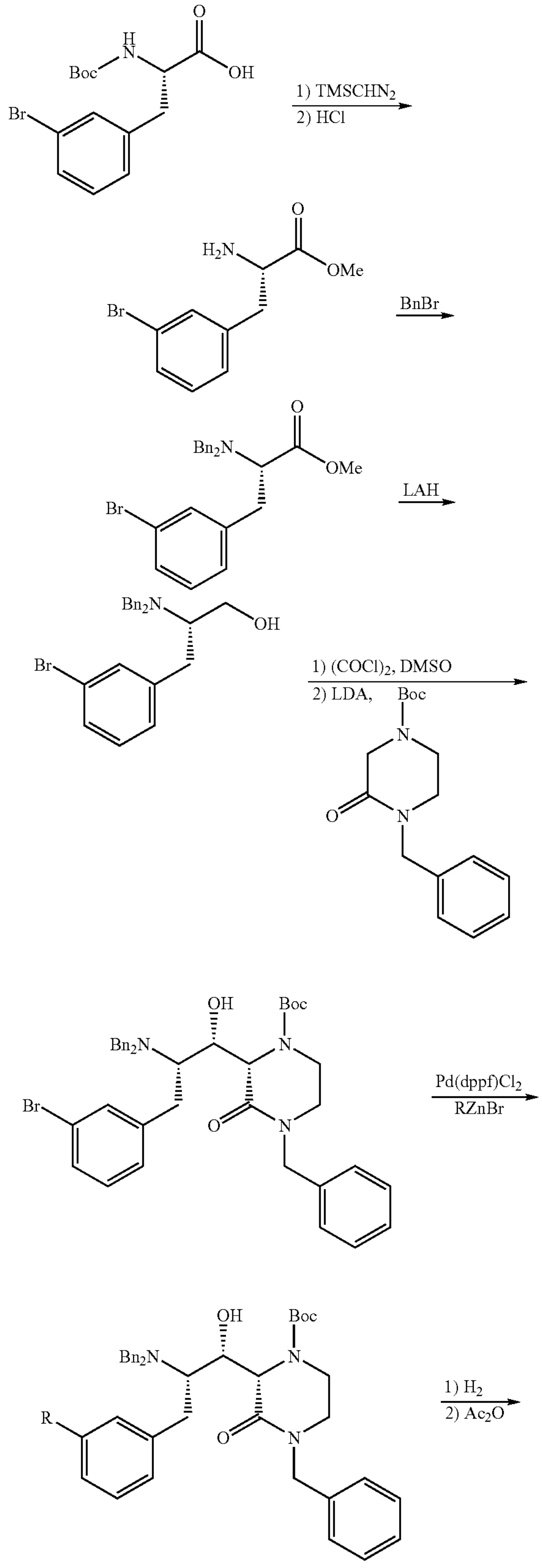
-continued
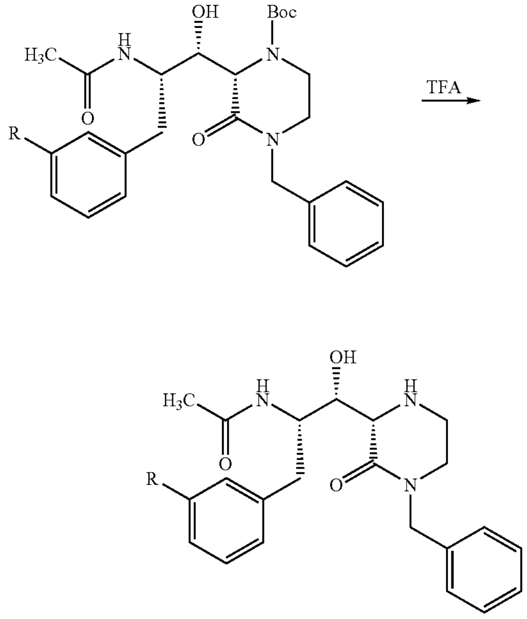
General Scheme 2
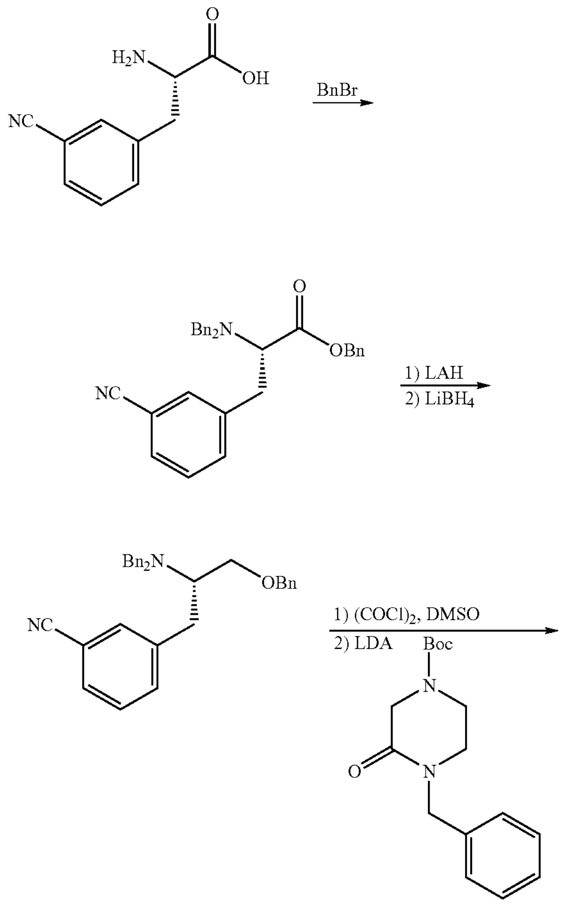

-continued
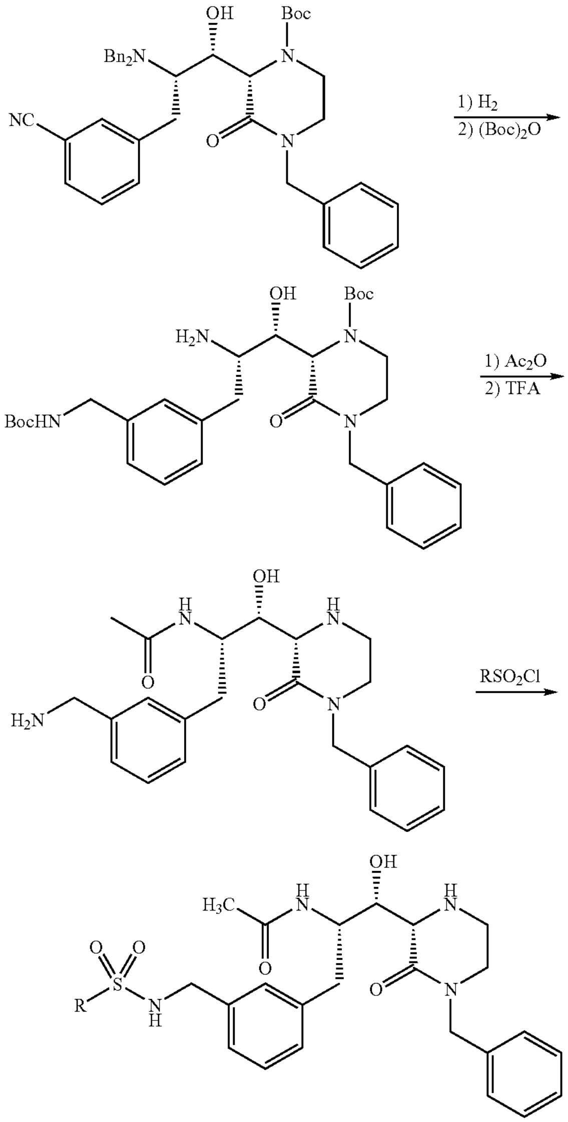
General Scheme 3
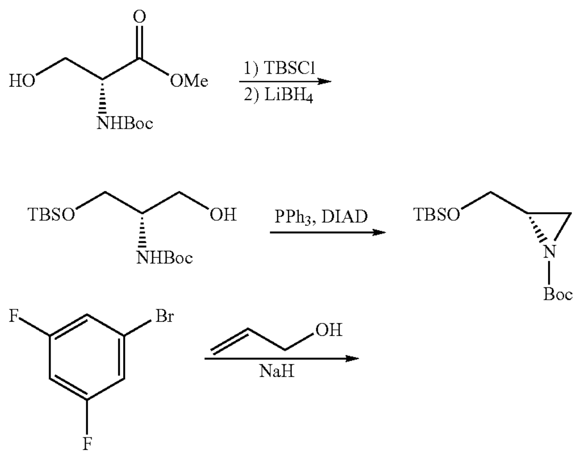
-continued
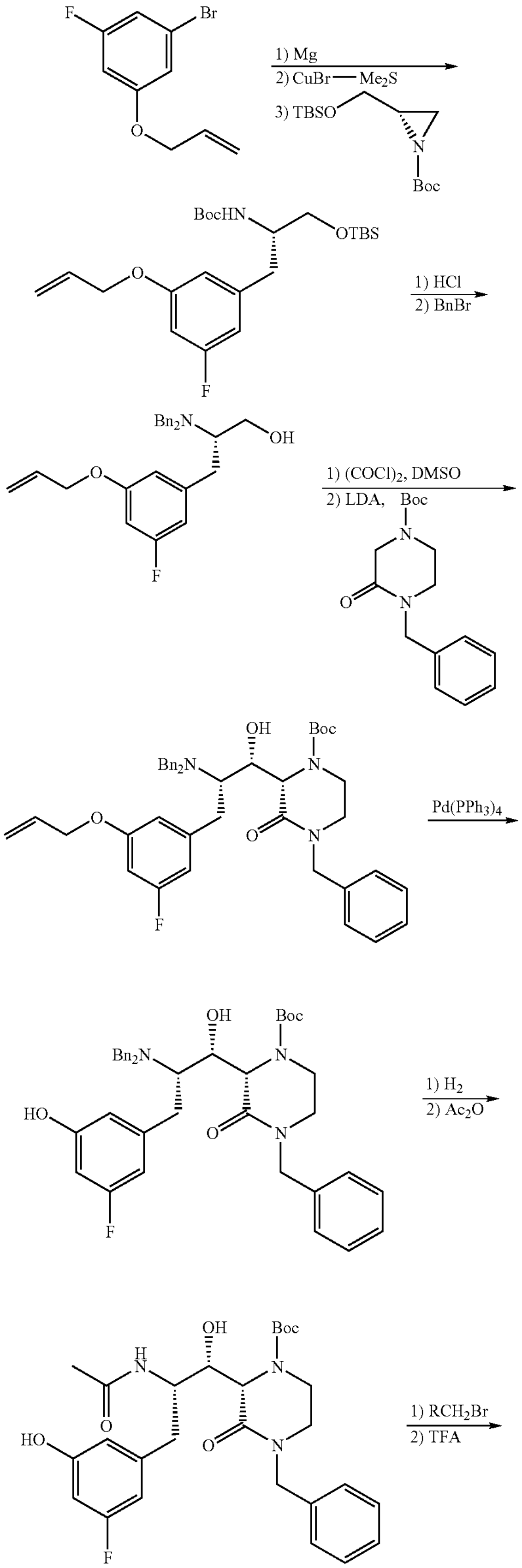

-continued
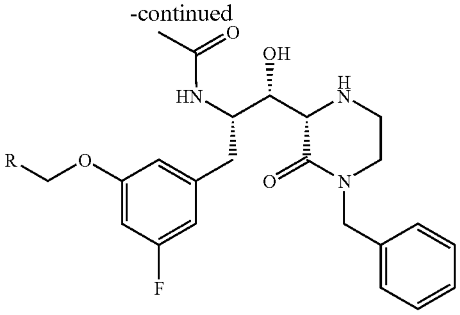
-continued
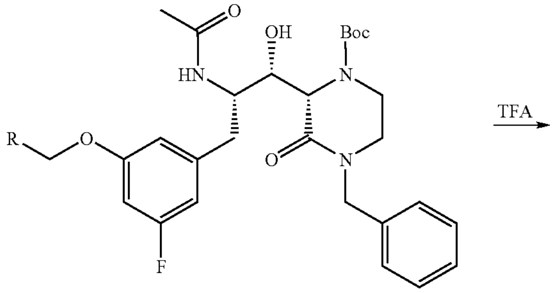
General Scheme 4
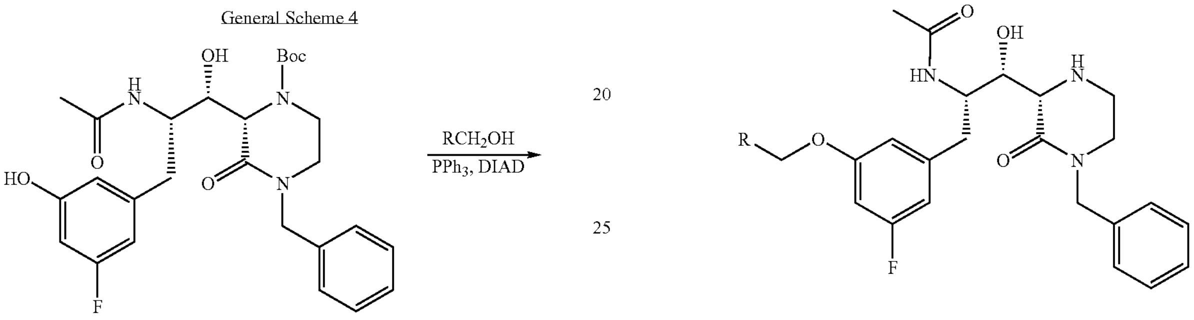
General Scheme 5
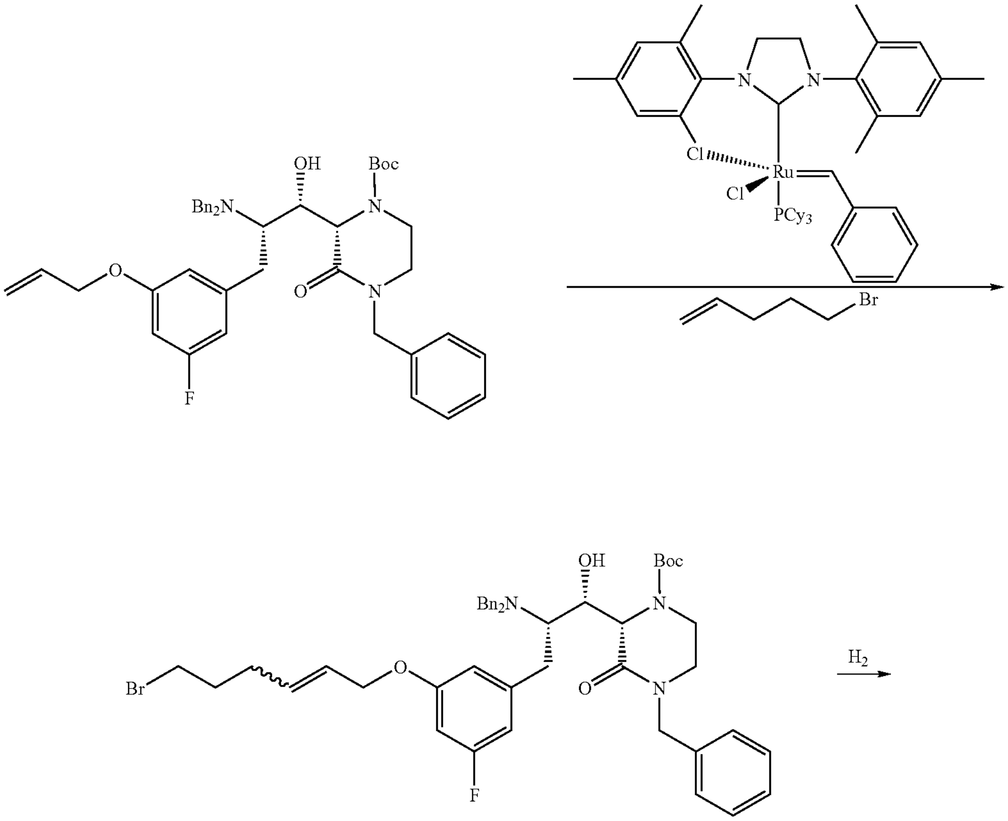

-continued

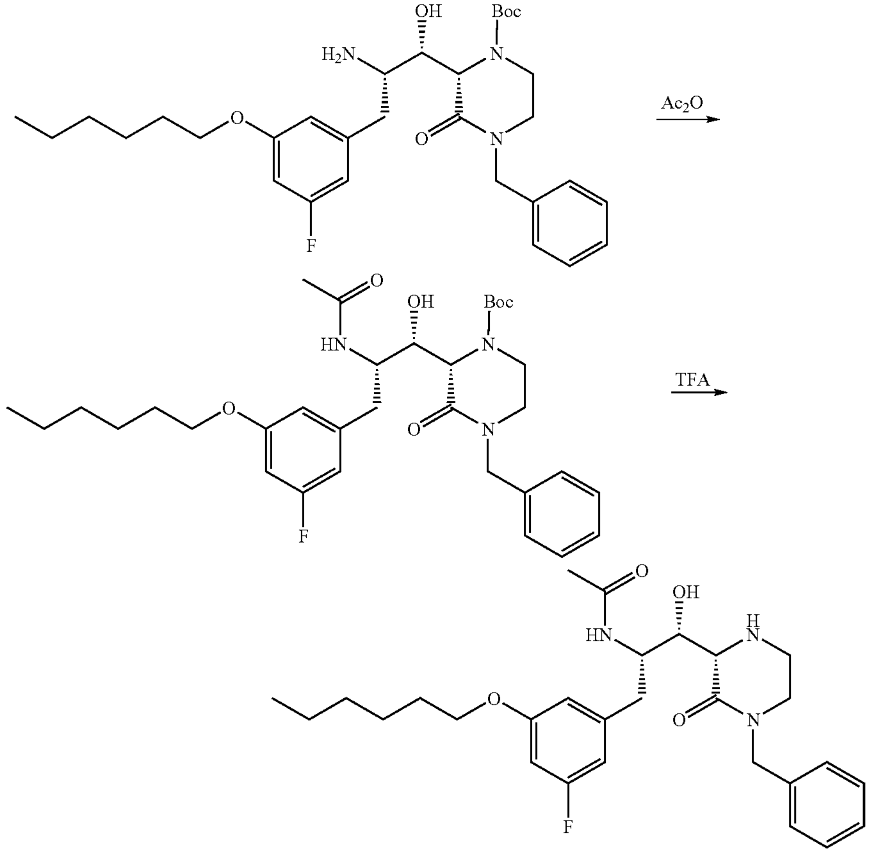

PREPARATIVE EXAMPLE 1

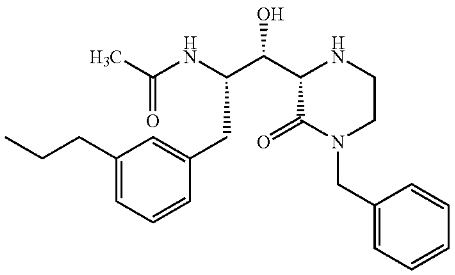

Step 1

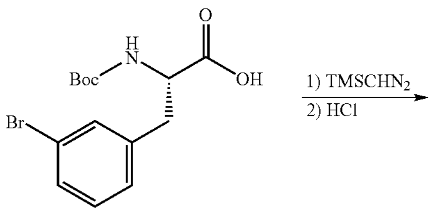

-continued

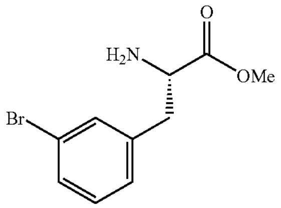

To an ice-cold solution of Boc-L-3-bromophenylalanine (9.44 g, 27.4 mmol) in toluene (60 ml) and MeOH (12 ml) was added 2M (trimethylsilyl) diazomethane in hexanes (20 ml). The solution was stirred at RT for 1 h and AcOH (2 ml) was added. The mixture was concentrated and the residue was dissolved in 20% MeOH/$CH_2Cl_2$ (40 ml). The solution was cooled in an ice-water bath and 4N HCl/dioxane (36 ml) was added via dropping funnel over 30 min. After the addition was complete, the mixture was warmed to RT and stirred for 4 h. The mixture was concentrated to give the product (8.95 g, 100%). MS m/e 258 $(M+H)^+$ Step 2

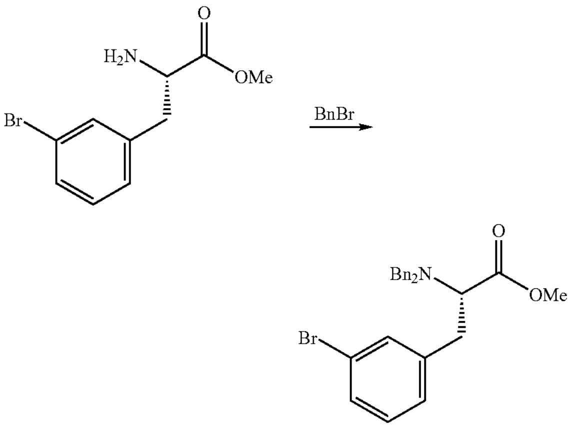

To a solution of the product of Step 1 (8.95 g, 27.4 mmol) in THF (80 ml) and DMSO (20 ml) were added sodium bicarbonate (14.6 g, 174 mmol) and benzyl bromide (15.9 g, 91.4 mmol). The mixture was stirred at 80° C. for 24 h. The mixture was cooled to RT and water (120 ml) and EtOAc (100 ml) were added. The aqueous layer was extracted with EtOAc (2×100 ml) and the combined organic layer was washed with saturated sodium bicarbonate (100 ml), dried ($MgSO_4$), concentrated, and purified by column chromatography (gradient EtOAc/Hexanes 0-5%) to give the product (10.4 g, 87%). MS m/e 438 $(M+H)^+$ Step 3

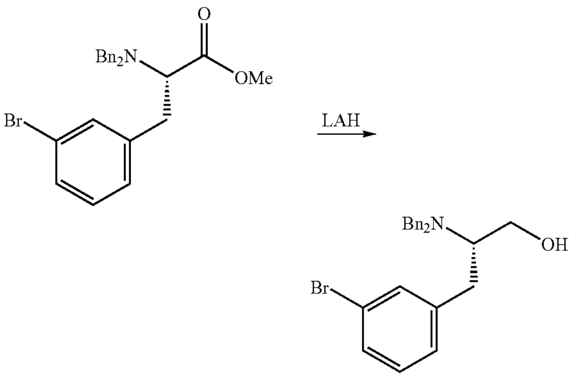

To an ice-cold solution of the product of Step 2 (10.4 g, 23.8 mmol) in THF (100 ml) was added LAH (1.42 g, 37.4 mmol) in several portions. After the addition was complete, the mixture was warmed to RT and stirred for 4.5 h. The reaction was quenched with slow addition of water (5 ml), 1N NaOH (10 ml), and water (5 ml). The mixture was stirred until the grey color disappeared then filtered. The filtrate was concentrated and the residue was partitioned between $CH_2Cl_2$ (100 ml) and brine. The organic layer was dried ($MgSO_4$), concentrated, and purified by column chromatography (gradient EtOAc/Hexanes 0-10%) to give the product (5.70 g, 58%). MS m/e 410 $(M+H)^+$ Step 4

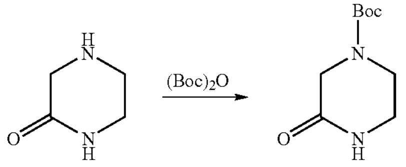

To a solution of piperazinone (10.0 g, 100 mmol), triethylamine (20.2 g, 200 mmol), and DMAP (50 mg) in $CH_2Cl_2$ (250 ml) in an ice-water bath was added $(Boc)_2O$ (22.9 g, 105 mmol) slowly. The mixture was stirred in the ice-water bath for 1 h and at RT for 4.5 h. The mixture was diluted with $CH_2Cl_2$ (250 ml), washed with water (200 ml), 5% citric acid (200 ml), 1N HCl (200 ml), saturated sodium bicarbonate (20 ml) and brine. The organic layer was dried ($MgSO_4$) and concentrated to give the product (18.0 g, 90%). MS m/e 201 $(M+H)^+$ Step 5

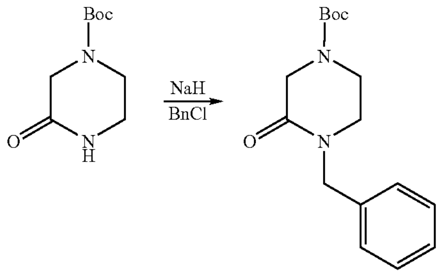

To a solution of the product of Step 4 (10.0 g, 50.0 mmol) in anhydrous DMF (250 ml) in an ice-water bath were added sodium hydride (2.40 g, 60.0 mmol) and benzyl chloride (6.60 g, 52.5 mmol). The mixture was stirred at RT for 4.5 h. The reaction was quenched with water (10 ml), diluted with $CH_2Cl_2$ (500 ml), and washed with water (2×250 ml). The organic layer was extracted with saturated $NH_4Cl$ (200 ml), dried ($MgSO_4$), concentrated, and purified by column chromatography (gradient MeOH/$CH_2Cl_2$ 0-5%) to give the product (10.7 g, 74%). $^1$H-NMR ($CDCl_3$): δ=7.2-7.3 (m, 5H), 4.57 (s, 2H), 4.10 (s, 2H), 3.53 (m, 2H), 3.19 (m, 2H), 1.41 (s, 9H).

Step 6

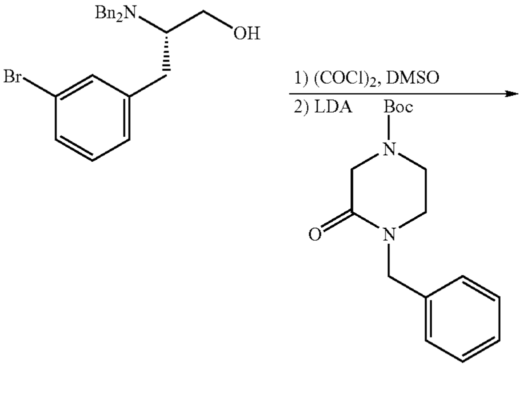

-continued

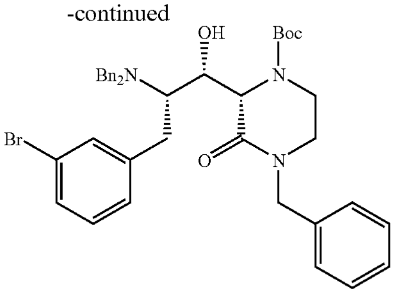

To a solution of oxalyl chloride (1.08 g, 8.30 mmol) in $CH_2Cl_2$ (7 ml) in a dry ice-acetone bath was added DMSO (1.14 g, 14.6 mmol). After 5 min, a solution of the product of Step 3 (3.01 g, 7.34 mmol) in $CH_2Cl_2$ (7 ml) was added and the mixture was stirred for 1 h. Diisopropylethylamine (3.28 g, 25.4 mmol) was added and after 2 min the cooling bath was removed. The mixture was stirred for 30 min and diluted with water (50 ml). $CH_2Cl_2$ (40 ml) was added and the aqueous layer was extracted with $CH_2Cl_2$ (40 ml). The combined organic layer was washed with brine, dried ($MgSO_4$), and concentrated to give the aldehyde, which was not further purified.

To a solution of diisopropylamine (896 mg, 8.85 mmol) in THF (5 ml) in a dry ice-acetone bath was added 1.6 M butyllithium in hexanes (5.5 ml, 8.8 mmol). After 5 min the mixture was put in an ice-water bath and stirred for 20 min. The solution was cooled in the dry ice-acetone bath again and a solution of the product of Step 5 (2.14 g, 7.37 mmol) in THF (8 ml) was added. The mixture was stirred for 1 h. A solution of the above aldehyde in THF (10 ml) was added and the mixture was stirred for 1.5 h. The reaction was quenched with water and partitioned between ether (4×50 ml) and water (50 ml). The combined organic layer was washed with brine (50 ml), dried ($MgSO_4$), concentrated, and purified by column chromatography (gradient EtOAc/Hexanes 0-20%) to give the product (2.67 g, 52%). MS m/e 698 $(M+H)^+$ Step 7

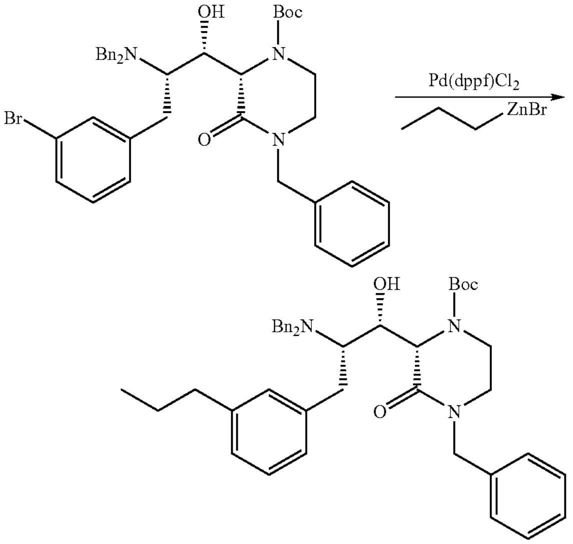

A mixture of the product of Step 6 (194 mg, 0.277 mmol), 0.5 M propylzinc bromide in THF (2.2 ml), and $Pd(dppf)Cl_2$ (25 mg, 0.031 mmol) was degassed and heated to 45° C. in a sealed tube for 16 h. The mixture was diluted with $CH_2Cl_2$ (50 ml) and washed with aqueous $NH_4OH$ (30 ml). The organic layer was dried ($MgSO_4$), concentrated, and purified by PTLC (20% EtOAc/Hexanes) to give the product (124 mg, 68%). MS m/e 662 $(M+H)^+$ Step 8

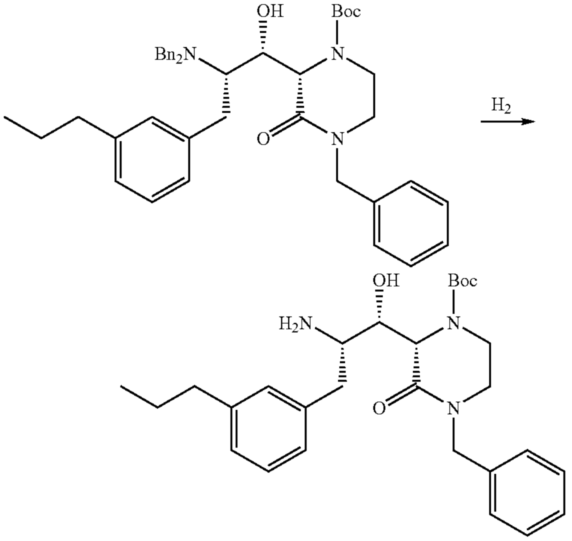

A mixture of the product of Step 7 (124 mg, 0.188 mmol), 20% $Pd(OH)_2/C$ (169 mg), and catalytic amount of AcOH in EtOH (12 ml) was stirred under $H_2$ (1 atm) for 4 h. The mixture was filtered and concentrated. The residue was partitioned between $CH_2Cl_2$ (40 ml) and 1N NaOH (20 ml). The organic layer was dried ($MgSO_4$) and concentrated to give the product (81 mg, 89%). MS m/e 482 $(M+H)^+$ Step 9

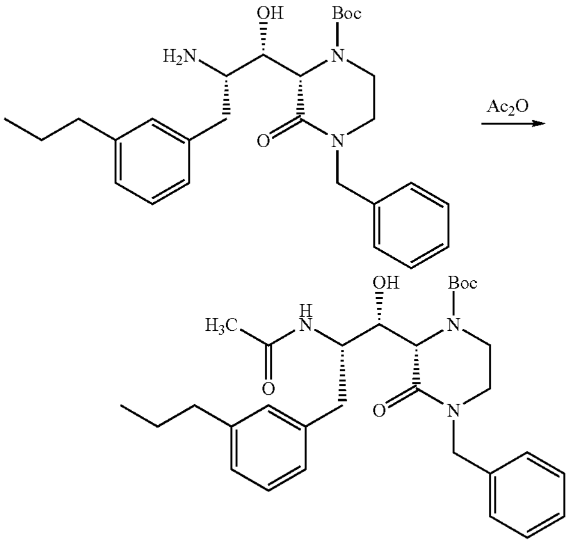

A mixture of the product of Step 8 (81 mg, 0.17 mmol), triethylamine (24 μl, 0.17 mmol), and acetic anhydride (17 mg, 0.17 mmol) in $CH_2Cl_2$ (8 ml) was stirred in an ice-water bath for 2 h. The mixture was diluted with $CH_2Cl_2$ (50 ml) and washed with 1N NaOH (20 ml). The organic layer was dried ($MgSO_4$), concentrated, and purified by PTLC (3% MeOH/$CH_2Cl_2$) to give the product (81 mg, 91%). MS m/e 524 $(M+H)^+$ Step 10

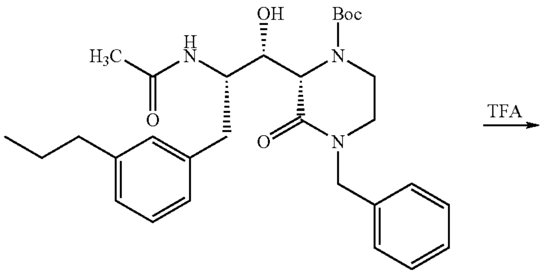

-continued

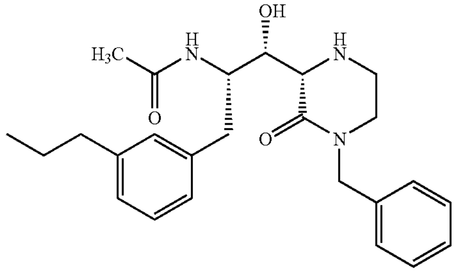

A solution of the product of Step 9 (81 mg, 0.15 mmol) and TFA (1 ml) in $CH_2Cl_2$ (6 ml) was stirred in an ice-water bath for 1 h then at RT for 3 h. The mixture was diluted with $CH_2Cl_2$ (40 ml) and washed with aqueous $NH_4OH$ (20 ml). The organic layer was dried ($MgSO_4$), concentrated, and purified by PTLC (5% MeOH/$CH_2Cl_2$) to give the product (42 mg, 67%). $^1$H-NMR ($CDCl_3$): δ=7.1-7.4 (m, 8H), 7.01 (m, 1H), 6.15 (m, 1H), 4.72 (d, 1H, J=14.8 Hz), 4.46 (m, 1H), 4.35 (d, 1H, J=14.8 Hz), 4.04 (m, 1H), 3.40 (m, 1H), 3.27 (m, 1H), 3.06 (m, 2H), 2.95 (m, 1H), 2.83 (m, 1H), 2.65 (m, 1H), 2.54 (t, 2H, J=7.6 Hz), 1.86 (s, 3H), 1.61 (m, 2H), 0.91 (t, 3H, J=7.4 Hz). LCMS $t_R$=3.33 min m/e 424 $(M+H)^+$ By essentially the same procedure set forth in Preparative Example 1, the following examples were prepared.

| | LCMS $t_R$ (min) | $(M + H)^+$ |
|---|---|---|
| 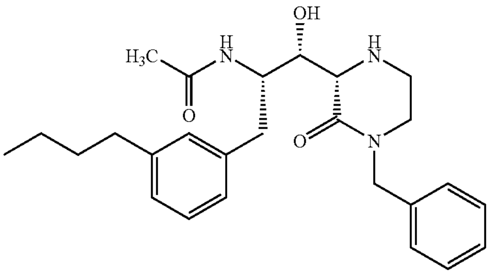 | 3.77 | 438 |
| 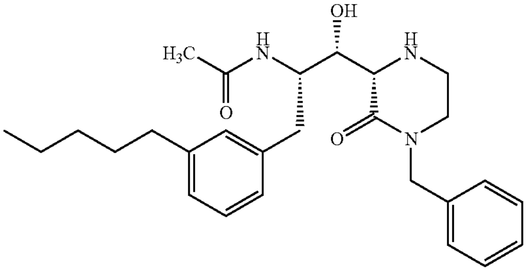 | 3.42 | 452 |
| 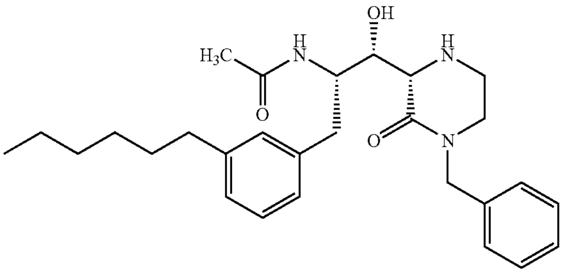 | 4.12 | 466 |

-continued

| | LCMS $t_R$ (min) | $(M + H)^+$ |
|---|---|---|
| 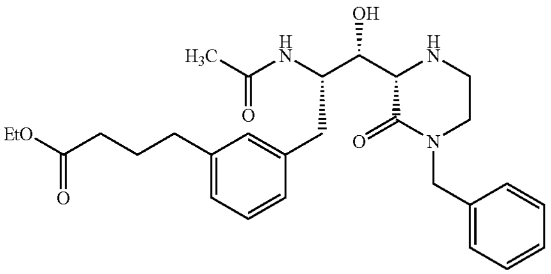 | 3.22 | 496 |

PREPARATIVE EXAMPLE 2

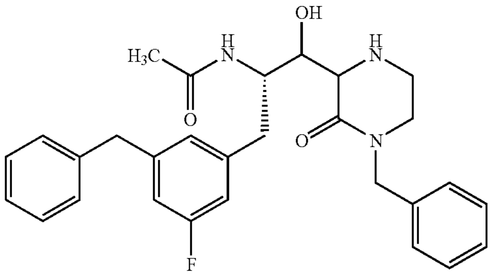

Step 1

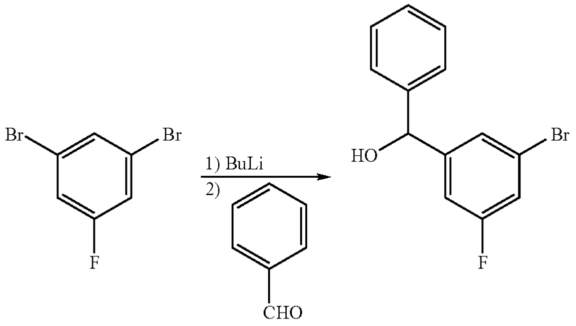

To a solution of 1,3-dibromo-5-fluorobenzene (5.105 g, 20.11 mmol) in ether (50 ml) in a dry ice-acetone bath was added 1.6M butyllithium in hexanes (12.5 ml, 20.0 mmol). After 2 h benzaldehyde (2.287 g, 21.55 mmol) was added and the mixture was allowed to warm to RT slowly and stirred for 16 h. The reaction was quenched with brine (70 ml) and the aqueous layer was extracted with ether (50 ml). The combined organic layer was dried ($MgSO_4$), concentrated, and purified by column chromatography (gradient EtOAc/Hexanes 0-10%) to give the product (5.036 g, 90%). $^1$H-NMR ($CDCl_3$): δ=7.30 (m, 6H), 7.09 (m, 1H), 7.02 (m, 1H), 5.73 (s, 1H).

Step 2

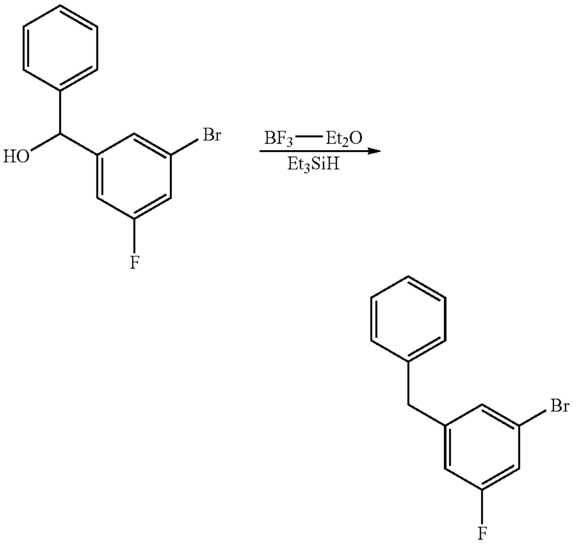

To a solution of the product of Step 1 (5.036 g, 17.92 mmol) in $CH_2Cl_2$ (70 ml) was added triethylsilane (12.0 ml, 74.3 mmol). The solution was cooled in an ice-water bath and boron trifluoride diethyl etherate (3.35 ml, 26.7 mmol) was added. The mixture was slowly warmed to RT and stirred for 5 h. The reaction was cooled in an ice-water bath and quenched with saturated $NaHCO_3$ (100 ml). The aqueous layer was extracted with $CH_2Cl_2$ (50 ml) and the combined organic layer was dried ($MgSO_4$) and concentrated to give the product (4.09 g, 86%). $^1$H-NMR ($CDCl_3$): δ=7.28 (m, 2H), 7.20 (m, 1H), 7.12 (m, 3H), 7.04 (m, 1H), 6.78 (m, 1H), 3.90 (s, 2H).

Step 3

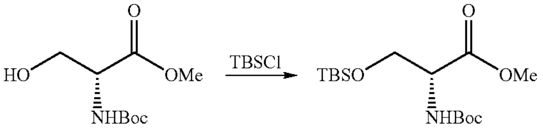

To an ice-cold solution of N-Boc-D-serine methyl ester (10.0 g, 45.6 mmol) in DMF (150 ml) were added imidazole (9.26 g, 136 mmol) and TBSCI (7.56 g, 50.16 mmol). The mixture was stirred at RT for 20 h and concentrated. The residue was dissolved with EtOAc (300 ml) and extracted with saturated $NH_4Cl$ and sodium bicarbonate. The organic layer was dried ($MgSO_4$) and concentrated to give the product (16.5 g, 100%). MS m/e 356 $(M+Na)^+$ Step 4

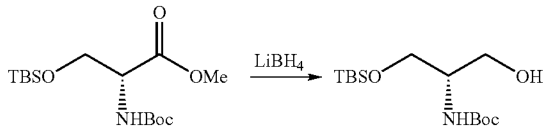

To a solution of the product of Step 3 (16.5 g, 45.6 mmol) in THF (150 ml) was added 2M lithium borohydride in THF (37.1 ml) slowly. The mixture was stirred at RT for 2.5 h. The reaction was quenched with saturated $NH_4Cl$ and extracted with EtOAc (2×250 ml). The combined organic layer was washed with saturated $NH_4Cl$ (100 ml), saturated sodium bicarbonate, and brine, dried, and concentrated to give the product (14.5 g, 100%). MS m/e 306 $(M+H)^+$ Step 5

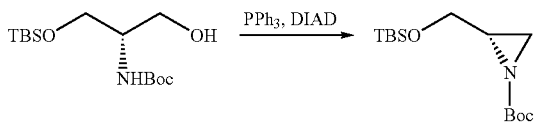

To an ice-cold solution of triphenylphosphine (13.95 g, 53.19 mmol) in THF (400 ml) and $CH_3CN$ (50 ml) was added DIAD (10.76 g, 53.21 mmol). The mixture was stirred for 15 min and a solution of the product of Step 4 (8.20 g, 26.2 mmol) in THF (100 ml) was added over 15 min. After the addition was complete, the ice-water bath was removed and the mixture was stirred at RT for 2 d. The mixture was concentrated and purified by column chromatography (gradient EtOAc/Hexanes 0-5%) to give the product (3.75 g, 50%). MS m/e 288 $(M+H)^+$ Step 6

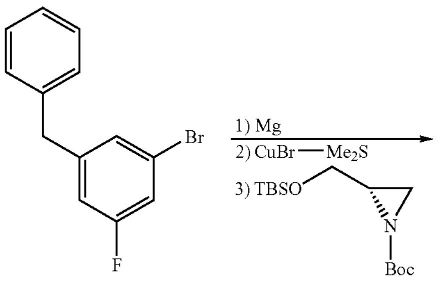

-continued

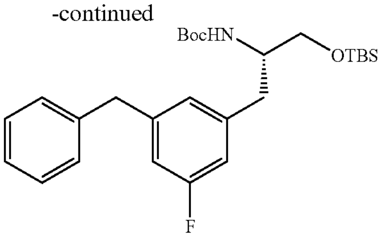

To a flame-dried flask were added magnesium turnings (499 mg, 20.5 mmol), the product of Step 2 (4.45 g, 16.8 mmol), drops of 1,2-dibromoethane, and anhydrous THF (20 ml). The mixture was stirred at RT for 1.5 h and added to a suspension of CuBr-$Me_2S$ (272 mg, 1.32 mmol) in THF (15 ml) in a dry ice-acetone bath. The mixture was stirred for 1.5 h and a solution of the product of Step 5 (2.52 g, 8.75 mmol) in anhydrous ether (20 ml) was added. The resulting mixture was warmed in an ice-water bath and allowed to slowly warm to RT and stirred for 3 d. The reaction was quenched with saturated $NH_4Cl$ (100 ml) and extracted with EtOAc (2×150 ml). The combined organic layer was dried ($MgSO_4$), concentrated, and purified by column chromatography (gradient EtOAc/Hexanes 0-8%) to give the product (1.51 g, 36%). MS m/e 474 $(M+H)^+$ Step 7

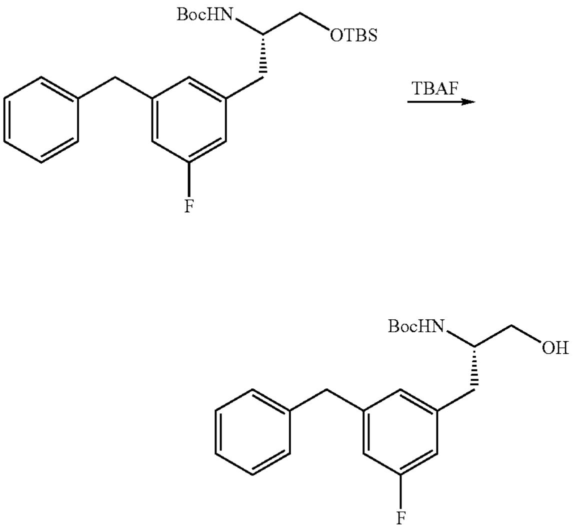

A mixture of the product of Step 6 (710 mg, 1.50 mmol) and 1M TBAF in THF (2.8 ml) in THF (10 ml) was stirred at RT for 5 h. The mixture was diluted with EtOAc (50 ml) and extracted with water (50 ml). The organic layer was dried ($MgSO_4$), concentrated, and purified by column chromatography (gradient MeOH/$CH_2Cl_2$ 0-2.5%) to give the product (508 mg, 94%). MS m/e 382 $(M+Na)^+$ Step 8

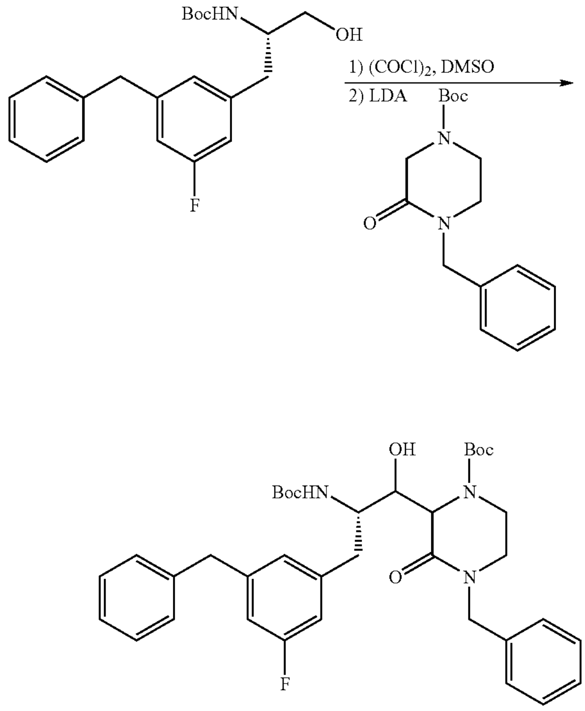

To a solution of oxalyl chloride (214 mg, 1.65 mmol) in $CH_2Cl_2$ (2.5 ml) in a dry ice-acetone bath was added DMSO (356 mg, 4.56 mmol). After 5 min, a solution of the product of Step 7 (508 mg, 1.41 mmol) in $CH_2Cl_2$ (3.5 ml) was added and the mixture was stirred for 1 h. Triethylamine (700 μl, 5.02 mmol) was added and the mixture was stirred for 15 min. The mixture was warmed to RT and stirred for 15 min. Water (30 ml) and $CH_2Cl_2$ (40 ml) were added and the aqueous layer was extracted with $CH_2Cl_2$ (30 ml). The combined organic layer was washed with brine (50 ml), dried ($MgSO_4$), and concentrated to give the aldehyde, which was not further purified.

To a solution of diisopropylamine (188 mg, 1.86 mmol) in THF (2.5 ml) in a dry ice-acetone bath was added 1.6 M butyllithium in hexanes (1.40 ml, 2.24 mmol). After 5 min the mixture was put in an ice-water bath and stirred for 20 min. The solution was cooled in the dry ice-acetone bath again and a solution of the product of Preparative Example 1, Step 5 (460 mg, 1.59 mmol) in THF (4 ml) was added. The mixture was stirred for 1 h. A solution of the above aldehyde in THF (4 ml) was added and the mixture was stirred for 1.5 h. The reaction was quenched with water (40 ml) and extracted with ether (50 ml). The aqueous layer was extracted with ether (3×40 ml). The combined organic layer was washed with brine (50 ml), dried ($MgSO_4$), concentrated, and purified by PTLC (40% EtOAc/Hexanes) to give: fraction 1 (137 mg, 15%). MS m/e 648 $(M+H)^+$; fraction 2 (148 mg, 16%). MS m/e 648 $(M+H)^+$ Step 9

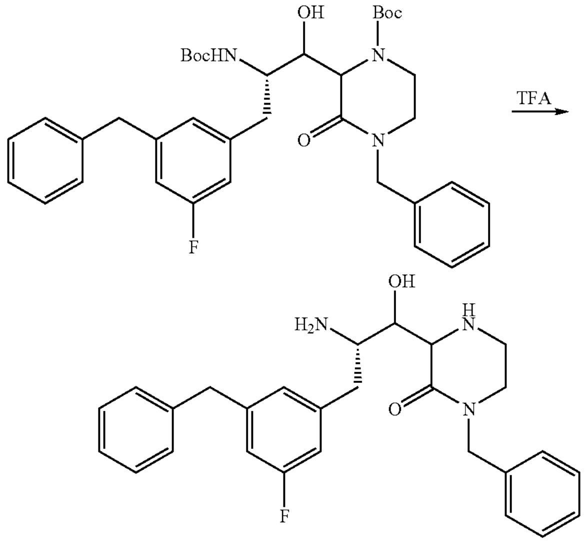

A solution of the fraction 1 product of Step 8 (136 mg, 0.211 mmol) and TFA (1 ml) in $CH_2Cl_2$ (5 ml) was stirred in an ice-water bath for 30 min then at RT for 2.5 h. The mixture was diluted with $CH_2Cl_2$ (40 ml) and washed with aqueous $NH_4OH$ (10 ml). The organic layer was dried ($Na_2CO_3$), concentrated, and purified by PTLC (10% 2M $NH_3$/MeOH-90% $CH_2Cl_2$) to give the product (72 mg, 77%). MS m/e 448 $(M+H)^+$ Step 10

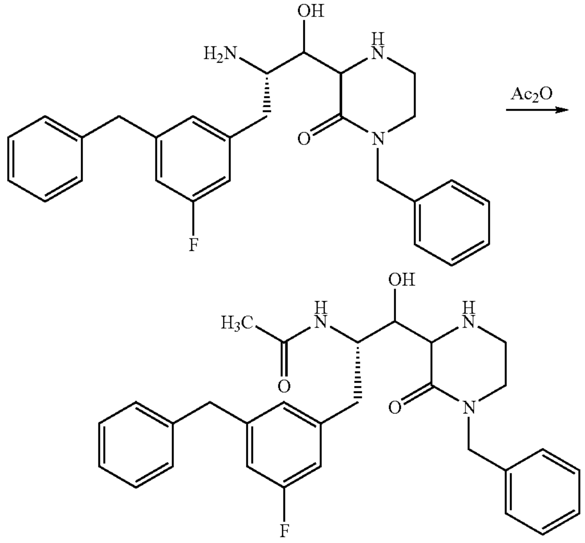

To an ice-cold solution of the product of Step 9 (70 mg, 0.16 mmol) and triethylamine (16 mg, 0.16 mmol) in $CH_2Cl_2$ (3 ml) was added acetic anhydride (14 mg, 0.14 mmol) in $CH_2Cl_2$ (3 ml) over 1 h. The mixture was slowly warmed to RT and stirred for 2 h. The solution was diluted with $CH_2Cl_2$ (40 ml) and washed with 0.5N NaOH (30 ml). The organic layer was dried ($MgSO_4$), concentrated, and purified by PTLC (5% MeOH/$CH_2Cl_2$) to give:

fraction A (24 mg, 36%). $^1$H-NMR ($CDCl_3$): δ=7.15-7.35 (m, 9H), 6.86 (s, 1H), 6.79 (d, 1H, J=9.6 Hz), 6.72 (d, 1H, J=9.6 Hz), 6.17 (s, 1H), 5.92 (d, 1H, J=10.4 Hz), 4.79 (d, 1H, J=15 Hz), 4.41 (m, 1H), 4.35 (d, 1H, J=15 Hz), 3.92 (s, 2H), 3.76 (d, 1H, J=9 Hz), 3.47 (s, 2H), 3.36 (m, 1H), 3.20 (d, 1H, J=9 Hz), 3.05 (m, 2H), 2.90 (m, 3H), 1.89 (s, 3H). MS m/e 490 $(M+H)^+$ fraction B (29 mg, 43%). $^1$H-NMR ($CDCl_3$): δ=7.15-7.35 (m, 10H), 6.89 (s, 1H), 6.84 (d, 1H, J=9.6 Hz), 6.73 (d, 1H, J=9.6 Hz), 6.08 (d, 1H, J=9.2 Hz), 4.73 (d, 1H, J=14.6 Hz), 4.42 (m, 1H), 4.36 (d, 1H, J=14.6 Hz), 4.03 (m, 1H), 3.91 (s, 2H), 3.37 (d, 1H, J=7.6 Hz), 3.25 (m, 1H), 3.00 (m, 3H), 2.79 (m, 1H), 2.66 (m, 1H), 1.80 (s, 3H). MS m/e 490 $(M+H)^+$ By essentially the same procedure set forth in Step 9 and Step 10, the following examples were prepared from fraction 2 product of Step 8:

fraction C (27 mg) MS m/e 490 $(M+H)^+$ fraction D (28 mg) MS m/e 490 $(M+H)^+$

PREPARATIVE EXAMPLE 3

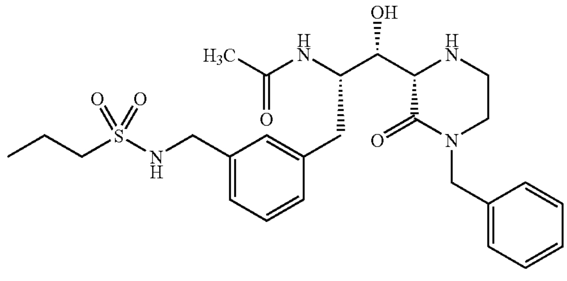

Step 1

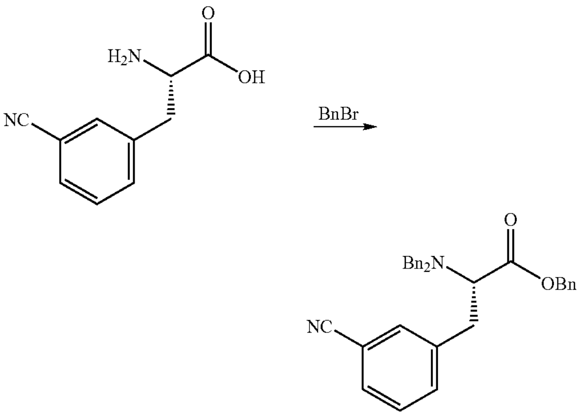

A solution of (S)-m-cyanophenylalanine (5.00 g, 26.3 mmol) and potassium carbonate (14.5 g, 105 mmol) in water (50 ml) was heated to reflux. Benzyl bromide (10.4 ml, 86.8 mmol) was added dropwise. After 1 h additional benzyl bromide (1.50 ml, 12.5 mmol) was added and the mixture was refluxed for 1 h. The mixture was cooled and extracted with ether (2×300 ml). The combined organic layer was washed with saturated $NaHCO_3$ (100 ml) and brine, dried ($MgSO_4$), concentrated, and purified by column chromatography (gradient EtOAc/Hexanes 0-10%) to give the product (10.9 g, 90%). MS m/e 461 $(M+H)^+$ Step 2

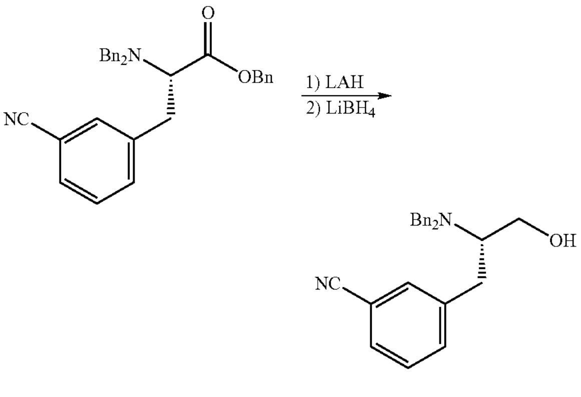

To a solution of the product of Step 1 (2.30 g, 4.99 mmol) in THF (25 ml) in a dry ice-acetone bath was added 1M $LiAlH_4$ in THF (10.0 ml) slowly and the mixture was stirred for 3.5 h. The reaction was quenched with saturated $NH_4Cl$ (15 ml) and extracted with ether (2×100 ml). The combined organic layer was washed with brine, dried ($MgSO_4$), and concentrated. The residue was dissolved in THF (300 ml) and 2M $LiBH_4$ in THF (2 ml) was added. The mixture was stirred at RT for 18 h. The reaction was quenched with saturated $NH_4Cl$ (10 ml) and extracted with ether (2×100 ml). The combined organic layer was washed with brine, dried ($MgSO_4$), concentrated, and purified by column chromatography (gradient EtOAc/Hexanes 0-40%) to give the product (1.26 g, 71%). MS m/e 357 $(M+H)^+$ Step 3

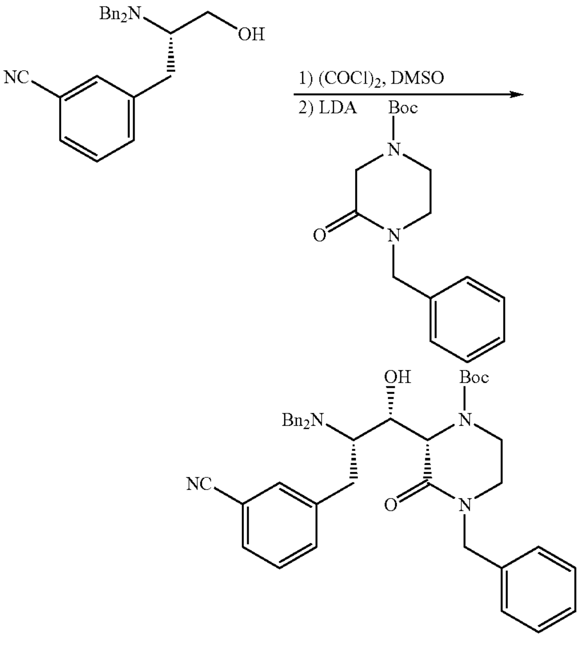

To a solution of oxalyl chloride (538 mg, 4.24 mmol) in $CH_2Cl_2$ (6 ml) in a dry ice-acetone bath was added DMSO (662 mg, 8.48 mmol). After 5 min, a solution of the product of Step 2 (1.26 g, 3.53 mmol) in $CH_2Cl_2$ (15 ml) was added and the mixture was stirred for 1 h. Triethylamine (1.71 g, 17.0 mmol) was added and the mixture was warmed to RT and stirred for 30 min. Water (30 ml) and $CH_2Cl_2$ (50 ml) were added and the aqueous layer was extracted with $CH_2Cl_2$ (2×100 ml). The combined organic layer was washed with water (50 ml) and brine, dried ($MgSO_4$), and concentrated to give the aldehyde, which was not further purified.

To a solution of diisopropylamine (472 mg, 4.67 mmol) in THF (3 ml) in a dry ice-acetone bath was added 1.6 M butyllithium in hexanes (2.92 ml, 4.67 mmol). After 5 min the mixture was put in an ice-water bath and stirred for 20 min. The solution was cooled in the dry ice-acetone bath again and a solution of the product of Preparative Example 1, Step 5 (1.23 g, 4.24 mmol) in THF (10 ml) was added. The mixture was stirred for 1 h. A solution of the above aldehyde in THF (15 ml) was added and the mixture was stirred for 1 h. The reaction was quenched with saturated $NH_4Cl$ (10 ml) and diluted with water (20 ml) and ether (100 ml). The aqueous layer was extracted with ether (2×50 ml). The combined organic layer was washed with 5% citric acid (50 ml), saturated $NaHCO_3$ (50 ml), and brine (50 ml), dried ($MgSO_4$), concentrated, and purified by column chromatography (gradient EtOAc/Hexanes 0-40%) to give the product (820 mg, 36%). MS m/e 645 $(M+H)^+$ Step 4

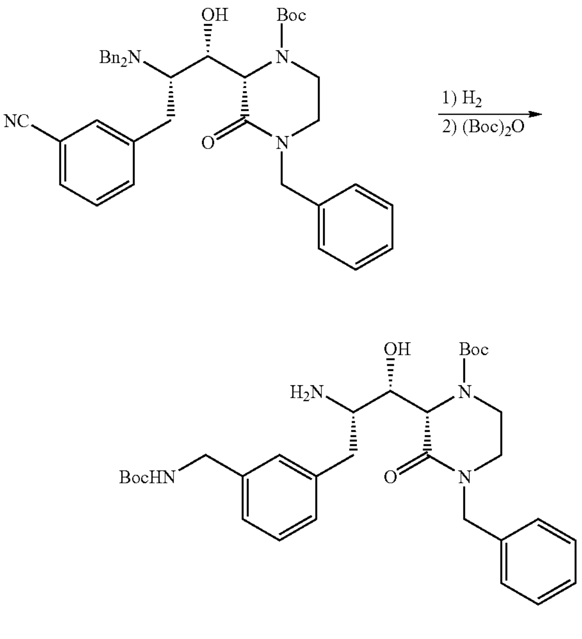

A mixture of the product of Step 3 (64 mg, 0.10 mmol), 20% $Pd(OH)_2/C$ (40 mg), and formic acid (0.1 ml) in EtOH (3 ml) was stirred under $H_2$ (1 atm) for 40 min. The mixture was filtered and concentrated. The residue and triethylamine (36 μl, 0.25 mmol) were dissolved in $CH_2Cl_2$ (5 ml) and cooled in an ice-water bath. To the solution was added a solution of $(Boc)_2O$ (24 mg, 0.11 mmol) in $CH_2Cl_2$ (1 ml) dropwise. The mixture was stirred in the ice-water bath for 1 h and concentrated. The residue was purified by PTLC (5% 2M $NH^3$/MeOH-95% $CH_2Cl_2$) to give the product (62 mg, 100%). MS m/e 569 $(M+H)^+$ Step 5

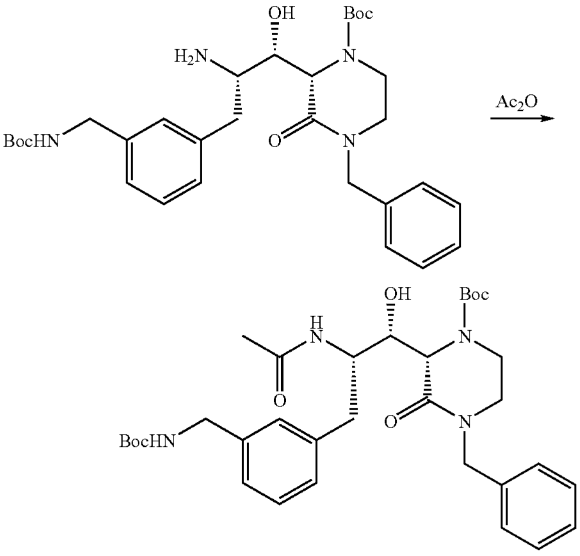

A solution of the product of Step 4 (62 mg, 0.11 mmol), acetic anhydride (12 mg, 0.12 mmol), and triethylamine (36 μl, 0.25 mmol) in $CH_2Cl_2$ (4 ml) was stirred in an ice-water bath for 30 min. The mixture was concentrated and purified by PTLC (5% MeOH/$CH_2Cl_2$) to give the product (51 mg, 76%). MS m/e 611 $(M+H)^+$ Step 6

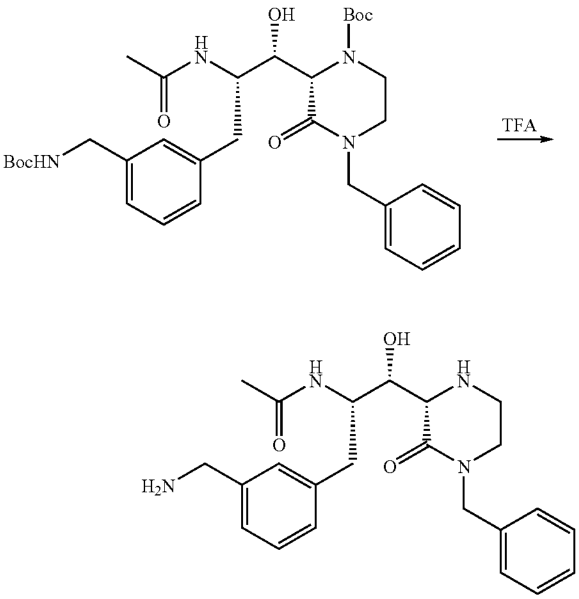

A solution of the product of Step 5 (51 mg, 0.084 mmol) and TFA (1 ml) in $CH_2Cl_2$ (4 ml) was stirred at RT for 30 min and concentrated. The residue was dissolved in $CH_2Cl_2$ (50 ml) and washed with aqueous $NH_4OH$ (5 ml) and brine. The organic layer was dried ($K_2CO_3$) and concentrated to give the product (34 mg, 99%). MS m/e 411 $(M+H)^+$ Step 7

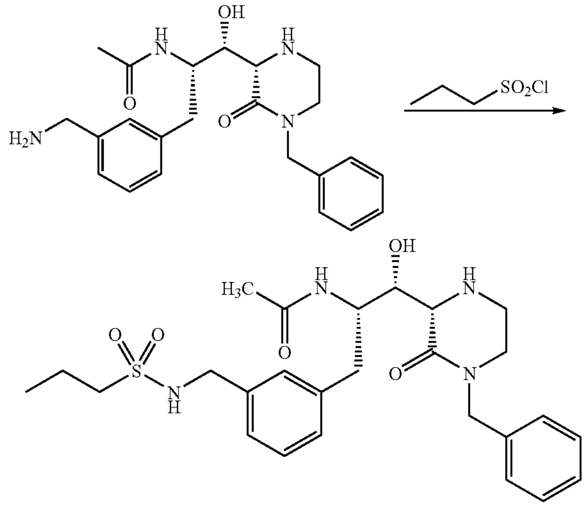

To an ice-cold solution of the product of Step 6 (32 mg, 0.078 mmol) and triethylamine (28 μl, 0.20 mmol) in $CH_2Cl_2$ (2.5 ml) was added a solution of propylsulfonyl chloride (9.6 μl, 0.086 mmol) in $CH_2Cl_2$ (0.5 ml). The mixture was stirred for 30 min and concentrated. The residue was purified by PTLC (5% 2M $NH_3$/MeOH-95% $CH_2Cl_2$) to give the product (27 mg, 66%). $^1$H-NMR ($CDCl_3$): δ=7.05-7.35 (m, 9H), 6.48 (d, 1H, J=9.2 Hz), 5.52 (m, 1H), 4.71 (d, 1H, J=14.6 Hz), 4.47 (m, 1H), 4.29 (d, 1H, J=14.6 Hz), 4.17 (m, 2H), 4.02 (m, 1H), 3.44 (m, 1H), 3.25 (m, 1H), 3.06 (m, 3H), 2.84 (m, 4H), 1.75 (m, 5H), 0.93 (t, 3H, J=7.4 Hz). LCMS $t_R$=2.80 min m/e 517 $(M+H)^+$

PREPARATIVE EXAMPLE 4

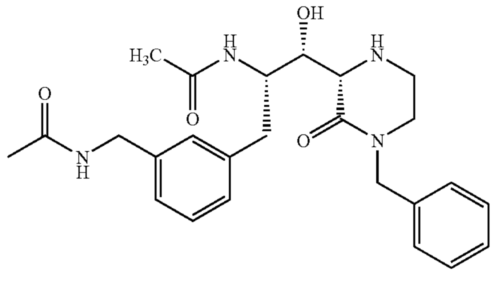

Step 1

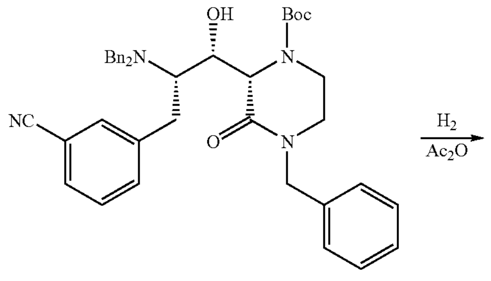

-continued

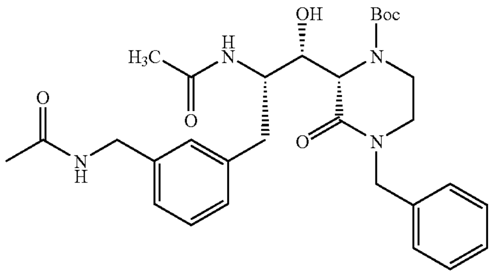

A mixture of the product of Preparative Example 3, Step 3 (64 mg, 0.10 mmol), acetic anhydride (29 μl, 0.30 mmol), acetic acid (0.1 ml), and 20% $Pd(OH)_2/C$ (64 mg) in EtOH (3 ml) was stirred under $H_2$ (1 atm) for 1.5 h. The mixture was concentrated and the residue was dissolved in $CH_2Cl_2$ (30 ml). The solution was extracted with aqueous $NH_4OH$ and brine, dried ($MgSO_4$), concentrated, and purified by PTLC (5% MeOH/$CH_2Cl_2$) to give the product (14 mg, 25%). MS m/e 553 $(M+H)^+$ Step 2

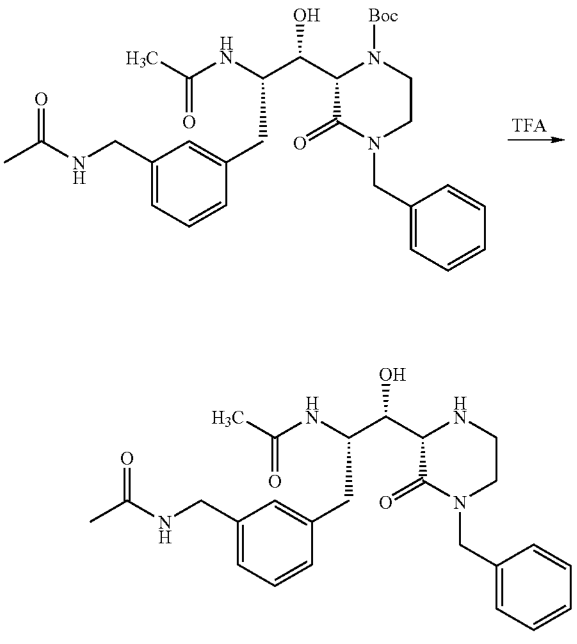

A solution of the product of Step 1 (14 mg, 0.025 mmol) and TFA (1 ml) in $CH_2Cl_2$ (4 ml) was stirred at RT for 1.5 h. The mixture was concentrated and purified by PTLC (5% 2M $NH_3$/MeOH-95% $CH_2Cl_2$) to give the product (8 mg, 74%). $^1$H-NMR ($CDCl_3$): δ=7.0-7.35 (m, 9H), 6.11 (m, 1H), 6.01 (b, 1H), 5.15 (m, 1H), 4.67 (d, 1H, J=14.8 Hz), 4.47 (m, 1H), 4.33 (m, 3H), 3.99 (m, 1H), 3.38 (m, 1H), 3.26 (m, 1H), 3.01 (m, 3H), 2.80 (m, 2H), 1.98 (s, 3H), 1.77 (s, 3H). LCMS $t_R$=2.30 min m/e 453 $(M+H)^+$

PREPARATIVE EXAMPLE 5

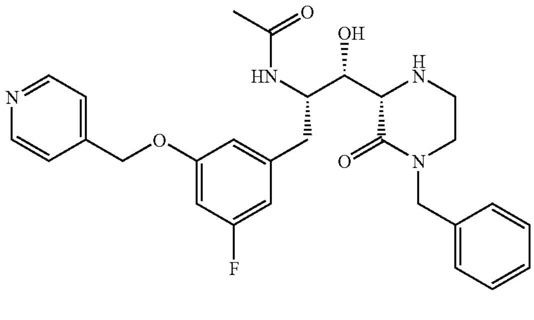

Step 1

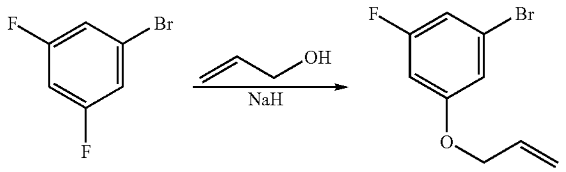

To a suspension of 60% NaH (6.40 g, 0.160 mol) in anhydrous DMA (400 ml) was added allyl alcohol (8.90 g, 0.154 mol) slowly. The mixture was stirred at RT for 1 h. 3,5-Difluorobromobenzene (30.0 g, 0.155 mol) was added and the mixture was stirred at RT for 24 h. The reaction was quenched with water (1.5 l) and extracted with ether (4×300 ml). The combined organic layer was washed with brine (500 ml), dried ($MgSO_4$), concentrated, and purified by column chromatography (Hexanes) to give the product (14.3 g, 40%). $^1$H-NMR ($CDCl_3$): δ=6.81 (m, 2H), 6.53 (m, 1H), 5.96 (m, 1H), 5.34 (m, 2H), 4.46 (m, 2H).

Step 2

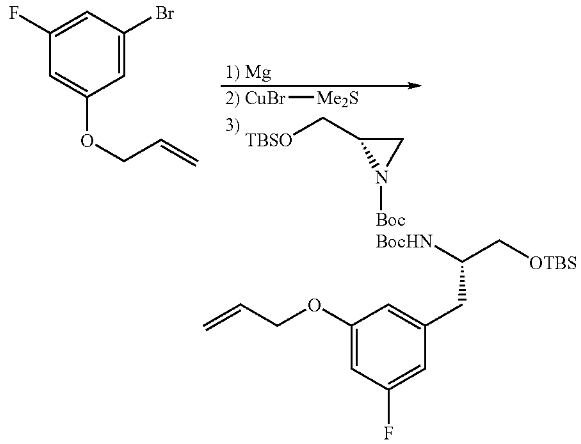

To a flame-dried flask was added magnesium turnings (292 mg, 12.0 mmol) followed by one third of a solution of the product of Step 1 (2.31 g, 10.0 mmol) in THF (16 ml). The reaction was initiated with 1,2-dibromoethane (50 μl) then the remaining solution of the product of Step 1 was added slowly. The mixture was stirred at RT for min and added to a suspension of CuBr-$Me_2S$ (310 mg, 1.51 mmol) in THF (30 ml) at −40° C. The mixture was stirred at 4° C. for 30 min and a solution of the product of Preparative Example 2, Step 5 (1.20 g, 4.17 mmol) in anhydrous ether (15 ml) was added. The resulting mixture was stirred at 4° C. for 1 h then at RT for 3 d. The reaction was quenched with saturated $NH_4Cl$ (100 ml) and extracted with EtOAc (2×150 ml). The combined organic layer was washed with saturated sodium bicarbonate and brine, dried ($MgSO_4$), concentrated, and purified by column chromatography (gradient EtOAc/Hexanes 0-5%) to give the product (1.00 g, 55%). MS m/e 440 $(M+H)^+$ Step 3

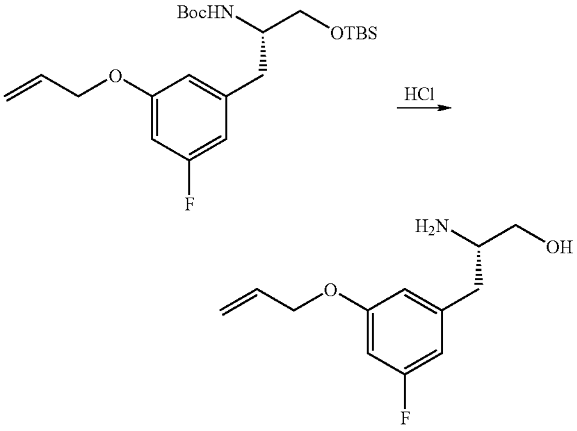

A solution of the product of Step 2 (500 mg, 1.14 mmol) in $CH_2Cl_2$ (12 ml) and 4N HCl/dioxane (6 ml) was stirred at RT for 20 h. The mixture was concentrated and the residue was partitioned between $CH_2Cl_2$ (50 ml) and 5N $NH_4OH$ (20 ml). The organic layer was dried ($K_2CO_3$) and concentrated to give the product (345 mg, 100%). MS m/e 226 $(M+H)^+$ Step 4

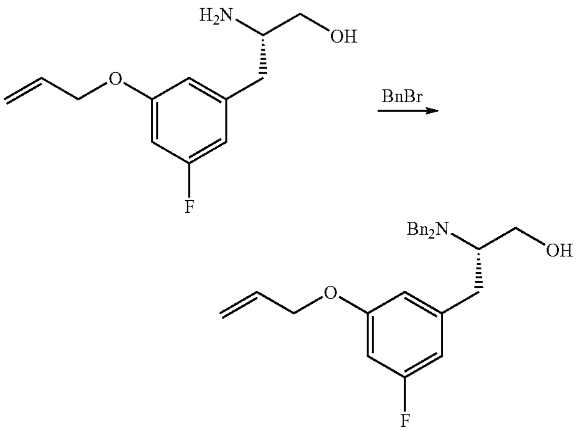

A solution of the product of Step 3 (3.10 g, 13.0 mmol) and potassium carbonate (5.39 g, 39.0 mmol) in EtOH (30 ml) and water (90 ml) was heated to 70° C. Benzyl bromide (3.42 ml, 28.6 mmol) was added and the mixture was stirred at 70° C. for 2.5 h. EtOH was removed and the residue was extracted with ether (2×200 ml). The organic layer was washed with brine, dried ($K_2CO_3$), concentrated, and purified by column chromatography (gradient 0-10% EtOAc/Hexanes) to give the product (4.40 g, 83%). MS m/e 406 $(M+H)^+$ Step 5

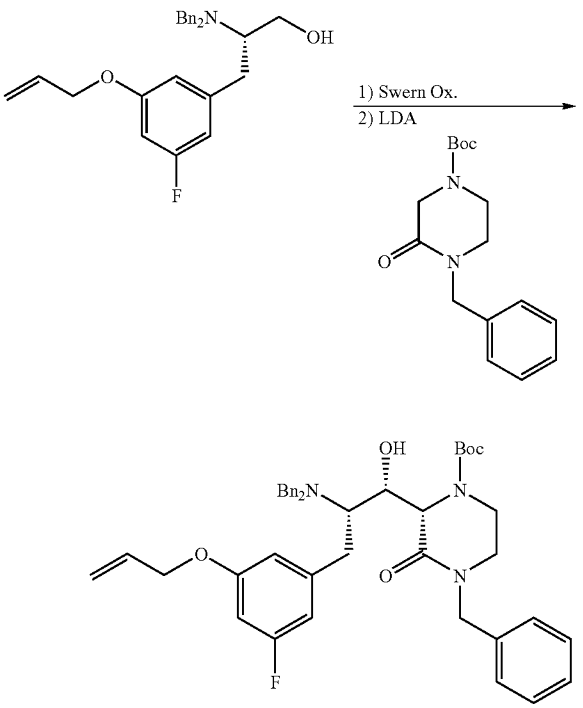

To a solution of oxalyl chloride (762 mg, 6.00 mmol) in $CH_2Cl_2$ (10 ml) in a dry ice-acetone bath was added DMSO (938 mg, 12.0 mmol). After 5 min, a solution of the product of Step 4 (2.03 g, 5.01 mmol) in $CH_2Cl_2$ (20 ml) was added and the mixture was stirred for 1 h. Triethylamine (2.42 g, 23.9 mmol) was added and after 2 min the cooling bath was removed. The mixture was stirred for 30 min and diluted with water (50 ml). $CH_2Cl_2$ (100 ml) was added and the aqueous layer was extracted with $CH_2Cl_2$ (2×100 ml). The combined organic layer was washed with brine, dried ($MgSO_4$), and concentrated to give the aldehyde, which was not further purified.

To a solution of diisopropylamine (667 mg, 6.59 mmol) in THF (5 ml) in a dry ice-acetone bath was added 1.6 M butyllithium in hexanes (4.13 ml, 6.61 mmol). After 5 min the mixture was put in an ice-water bath and stirred for 20 min. The solution was cooled in the dry ice-acetone bath again and a solution of the product of Preparative Example 1, Step 5 (1.74 g, 5.99 mmol) in THF (20 ml) was added. The mixture was stirred for 1 h. A solution of the above aldehyde in THF (30 ml) was added and the mixture was allowed to warm up to RT slowly and stirred for 16 h. The reaction was quenched with saturated $NH_4Cl$ (20 ml) and extracted with ether (3×100 ml). The combined organic layer was washed with 5% citric acid, saturated $NaHCO_3$, and brine, dried ($Na_2SO_4$), concentrated, and purified by column chromatography (gradient EtOAc/Hexanes 0-40%) to give the product (1.20 g, 35%). MS m/e 694 $(M+H)^+$ Step 6

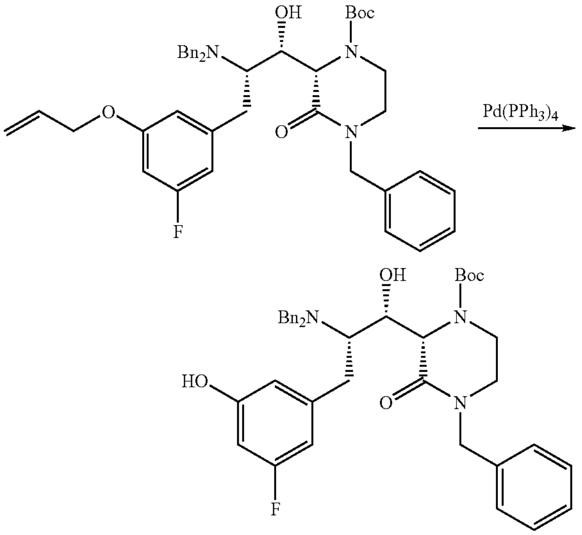

A solution of the product of Step 5 (280 mg, 0.404 mmol) in MeOH (5 ml) was degassed with $N_2$ for 5 min. $Pd(PPh_3)_4$ (70 mg, 0.061 mmol) was added and the mixture was degassed for another 5 min. Anhydrous potassium carbonate (166 mg, 1.20 mmol) was added and the mixture was stirred at RT for 18 h. The mixture was filtered and the filtrate was diluted with $CH_2Cl_2$ (100 ml), washed with 5% citric acid, saturated $NaHCO_3$ and brine. The organic layer was dried ($MgSO_4$), concentrated, and purified by column chromatography (gradient EtOAc/Hexanes 0-20%) to give the product (230 mg, 87%). MS m/e 654 $(M+H)^+$ Step 7

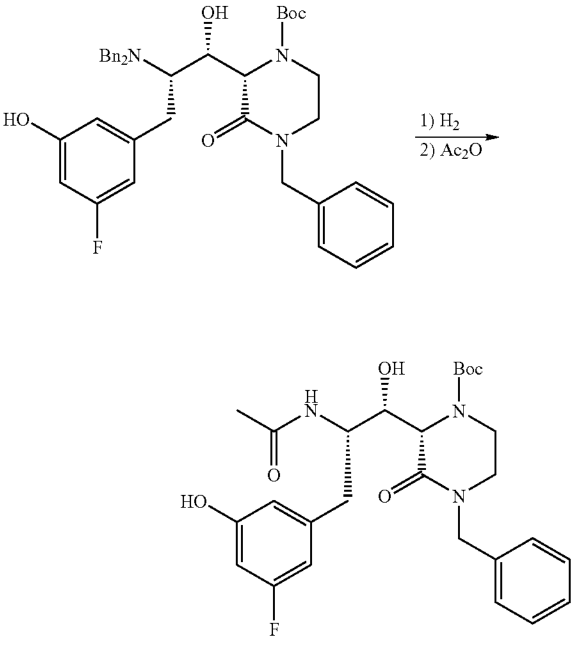

A mixture of the product of Step 6 (230 mg, 0.352 mmol), 20% $Pd(OH)_2/C$ (230 mg), and acetic acid (0.5 ml) in EtOH (12 ml) was stirred under $H_2$ (1 atm) for 16 h. The mixture was filtered, concentrated, and taken up in $CH_2Cl_2$ (20 ml). Acetic anhydride (36 mg, 0.35 mmol) and triethylamine (0.40 ml, 2.9 mmol) were added and the mixture was stirred in an ice-water bath for 1.5 h. The mixture was concentrated and purified by column chromatography (gradient MeOH/$CH_2Cl_2$ 0-5%) to give the product (148 mg, 82%). MS m/e 516 $(M+H)^+$ Step 8

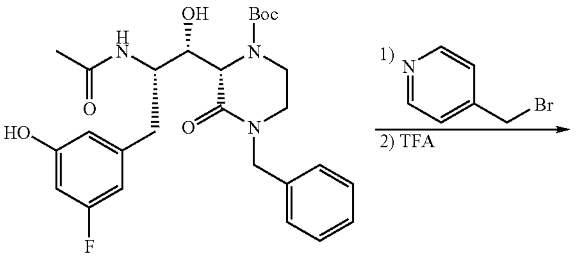

-continued

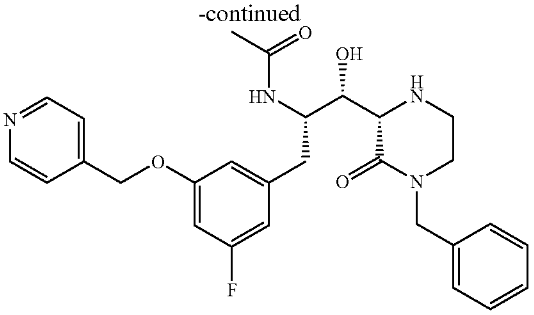

A mixture of the product of Step 7 (15 mg, 0.029 mmol), 4-bromomethyl pyridine (15 mg, 0.058 mmol), and potassium carbonate (40 mg, 0.29 mmol) in DMF (2.5 ml) was stirred at RT for 3 d. The mixture was diluted with $CH_2Cl_2$ (50 ml), extracted with water (3×50 ml) and saturated $NaHCO_3$, dried ($MgSO_4$), and concentrated. The residue was dissolved in $CH_2Cl_2$ (5 ml) and TFA (1 ml). The mixture was stirred at RT for 2.5 h, concentrated, and purified by PTLC (10% 2M $NH_3$/MeOH-90% $CH_2Cl_2$) to give the product (9 mg, 63%). $^1$H-NMR ($CDCl_3$): δ=8.57 (m, 2H), 7.15-7.35 (m, 7H), 6.67 (s, 1H), 6.58 (m, 1H), 6.48 (m, 1H), 6.02 (d, 1H, J=8.8 Hz), 5.07 (b, 1H), 5.01 (s, 2H), 4.68 (d, 1H, J=14.6 Hz), 4.42 (m, 1H), 4.36 (d, 1H, J=14.6 Hz), 3.99 (m, 1H), 3.37 (m, 1H), 3.27 (m, 1H), 3.03 (m, 3H), 2.76 (m, 2H), 1.82 (s, 3H), 1.69 (m, 2H). LCMS $t_R$=2.17 min m/e 507 $(M+H)^+$ By essentially the same procedure set forth in Preparative Example 5, the following examples were prepared.

| | LCMS $t_R$ (min) | $(M + H)^+$ |
|---|---|---|
| 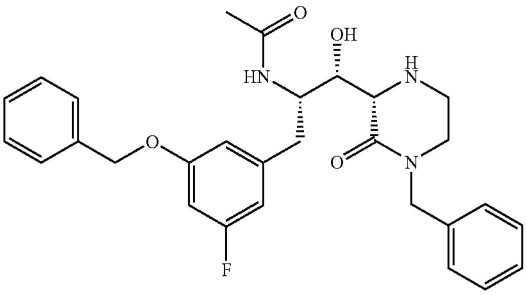 | 3.62 | 506 |
| 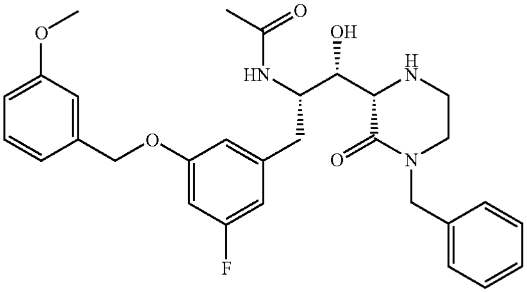 | 3.31 | 536 |

-continued
| | LCMS $t_R$ (min) | $(M+H)^+$ |
|---|---|---|
| 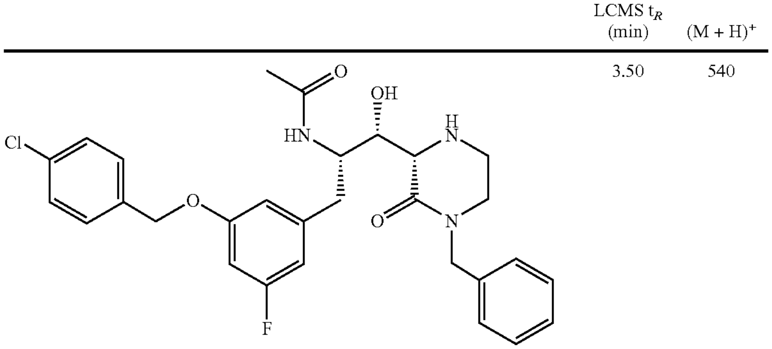 | 3.50 | 540 |
| 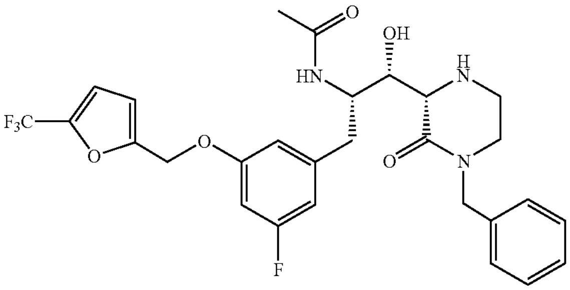 | 3.43 | 564 |
| 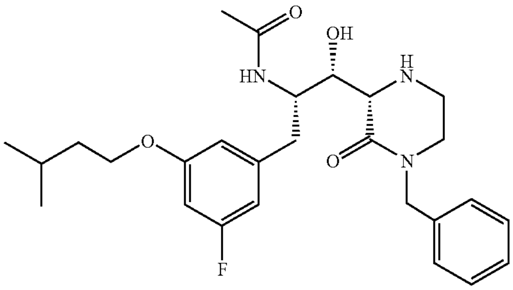 | 3.46 | 486 |
PREPARATIVE EXAMPLE 6
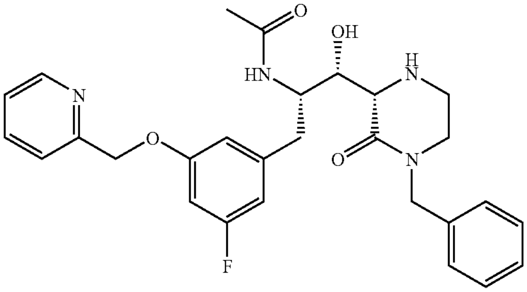
-continued
Step 1
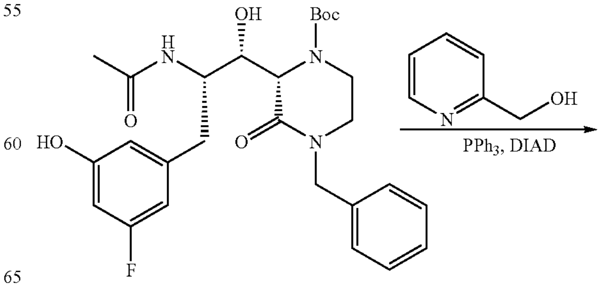

-continued

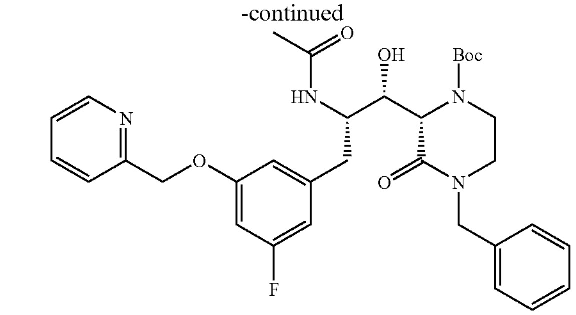

A mixture of the product of Preparative Example 5, Step 7 (15 mg, 0.029 mmol), 2-pyridylcarbinol (9.5 mg, 0.087 mmol), DIAD (18 mg, 0.087 mmol), and triphenylphosphine (23 mg, 0.087 mmol) in $CH_2Cl_2$ (1 ml) was stirred at RT for 24 h. The mixture was concentrated and purified by PTLC (5% MeOH/$CH_2Cl_2$) to give the product (20 mg, 100%). MS m/e 607 $(M+H)^+$ Step 2

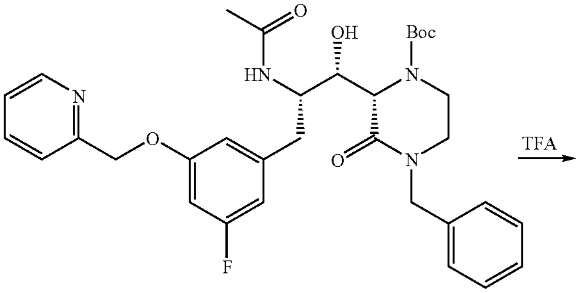

-continued

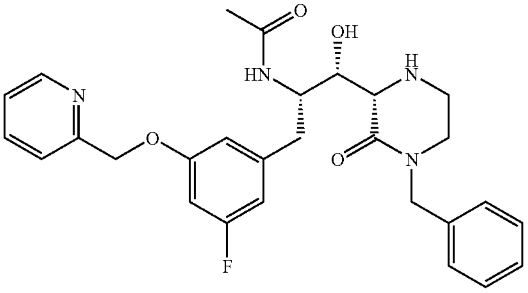

A solution of the product of Step 1 (20 mg, 0.029 mmol) and TFA (0.5 ml) in $CH_2Cl_2$ (3 ml) was stirred at RT for 2 h. The mixture was concentrated and purified by PTLC (5% 2M $NH_3$/MeOH-95% $CH_2Cl_2$) to give the product (8 mg, 57%). $^1$H-NMR ($CDCl_3$): δ=8.54 (m, 1H), 7.68 (m, 1H), 7.45 (m, 1H), 7.15-7.35 (m, 6H), 6.69 (s, 1H), 6.54 (m, 2H), 6.08 (d, 1H, J=8.8 Hz), 5.11 (s, 2H), 4.70 (d, 1H, J=14.6 Hz), 4.40 (m, 1H), 4.33 (d, 1H, J=14.6 Hz), 4.04 (m, 1H), 3.42 (d, 1H, J=7.6 Hz), 3.27 (m, 1H), 3.04 (m, 3H), 2.76 (m, 2H), 1.85 (m, 2H), 1.81 (s, 3H). LCMS $t_R$=2.25 min m/e 507 $(M+H)^+$ By essentially the same procedure set forth in Preparative Example 6, the following examples were prepared.

| | LCMS $t_R$ (min) | $(M + H)^+$ |
|---|---|---|
| 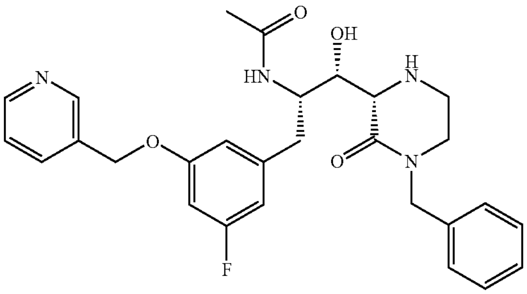 | 2.25 | 507 |
| 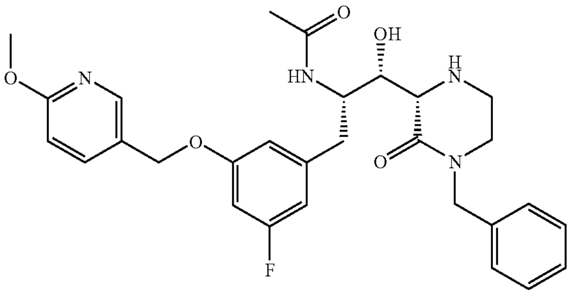 | 3.20 | 537 |

-continued
| | LCMS $t_R$ (min) | $(M + H)^+$ |
|---|---|---|
| 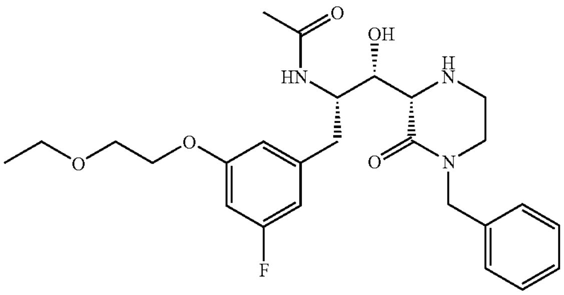 | 3.76 | 488 |
| 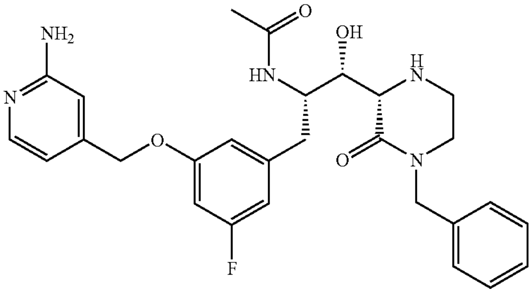 | 2.30 | 522 |
| 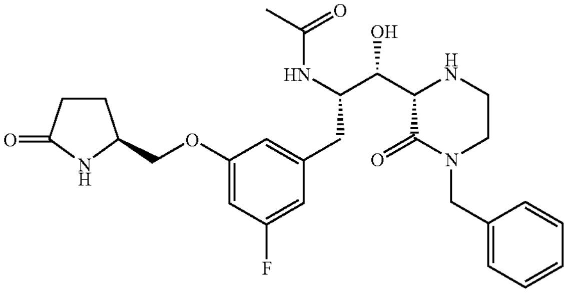 | 2.41 | 513 |
| 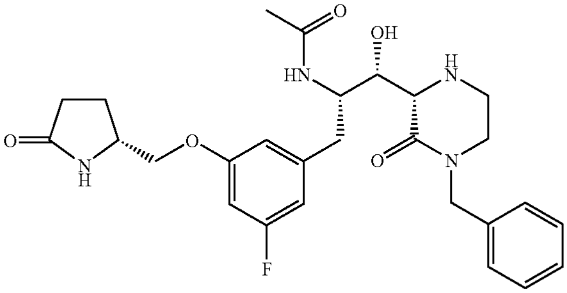 | 2.49 | 513 |
| 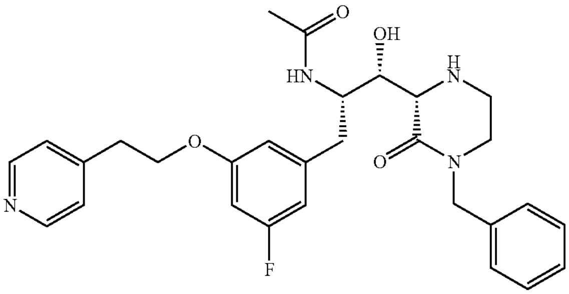 | 2.16 | 521 |

-continued
| | LCMS $t_R$ (min) | $(M+H)^+$ |
|---|---|---|
| 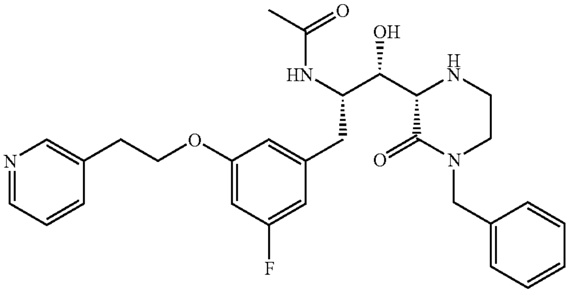 | 2.16 | 521 |
| 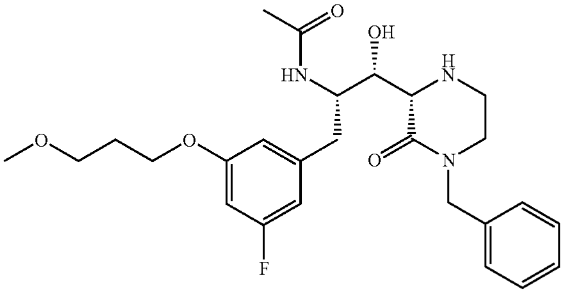 | 2.79 | 488 |
| 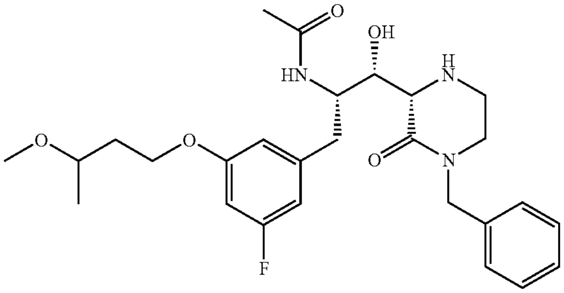 | 2.91 | 502 |
| 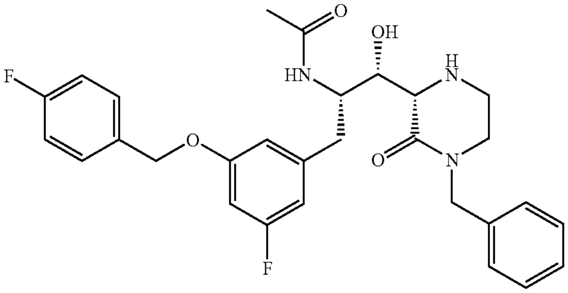 | 3.32 | 524 |
| 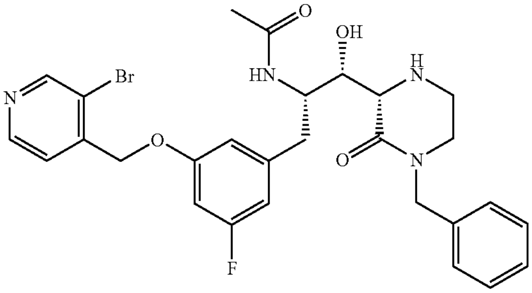 | 2.91 | 585 |

-continued
| | LCMS $t_R$ (min) | $(M + H)^+$ |
|---|---|---|
| 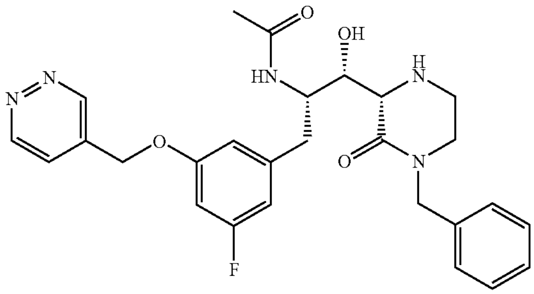 | 2.26 | 508 |
| 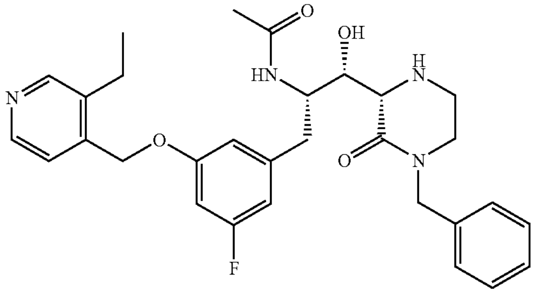 | 2.37 | 535 |
| 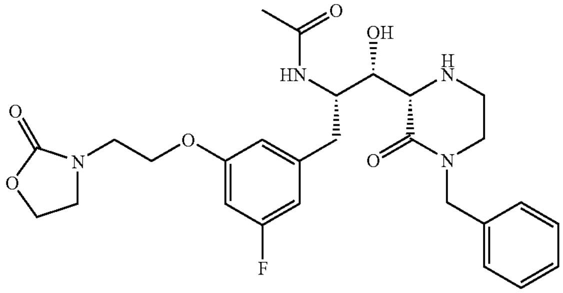 | 2.45 | 529 |
| 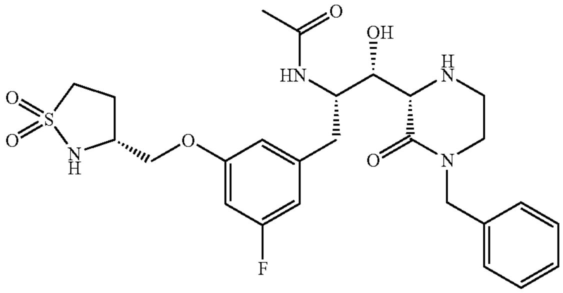 | 2.46 | 549 |

PREPARATIVE EXAMPLE 7

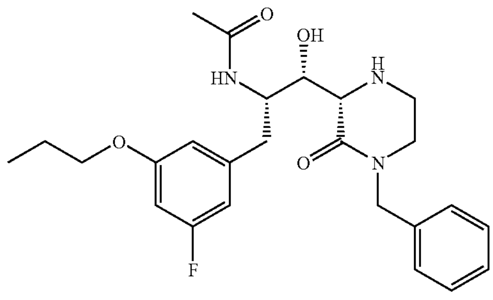

Step 1

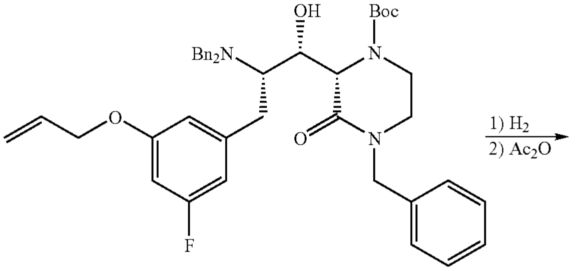

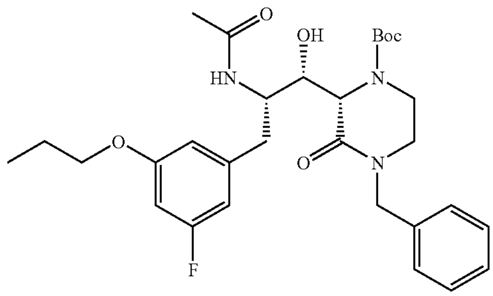

A mixture of the product of Preparative Example 5, Step 5 (140 mg, 0.202 mmol), acetic acid (0.2 ml), and 20% $Pd(OH)_2/C$ (90 mg) in EtOH (5 ml) was stirred under $H_2$ for 1.5 h. The mixture was filtered, concentrated, and dissolved in $CH_2Cl_2$ (5 ml). To this solution were added acetic anhydride (21 μl, 0.22 mmol) and triethylamine (100 μl, 0.717 mmol). The mixture was stirred at RT for 25 min. MeOH (1 ml) was added and the mixture was concentrated. The residue was purified by PTLC (5% $MeOH/CH_2Cl_2$) to give the product (75 mg, 67%). MS m/e 558 $(M+H)^+$ Step 2

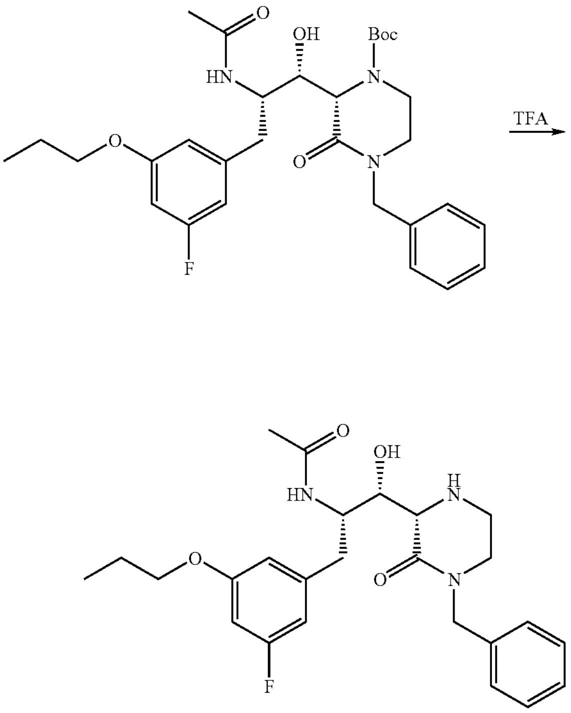

A solution of the product of Step 1 (75 mg, 0.13 mmol) and TFA (1 ml) in $CH_2Cl_2$ (5 ml) was stirred at RT for 30 min. The mixture was concentrated and purified by PTLC (5% 2M $NH_3$/MeOH-95% $CH_2Cl_2$) to give the product (67 mg, 100%). $^1$H-NMR ($CDCl_3$): δ=7.1-7.35 (m, 5H), 6.25-6.6 (m, 4H), 4.75 (m, 1H), 4.44 (m, 1H), 4.32 (m, 1H), 4.11 (m, 1H), 3.84 (m, 2H), 3.49 (m, 1H), 3.29 (m, 1H), 3.06 (m, 3H), 2.78 (m, 2H), 1.83 (s, 3H), 1.73 (m, 2H), 1.00 (t, 3H, J=7.4 Hz). LCMS $t_R$=3.14 min m/e 458 $(M+H)^+$

PREPARATIVE EXAMPLE 8

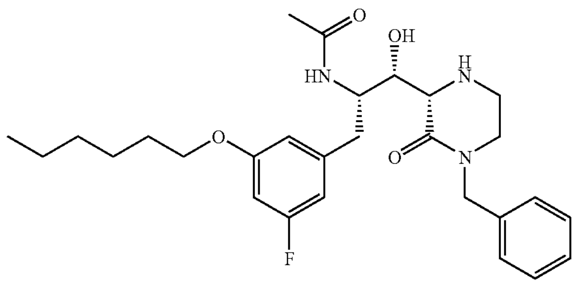

Step 1

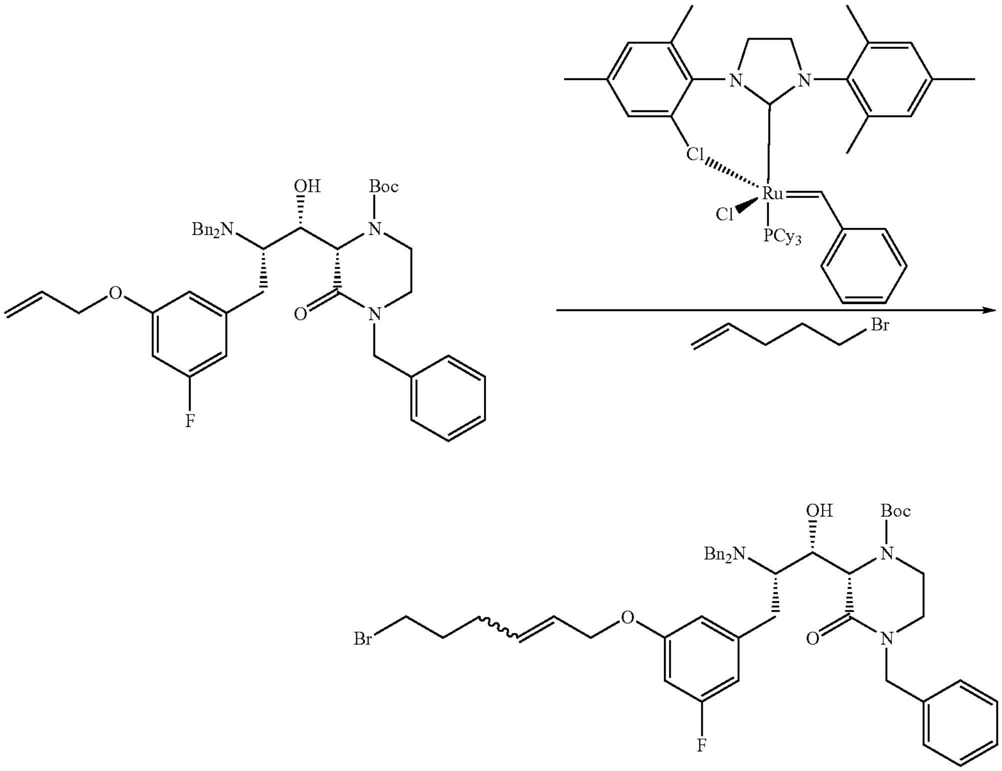

A mixture of the product of Preparative Example 5, Step 5 (69 mg, 0.099 mmol), 5-bromopentene (90 mg, 0.60 mmol), and 2nd generation Grubbs catalyst (19 mg, 0.022 mmol) in $CH_2Cl_2$ (5 ml) was degassed and heated to 50° C. for 6.5 h. The mixture was concentrated and purified by PTLC (5% $MeOH/CH_2Cl_2$) to give the product (60 mg, 74%). MS m/e 814 $(M+H)^+$ Step 2

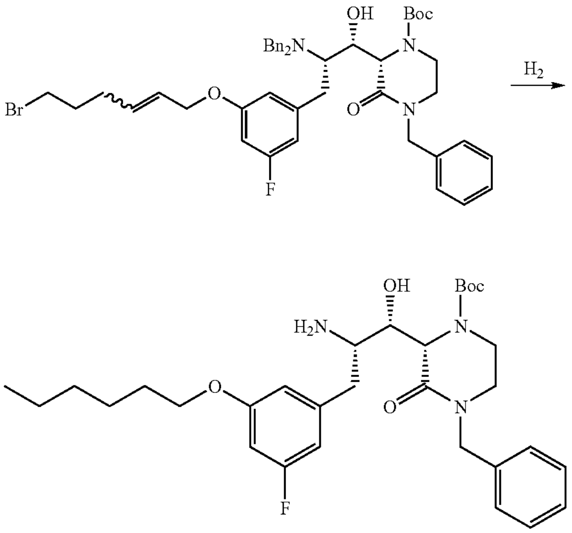

A mixture of the product of Step 1 (60 mg, 0.074 mmol), acetic acid (0.2 ml), and 20% $Pd(OH)_2/C$ (50 mg) in EtOH (3 ml) was stirred under $H_2$ for 2 h. The mixture was filtered and concentrated to give the product (39 mg, 95%). MS m/e 558 $(M+H)^+$ Step 3

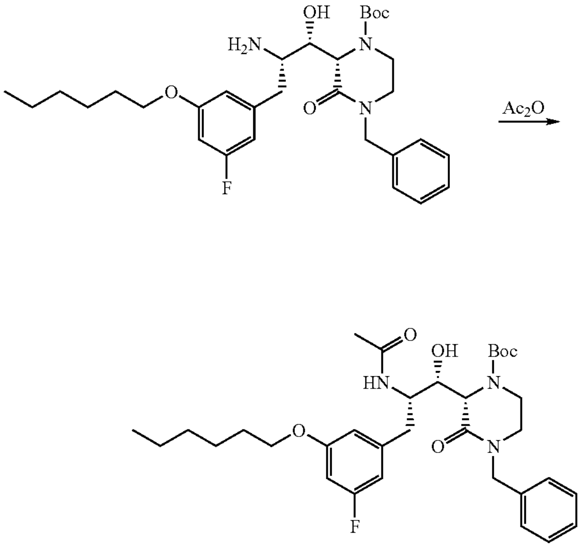

A solution of the product of Step 2 (39 mg, 0.070 mmol) and acetic anhydride (9 mg, 0.08 mmol) in $CH_2Cl_2$ (2.5 ml) was stirred at RT for 2.5 h. The mixture was concentrated and purified by PTLC (5% MeOH/$CH_2Cl_2$) to give the product (36 mg, 86%). MS m/e 600 $(M+H)^+$ Step 4

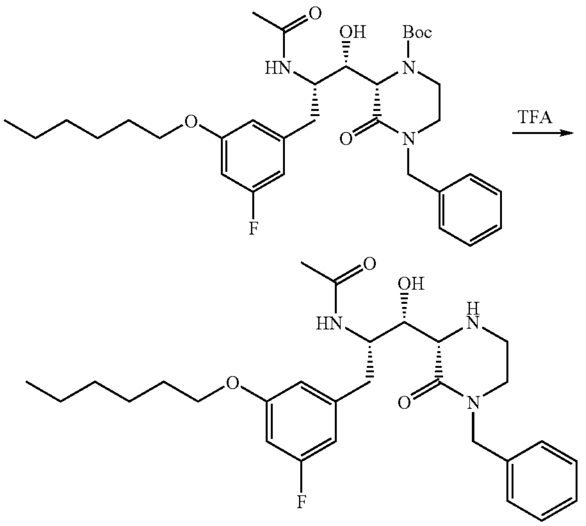

A solution of the product of Step 3 (36 mg, 0.060 mmol) and TFA (0.3 ml) in $CH_2Cl_2$ (2 ml) was stirred at RT for 1.5 h. The mixture was concentrated and purified by PTLC (5% 2M $NH_3$/MeOH-95% $CH_2Cl_2$) to give the product (19 mg, 62%). $^1$H-NMR ($CDCl_3$): δ=7.15-7.35 (m, 5H), 6.59 (s, 1H), 6.52 (m, 1H), 6.40 (m, 1H), 6.09 (d, 1H, J=9.2 Hz), 4.70 (d, 1H, J=14.8 Hz), 4.43 (m, 1H), 4.32 (d, 1H, J=14.8 Hz), 4.04 (m, 1H), 3.85 (m, 2H), 3.40 (m, 1H), 3.26 (m, 1H), 3.01 (m, 3H), 2.75 (m, 2H), 1.96 (b, 2H), 1.82 (s, 3H), 1.68 (m, 2H), 1.2-1.5 (m, 6H), 0.85 (m, 3H). LCMS $t_R$=3.69 min m/e 500 $(M+H)^+$ By essentially the same procedure set forth in Preparative Example 8, the following example was prepared.

| | LCMS $t_R$ (min) | $(M + H)^+$ |
|---|---|---|
| 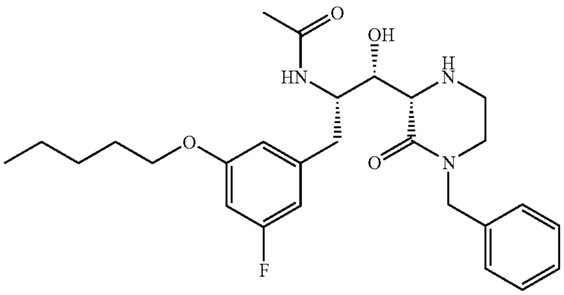 | 3.86 | 486 |

PREPARATIVE EXAMPLE 9

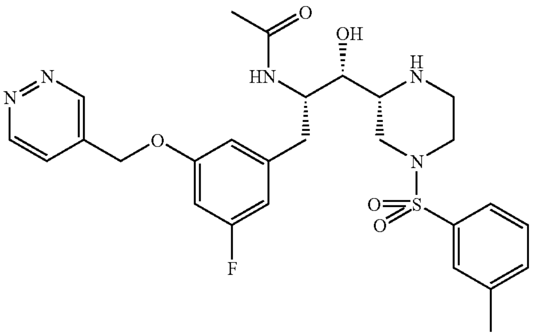

Step 1

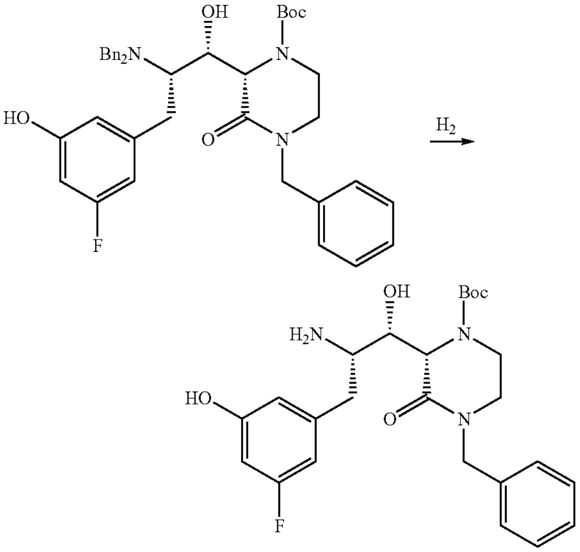

A mixture of the product of Preparative Example 5, Step 6 (1.50 g, 2.29 mmol), 20% $Pd(OH)_2$/C (0.70 g), and acetic acid (1 ml) in EtOH (50 ml) was stirred under $H_2$ (1 atm) for 4 h. The mixture was filtered and concentrated to give the product (1.04 g, 96%). MS m/e 474 $(M+H)^+$ Step 2

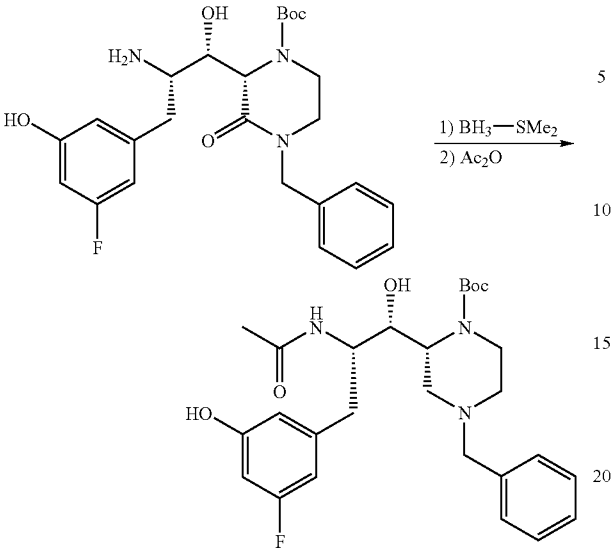

A mixture of the product of Step 1 (1.04 g, 2.20 mmol) and 2M $BH_3$—$SMe_2$ (8.0 ml) in THF (100 ml) was heated at 65° C. for 18 h. MeOH (10 ml) was added slowly and the heating continued for 1 h. The mixture was evaporated to dryness and the residue was dissolved in MeOH (50 ml). The resulting solution was concentrated and to the residue in $CH_2Cl_2$ (60 ml) were added $NEt_3$ (833 mg, 8.25 mmol) and acetic anhydride (281 mg, 2.75 mmol). The mixture was stirred at RT for 30 min and concentrated. 7N $NH_3$ in MeOH (50 ml) was added and the resulting solution was stirred for 1 h. The mixture was concentrated and purified by column chromatography (gradient MeOH/$CH_2Cl_2$ 0-3%) to give the product (680 mg, 62%). MS m/e 502 $(M+H)^+$ Step 3

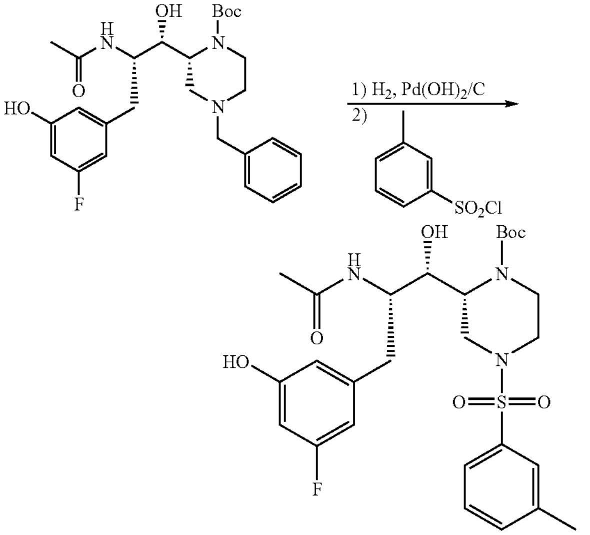

A mixture of the product of Step 2 (300 mg, 0.600 mmol), 20% $Pd(OH)_2/C$ (200 mg), and acetic acid (0.2 ml) in EtOH (15 ml) was stirred under $H_2$ (1 atm) for 1.25 h. The mixture was filtered and concentrated. The residue was dissolved in $CH_2Cl_2$ (20 ml) and cooled in an ice-water bath. Triethylamine (182 mg, 1.80 mmol) and m-toluenesulfonyl chloride (115 mg, 0603 mmol) were added. The mixture was stirred for 30 min, diluted with $CH_2Cl_2$ (150 ml), washed with 5% citric acid and saturated sodium bicarbonate, dried, and purified by column chromatography (gradient MeOH/$CH_2Cl_2$ 0-4%) to give the product (170 mg, 50%). MS m/e 566 $(M+H)^+$ Step 4

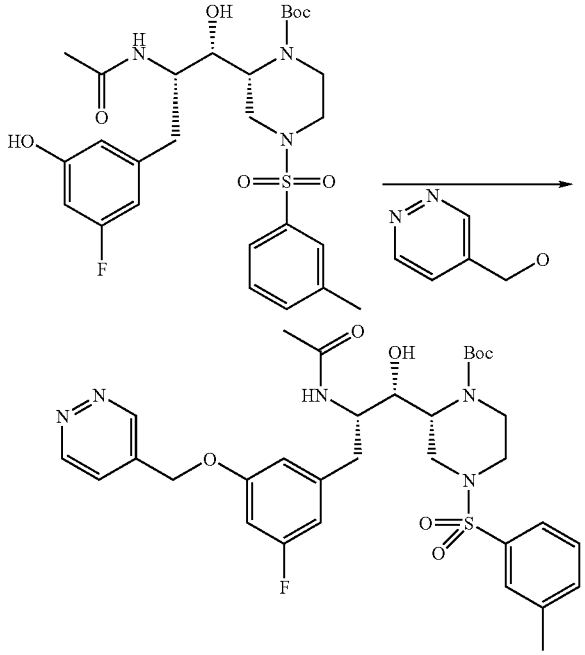

A solution of the product of Step 3 (28 mg, 0.050 mmol), pyridazinemethanol (17 mg, 0.15 mmol), triphenylphosphine (39 mg, 0.15 mmol), and DIAD (31 mg, 0.15 mmol) was stirred at RT for 1 h. The mixture was concentrated and purified by PTLC (5% MeOH/$CH_2Cl_2$) to give the product (32 mg, 97%). MS m/e 658 $(M+H)^+$ Step 5

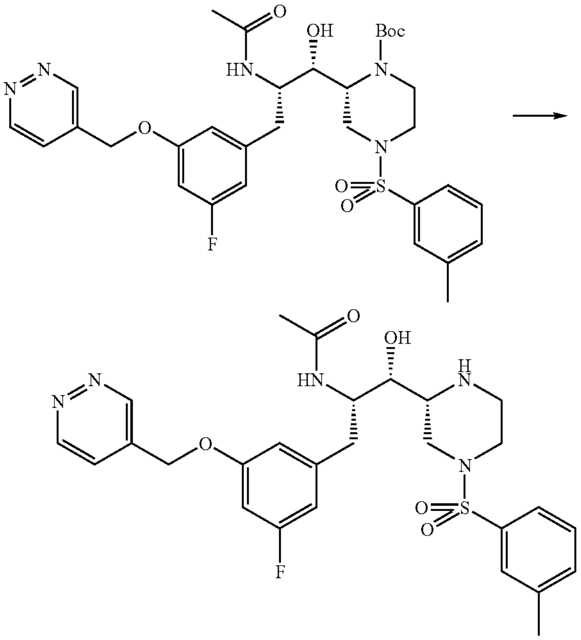

A solution of the product of Step 4 (32 mg, 0.048 mmol) and TFA (1 ml) in $CH_2Cl_2$ (5 ml) was stirred at RT for 1 h. The mixture was concentrated and purified by PTLC (5% 2M $NH_3$/MeOH in $CH_2Cl_2$) to give the product (21 mg, 77%). %). $^1$H-NMR ($CDCl_3$): δ=9.21 (s, 1H), 9.14 (m, 1H), 7.49 (m, 3H), 7.38 (m, 2H), 6.63 (s, 1H), 6.56 (m, 1H), 6.48 (m, 1H), 6.39 (m, 1H), 4.24 (m, 1H), 3.65 (m, 2H), 3.32 (m, 1H), 2.7-3.1 (m, 5H), 2.44 (m, 2H), 2.37 (s, 3H), 1.80 (s, 3H). LCMS $t_R$=2.62 min m/e 558 $(M+H)^+$ By essentially the same procedure set forth in Preparative Example 9, the following examples were prepared.

| | LCMS $t_R$ (min) | $(M + H)^+$ |
|---|---|---|
| 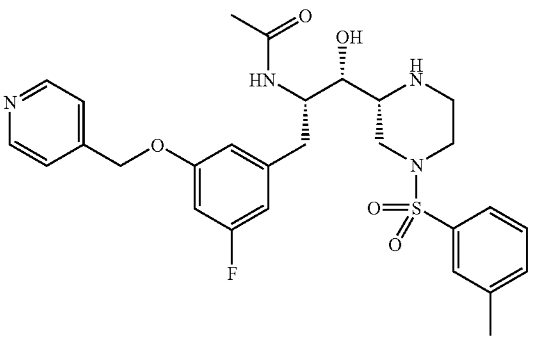 | 2.37 | 557 |
| 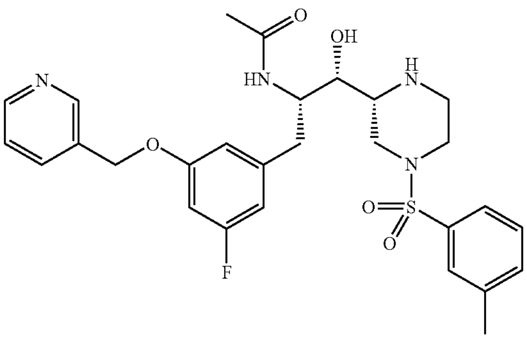 | 2.37 | 557 |
| 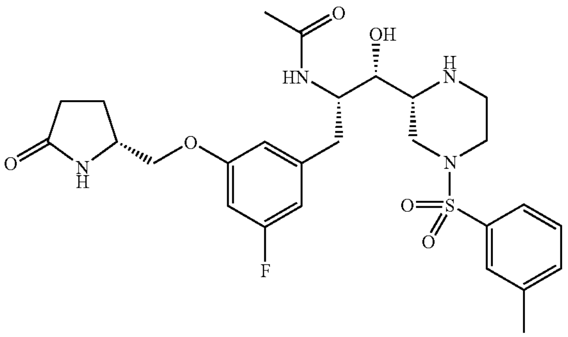 | 2.61 | 563 |

PREPARATIVE EXAMPLE 10

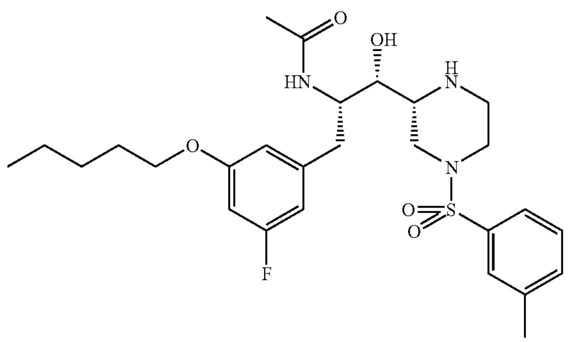

Step 1

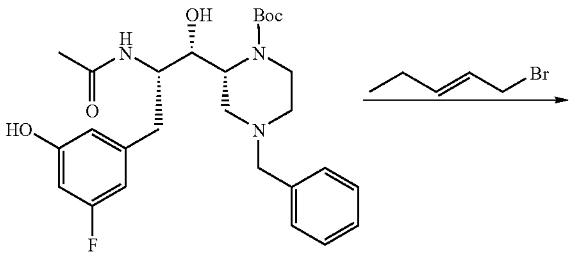

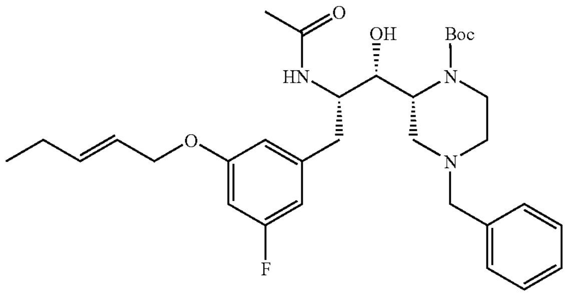

A mixture of the product of Preparative Example 9, Step 2 (50 mg, 0.10 mmol), 1-bromo-2-pentene (33 mg, 0.22 mmol), and potassium carbonate (138 mg, 0.100 mmol) in acetone (5 ml) was heated at 60° C. for 18 h. The mixture was filtered and concentrated to give the product (50 mg, 88%). MS m/e 570 $(M+H)^+$ Step 2

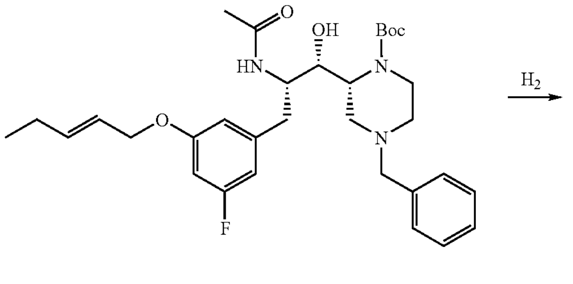

-continued

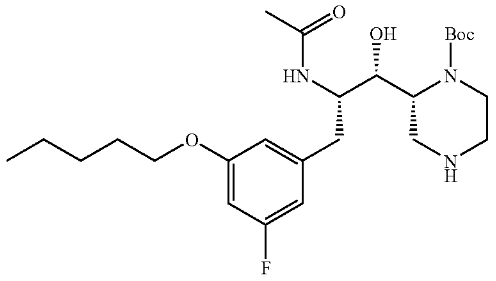

A mixture of the product of Step 1 (50 mg, 0.088 mmol), 20% $Pd(OH)_2/C$ (50 mg), and acetic acid (0.1 ml) in EtOH (5 ml) was stirred under $H_2$ (1 atm) for 16 h. The mixture was filtered and concentrated to give the product (35 mg, 83%). MS m/e 482 $(M+H)^+$ Step 3

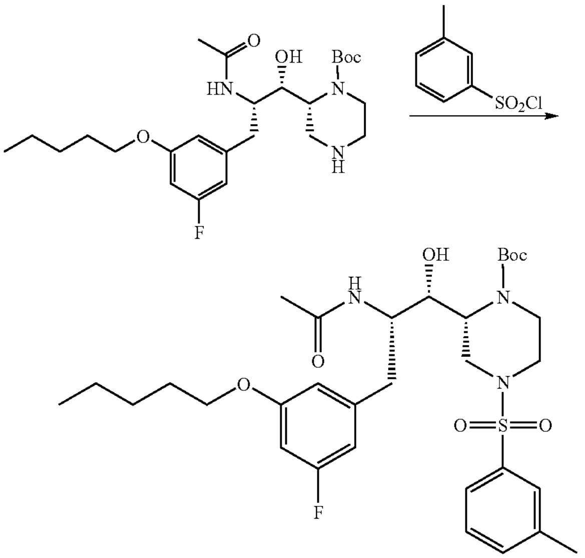

A mixture of the product of Step 2 (35 mg, 0.072 mmol), m-toluenesulfonyl chloride (14 mg, 0.072 mmol), and triethylamine (35 mg, 0.35 mmol) in $CH_2Cl_2$ (5 ml) was stirred in an ice-water bath for 30 min. The mixture was concentrated and purified by PTLC (5% $MeOH/CH_2Cl_2$) to give the product (30 mg, 66%). MS m/e 636 $(M+H)^+$ Step 4

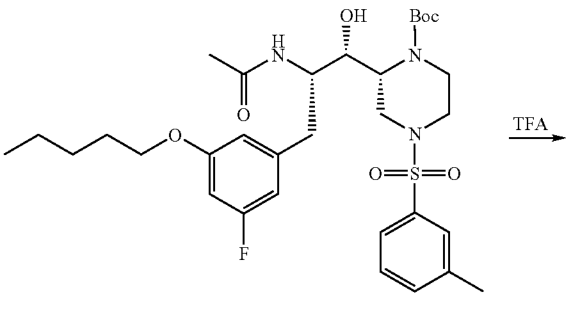

-continued

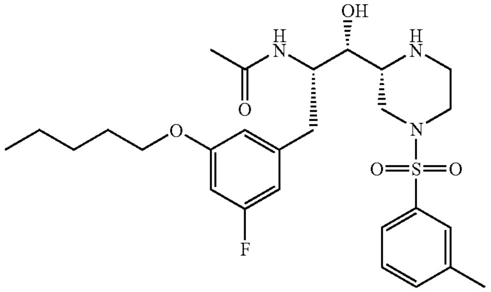

A solution of the product of Step 3 (30 mg, 0.047 mmol) and TFA (1 ml) in $CH_2Cl_2$ (5 ml) was stirred at RT for 1 h. The mixture was concentrated and purified by PTLC (5% 2M $NH_3$ in MeOH/95% $CH_2Cl_2$) to give the product (22 mg, 89%). $^1$H-NMR ($CDCl_3$): δ=7.50 (m, 2H), 7.36 (m, 2H), 6.43 (m, 3H), 5.93 (m, 1H), 4.15 (m, 1H), 3.84 (m, 2H), 3.65 (m, 2H), 3.39 (m, 1H), 3.02 (m, 1H), 2.83 (m, 4H), 2.39 (m, 5H), 1.85 (s, 3H), 1.70 (m, 2H), 1.33 (m, 4H), 0.88 (m, 3H). LCMS $t_R$=3.52 min m/e 536 (M+H)$^+$

PREPARATIVE EXAMPLE 11

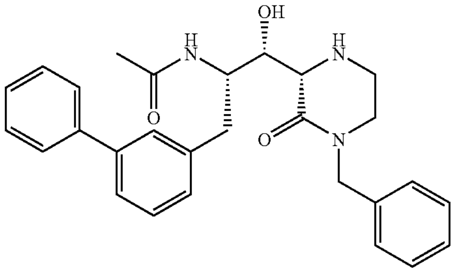

Step 1

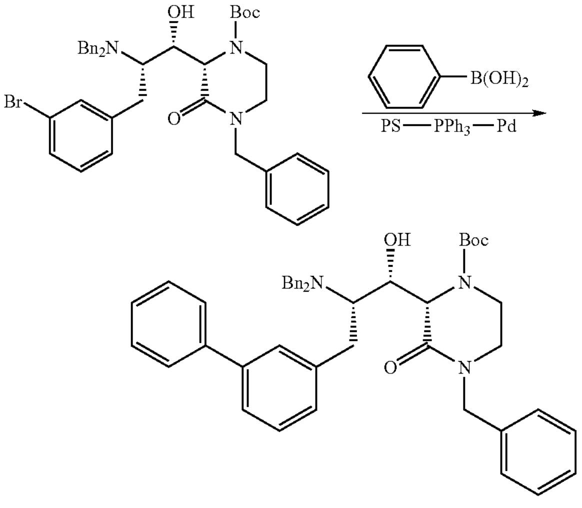

A mixture of the product of Preparative Example 1, Step 6 (142 mg, 0.203 mmol), phenylboronic acid (32 mg, 0.25 mmol), PS-$PPh_3$-Pd (160 mg, 0.016 mmol), and 1M aqueous potassium carbonate (0.25 ml) in EtOH (3 ml) was degassed, sealed, and heated at 100° C. in a microwave reactor for 15 min. The mixture was diluted with MeOH (40 ml), filtered, concentrated, and purified by PTLC (20% EtOAc/Hexanes) to give the product (96 mg, 68%). MS m/e 696 (M+H)$^+$ Step 2

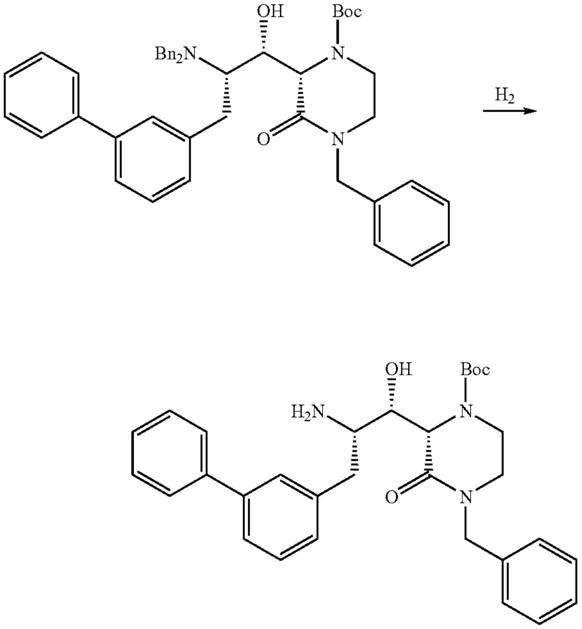

A mixture of the product of Step 1 (96 mg, 0.14 mmol), catalytic amount of acetic acid, and 20% $Pd(OH)_2$/C (150 mg) in MeOH (12 ml) was stirred under $H_2$ (1 atm) for 6 h. The mixture was filtered through a Celite pad and concentrated. The residue was partitioned between $CH_2Cl_2$ (40 ml) and $NH_4OH$ (15 ml). The organic layer was dried over $MgSO_4$ and concentrated to give the product (57 mg, 80%). MS m/e 516 (M+H)$^+$ Step 3

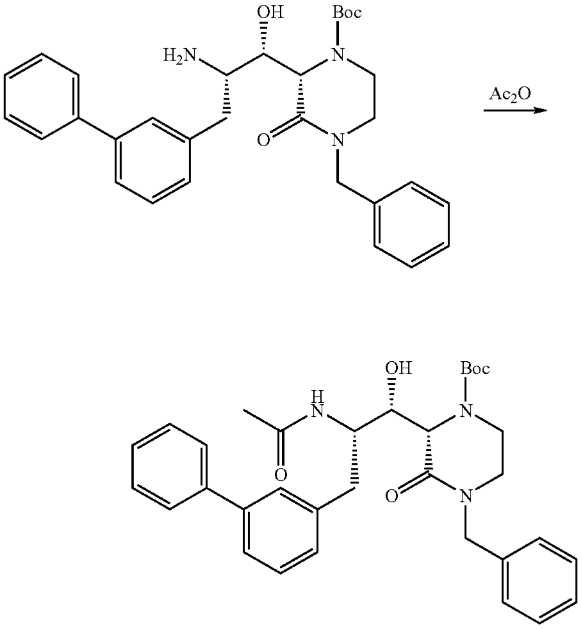

A mixture of the product of Step 2 (57 mg, 0.11 mmol), acetic anhydride (13 mg, 0.12 mmol), and triethylamine (20 μl, 0.14 mmol) in $CH_2Cl_2$ (10 ml) was stirred in an ice-water bath for 1 h then at RT for 3 h. The mixture was diluted with $CH_2Cl_2$ (40 ml) and extracted with 1N NaOH (15 ml). The organic layer was dried ($MgSO_4$), concentrated, and purified by PTLC (4% MeOH/$CH_2Cl_2$) to give the product (63 mg, 100%). MS m/e 558 $(M+H)^+$ Step 4

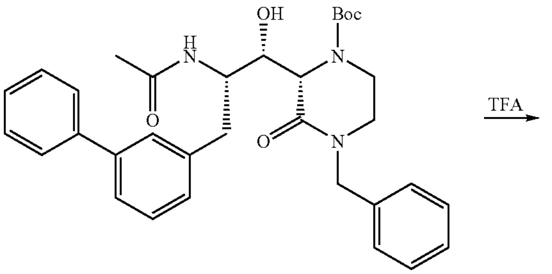

-continued

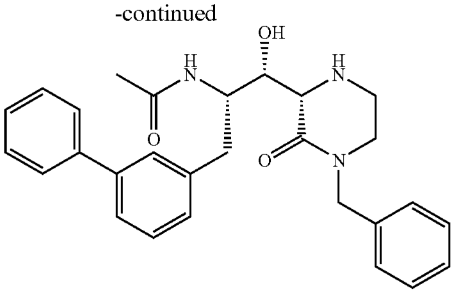

A solution of the product of Step 3 (63 mg, 0.11 mmol) and TFA (0.9 ml) in $CH_2Cl_2$ (4 ml) was stirred at RT for 3 h. The mixture was diluted with $CH_2Cl_2$ (40 ml) and extracted with $NH_4OH$ (15 ml). The organic layer was dried ($MgSO_4$), concentrated, and purified by PTLC (5% MeOH/$CH_2Cl_2$) to give the product (39 mg, 77%). $^1$H-NMR ($CDCl_3$): δ=7.1-7.6 (m, 14H), 6.28 (m, 1H), 4.69 (m, 1H), 4.48 (m, 1H), 4.30 (m, 1H), 4.05 (m, 1H), 3.39 (m, 1H), 3.24 (m, 1H), 2.8-3.2 (m, 4H), 2.67 (m, 1H), 1.80 (s, 3H). LCMS $t_R$=3.16 min m/e 458 $(M+H)^+$ By essentially the same procedure set forth in Preparative Example 11, the following examples were prepared.

| | LCMS $t_R$ (min) | $(M + H)^+$ |
|---|---|---|
| 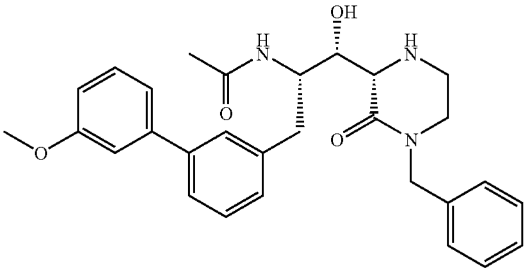 | 3.11 | 488 |
| 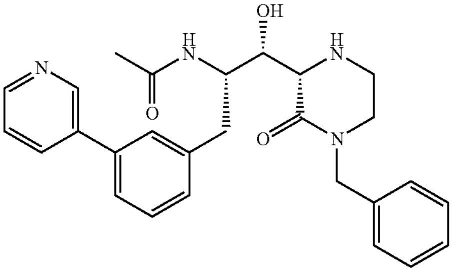 | 1.93 | 459 |
| 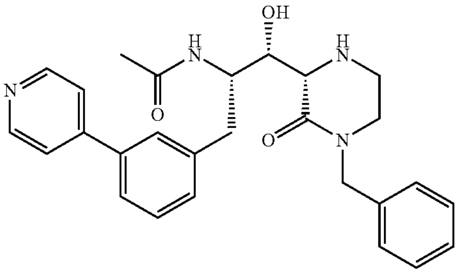 | 3.20 | 459 |

-continued

| | LCMS $t_R$ (min) | $(M + H)^+$ |
|---|---|---|
| 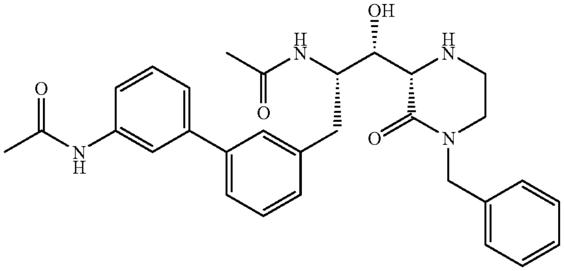 | 2.69 | 515 |
| 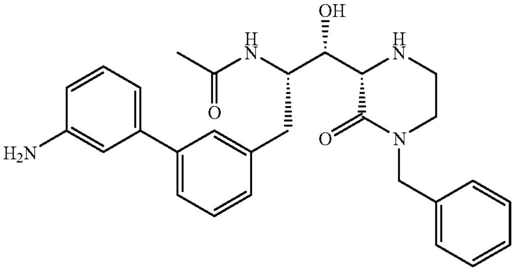 | 2.78 | 473 |
| 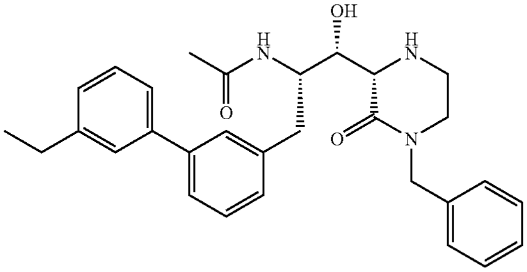 | 3.44 | 486 |

PREPARATIVE EXAMPLE 12

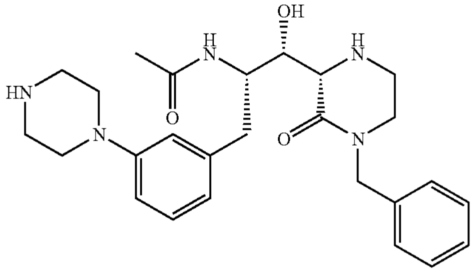

Step 1

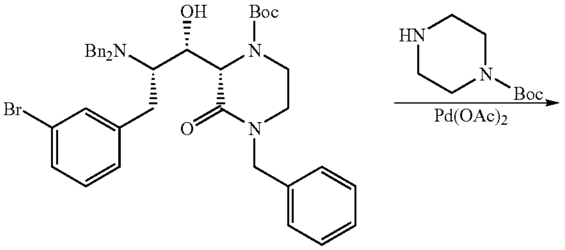

-continued

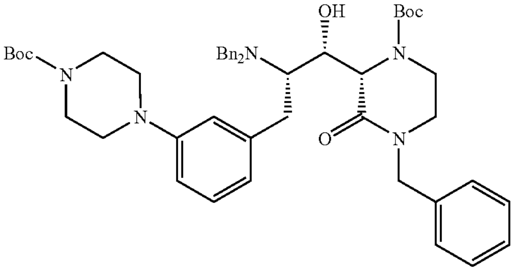

A mixture of the product of Preparative Example 1, Step 6 (191 mg, 0.273 mmol), N-t-butoxycarbonylpiperazine (78 mg, 0.42 mmol), cesium carbonate (345 mg, 1.06 mmol), BINAP (70 mg, 0.11 mmol), and palladium acetate (32 mg, 0.14 mmol) in dry toluene (8 ml) was heated at 95° C. for 16 h. The mixture was filtered, concentrated, and purified by PTLC (2% MeOH/$CH_2Cl_2$) to give the product (96 mg, 44%). MS m/e 804 $(M+H)^+$ Step 2

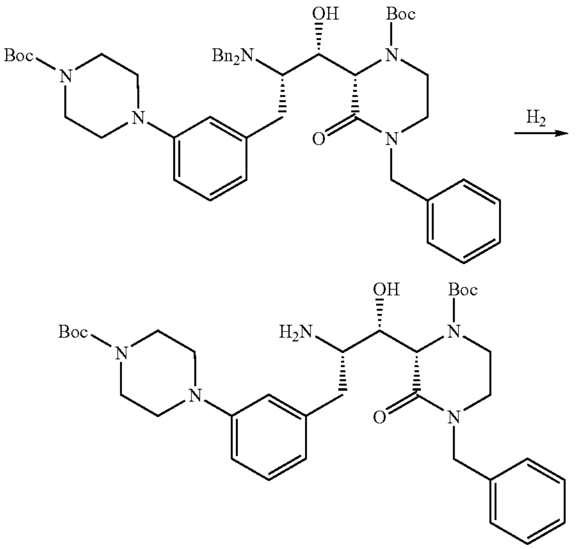

A mixture of the product of Step 1 (96 mg, 0.12 mmol), catalytic amount of acetic acid, and 20% $Pd(OH)_2/C$ (140 mg) in MeOH (10 ml) was stirred under $H_2$ (1 atm) for 4 h. The mixture was filtered and evaporated to dryness. The residue was dissolved in $CH_2Cl_2$ (40 ml) and extracted with $NH_4OH$ (10 ml). The organic layer was dried ($MgSO_4$) and concentrated to give the product (56 mg, 74%). MS m/e 624 $(M+H)^+$ Step 3

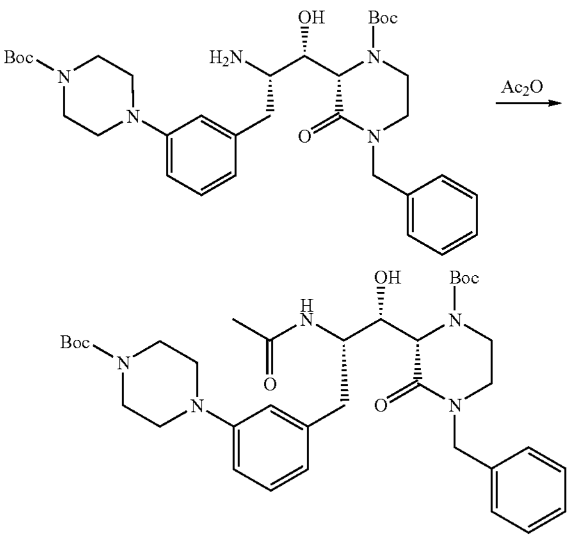

A mixture of the product of Step 2 (56 mg, 0.089 mmol), acetic anhydride (9.5 mg, 0.093 mmol), and triethylamine (25 μl, 0.18 mmol) in $CH_2Cl_2$ (10 ml) was stirred in an ice-water bath for 1 h then at RT for 16 h. The mixture was concentrated and purified by PTLC (3% $MeOH/CH_2Cl_2$) to give the product (51 mg, 86%). MS m/e 666 $(M+H)^+$ Step 4

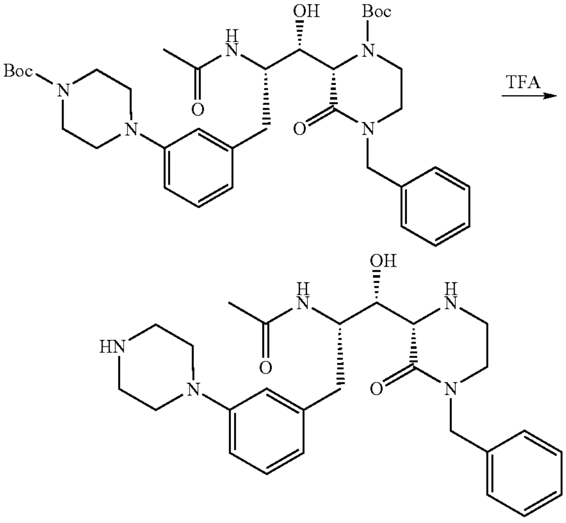

A solution of the product of Step 3 (51 mg, 0.077 mmol) and TFA (1 ml) in $CH_2Cl_2$ (5 ml) was stirred at RT for 4 h. The mixture was diluted with $CH_2Cl_2$ (40 ml) and extracted with $NH_4OH$ (15 ml). The organic layer was dried ($MgSO_4$), concentrated, and purified by PTLC (15% $MeOH/CH_2Cl_2$) to give the product (24 mg, 68%). $^1H$-NMR ($CDCl_3$): δ=7.1-7.3 (m, 6H), 6.85 (s, 1H), 6.72 (m, 2H), 6.18 (m, 1H), 4.67 (m, 1H), 4.42 (m, 1H), 4.31 (m, 1H), 4.00 (m, 1H), 3.36 (m, 1H), 3.23 (m, 1H), 2.6-3.1 (m, 14H), 1.82 (s, 3H). LCMS $t_R$=2.16 min m/e 466 $(M+H)^+$

BACE-1 Cloning, Protein Expression and Purification

A predicted soluble form of human BACE1 (sBACE1, corresponding to amino acids 1-454) was generated from the full length BACE1 cDNA (full length human BACE1 cDNA in pcDNA4/mycHisA construct; University of Toronto) by PCR using the advantage-GC cDNA PCR kit (Clontech, Palo Alto, Calif.). A HindIII/PmeI fragment from pcDNA4-sBACE1 myc/His was blunt ended using Klenow and subcloned into the Stu I site of pFASTBACI(A) (Invitrogen). A sBACE1mycHis recombinant bacmid was generated by transposition in DH10Bac cells (GIBCO/BRL). Subsequently, the sBACE1mycHis bacmid construct was transfected into sf9 cells using Cell Fectin (Invitrogen, San Diego, Calif.) in order to generate recombinant baculovirus. Sf9 cells were grown in SF 900-II medium (Invitrogen) supplemented with 3% heat inactivated FBS and 0.5× penicillin/streptomycin solution (Invitrogen). Five milliliters of high titer plaque purified sBACEmyc/His virus was used to infect 1 L of logarithmically growing sf9 cells for 72 hours. Intact cells were pelleted by centrifugation at 3000×g for 15 minutes. The supernatant, containing secreted sBACE1, was collected and diluted 50% v/v with 100 mM HEPES, pH 8.0. The diluted medium was loaded onto a Q-sepharose column. The Q-sepharose column was washed with Buffer A (20 mM HEPES, pH 8.0, 50 mM NaCl).

Proteins, were eluted from the Q-sepharose column with Buffer B (20 mM HEPES, pH 8.0, 500 mM NaCl). The protein peaks from the Q-sepharose column were pooled and loaded onto a Ni-NTA agarose column. The Ni-NTA column was then washed with Buffer C (20 mM HEPES, pH 8.0, 500 mM NaCl). Bound proteins were then eluted with Buffer D (Buffer C+250 mM imidazole). Peak protein fractions as determined by the Bradford Assay (Biorad, CA) were concentrated using a Centricon 30 concentrator (Millipore). sBACE1 purity was estimated to be ~90% as assessed by SDS-PAGE and Commassie Blue staining. N-terminal sequencing indicated that greater than 90% of the purified sBACE1 contained the prodomain; hence this protein is referred to as sproBACE1.

Peptide Hydrolysis Assay

The inhibitor, 25 nM EuK-biotin labeled APPsw substrate (EuK-KTEEISEVNLDAEFRHDKC-biotin; CIS-Bio International, France), 5 μM unlabeled APPsw peptide (KTEEISEVNLDAEFRHDK; American Peptide Company, Sunnyvale, Calif.), 7 nM sproBACE1, 20 mM PIPES pH 5.0, 0.1% Brij-35 (protein grade, Calbiochem, San Diego, Calif.), and 10% glycerol were preincubated for 30 min at 30° C. Reactions were initiated by addition of substrate in a 5 μl aliquot resulting in a total volume of 25 μl. After 3 hr at 30° C. reactions were terminated by addition of an equal volume of 2× stop buffer containing 50 mM Tris-HCl pH 8.0, 0.5 M KF, 0.001% Brij-35, 20 μg/ml SA-XL665 (cross-linked allophycocyanin protein coupled to streptavidin; CIS-Bio International, France) (0.5 μg/well). Plates were shaken briefly and spun at 1200×g for 10 seconds to pellet all liquid to the bottom of the plate before the incubation. HTRF measurements were made on a Packard Discovery® HTRF plate reader using 337 nm laser light to excite the sample followed by a 50 μs delay and simultaneous measurements of both 620 nm and 665 nm emissions for 400 μs.

$IC_{50}$ determinations for inhibitors, (I), were determined by measuring the percent change of the relative fluorescence at 665 nm divided by the relative fluorescence at 620 nm, (665/620 ratio), in the presence of varying concentrations of I and a fixed concentration of enzyme and substrate. Nonlinear regression analysis of this data was performed using GraphPad Prism 3.0 software selecting four parameter logistic equation, that allows for a variable slope. Y=Bottom+(Top-Bottom)/(1+10^(LogEC50-X)*Hill Slope)); X is the logarithm of concentration of 1, Y is the percent change in ratio and Y starts at bottom and goes to top with a sigmoid shape.

Compounds of the present invention have an $IC_{50}$ range from about 100 to about 10,000 nM, preferably about 100 to about 1000 nM, more preferably about 100 to about 500 nM. Compounds of the preferred stereochemistry have $IC_{50}$ values in a range of about 2 to about 500 nM, preferably about 2 to about 100 nM.

The compound of the following formula

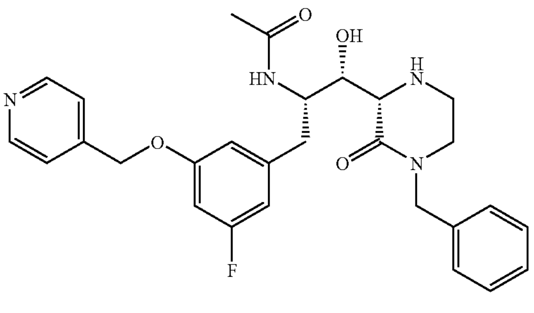

has a $IC_{50}$ of 186 nM.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A compound having the structural formula (I)

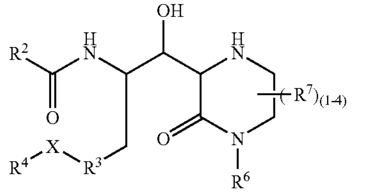

or a pharmaceutically acceptable salt thereof, wherein $R^2$ is hydrogen or alkyl;

$R^3$ is phenylene;

$R^4$ is —C(O)-alkyl, —C(O)Oethyl, alkyl, cycloalkyl, cycloalkylalkyl, aryl, aralkyl, alkoxyalkyl, heterocyclyl, heterocyclylalkyl, heteroaralkyl or heteroaryl;

$R^6$ is

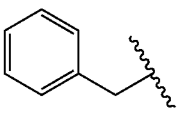

or

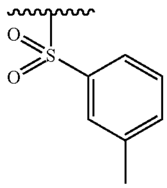

;

each $R^7$ is independently selected from hydrogen, —OH, alkyl, cycloalkyl, aryl, heteroaryl, aralkyl, heteroaralkyl, aralkoxy, heteroaralkoxy and alkoxy; and X is a bond connecting $R^3$ and $R^4$, or, alternatively, X is —O—, —S—, alkylene, -alkyleneNH—, -alkyleneNHC(O)—, -alkyleneNHSO$_2$—, —NH—, —NHC(O)—, or —NHSO$_2$—;

wherein each alkyl is optionally substituted with 1 to 3 moieties selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl; and wherein each phenylene, heterocyclylalkyl, cycloalkyl, cycloalkylalkyl, aryl, heteroaryl, heterocyclyl, aralkyl, heteroaralkyl, aralkoxy or heteroaralkoxy is optionally substituted with 1 to 4 moieties selected from the group consisting of —$CF_3$, alkyl, alkenyl, alkynyl, aryl, heteroaryl, aralkyl, alkylaryl, heteroaralkyl, arylalkenyl, heteroarylalkenyl, arylalkynyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—$NH_2$, —C(=NH)—$NH_2$, —C(=NH)—NH(alkyl), $Y_1Y_2N$—, $Y_1Y_2NC(O)$—, $Y_1Y_2NSO_2$— and —$SO_2NY_1Y_2$, wherein $Y_1$ and $Y_2$ can be the same or different and are independently selected from the group consisting of hydrogen, alkyl, aryl, cycloalkyl, —C(O)

alkyl and aralkyl, with the proviso that cycloalkyl, cycloalkylene, heterocyclyl and heterocyclylene can be substituted with =O, wherein:

"heteroaryl" means a moiety selected from pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxatinyl, phthalazinyl, imidazo[1,2-a] pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, and benzothiazolyl; and "heterocyclyl" (or "heterocycloalkyl") means a moiety selected from piperidyl, pyrrolidinyl, pyrazolidinyl, imidazolinyl, piperazinyl, morpholinyl, thiomorpholinyl, dithianyl, trithianyl, thiazolidinyl, 1,3-dioxolanyl, 1,4-dioxanyl, tetrahydrofuranyl, tetrahydrothiophenyl, and tetrahydrothiopyranyl.

2. The compound of claim 1 wherein $R^2$ is alkyl.

3. The compound of claim 2 wherein $R^2$ methyl.

4. The compound of claim 1 wherein $R^3$ is fluoro substituted phenylene.

5. The compound of claim 1 wherein $R^4$ is —C(O)-alkyl, alkyl, aryl, aralkyl, substituted aryl, substituted aralkyl, alkoxyalkyl, heteroaralkyl, substituted heteroaryl, substituted heteroaralkyl, alkoxyalkyl, heterocyclyl, heterocycylalkyl, substituted heterocyclyl, substituted heterocyclylalkyl or heteroaryl.

6. The compound of claim 5 wherein $R^4$ is methyl, ethyl, propyl, butyl, pentyl, hexyl, —C(O)Oethyl,

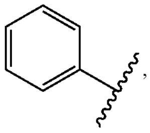,
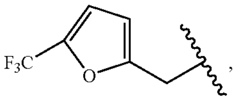,
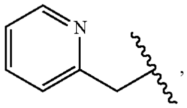,
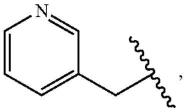,
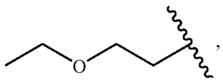,
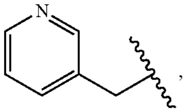,
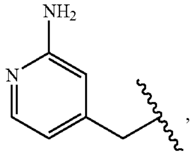,
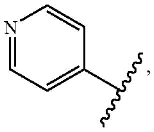,
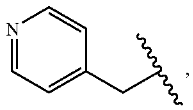,
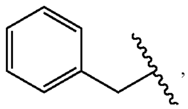,
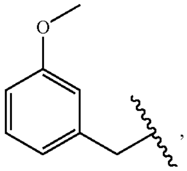,
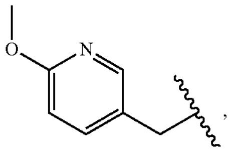, -continued

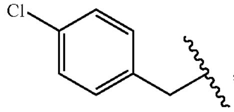,
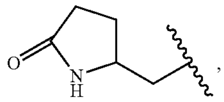,
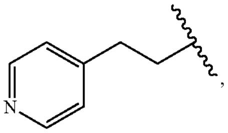,
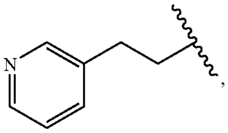,
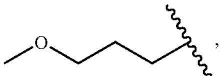,
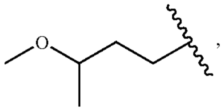,
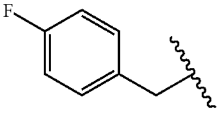,
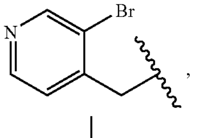,
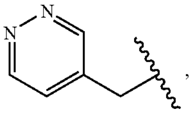,
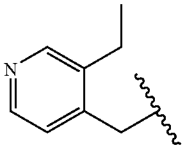,
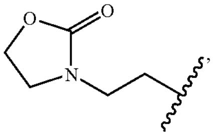,
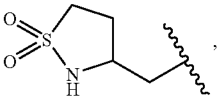,
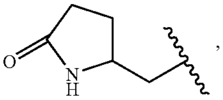,
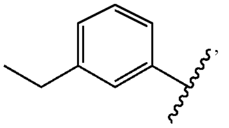,
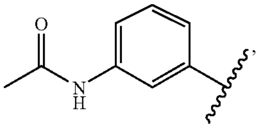,
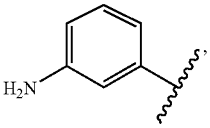,
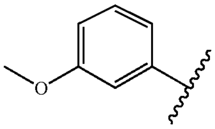
or
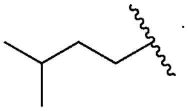.

7. The compound of claim 1 wherein each $R^7$ is independently selected from hydrogen, alkyl substituted by a cycloalkyl group, alkyl substituted by an aryl and heteroaryl group.

8. The compound of claim 1 wherein X is a bond connecting $R^3$ and $R^4$, or, alternatively, X is O, alkylene, -alkylene-$NHSO_2$— or -alkylene-NHC(O)—.

9. The compound of claim 1 wherein $R^2$ is alkyl;

$R^3$ is phenylene or halo-substituted phenylene;

$R^4$ is —C(O)-alkyl, alkyl, aryl, aralkyl, substituted aryl, substituted aralkyl, alkoxyalkyl, heteroaralkyl, substituted heteroaryl, substituted heteroaralkyl, alkoxyalkyl, heterocyclyl, heterocyclylalkyl, substituted heterocyclyl, substituted heterocyclylalkyl or heteroaryl;

each $R^7$ is independently selected from hydrogen, alkyl substituted by a cycloalkyl group, alkyl substituted by an aryl and heteroaryl group;

$R^8$ is

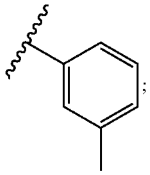;

and

X is a bond connecting $R^3$ and $R^4$, or, alternatively, X is O, alkylene, -alkylene-$NHSO_2$— or -alkylene-NHC(O)—.

10. The compound of claim 9 wherein $R^2$ is methyl.

11. The compound of claim 9 wherein $R^3$ is

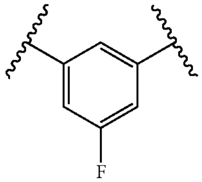

or

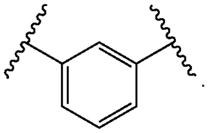.

12. The compound of claim 9 wherein $R^4$ is methyl, ethyl, propyl, butyl, pentyl, hexyl, —C(O)Oethyl,

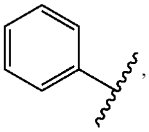,

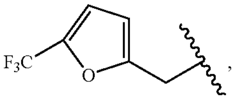,

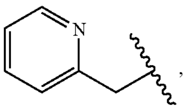,

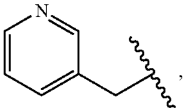,

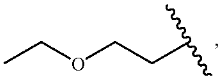,

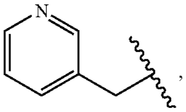,

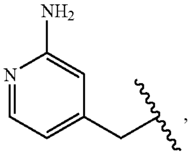,

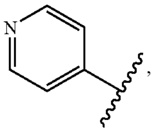,

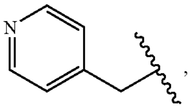,

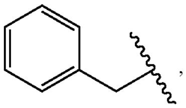,

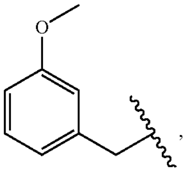,

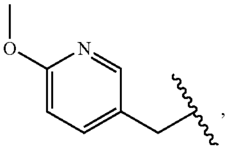,

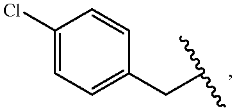,

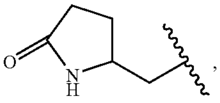,

-continued

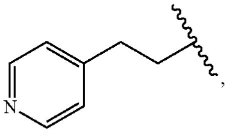,

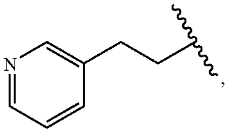,

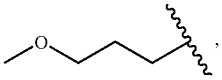,

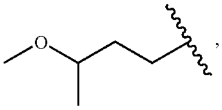,

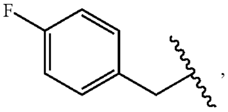,

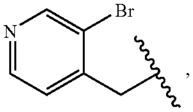,

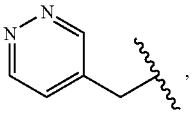,

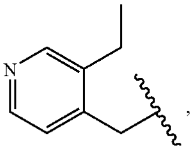,

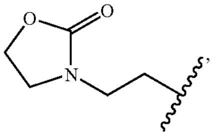,

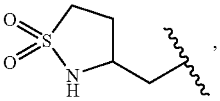,

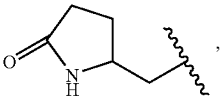,

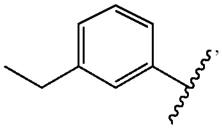,

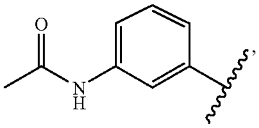,

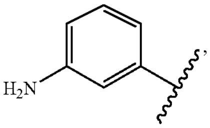

or

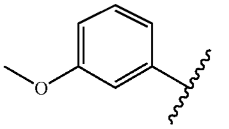.

13. The compound of claim 9 wherein $R^6$ is

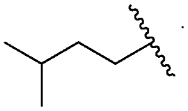.

14. The compound of claim 9 wherein $R^7$ is hydrogen.

15. The compound of claim 9 wherein X is a bond connecting $R^3$ and $R^4$, or, alternatively, X is O, alkylene, -alkylene-$NHSO_2$— or -alkylene-NHC(O)—.

16. A compound of claim 1 having the stereochemical structure:
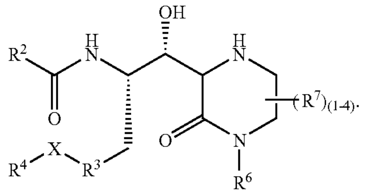
17. A compound, or a pharmaceutically acceptable salt thereof, said compound selected from the group consisting of
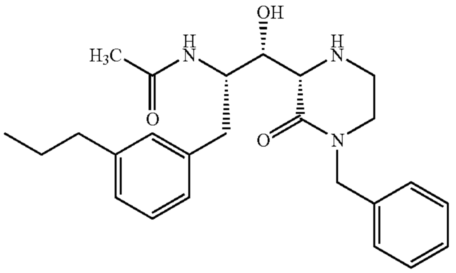
,
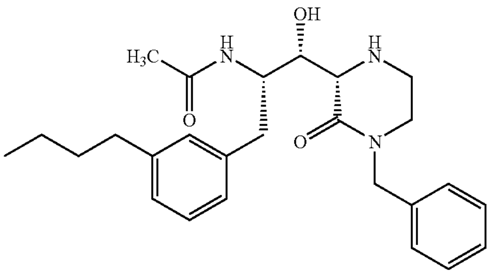
,
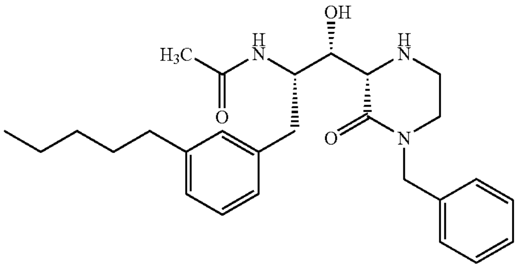
,
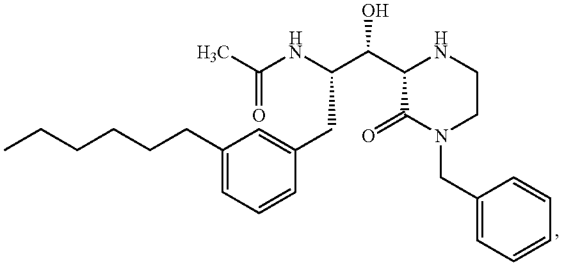
,
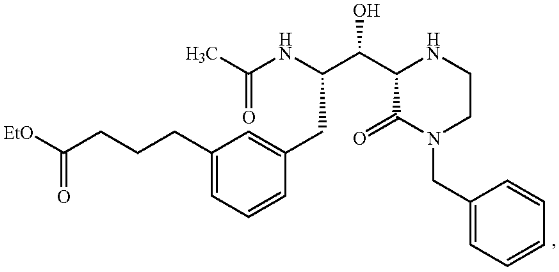
,
-continued
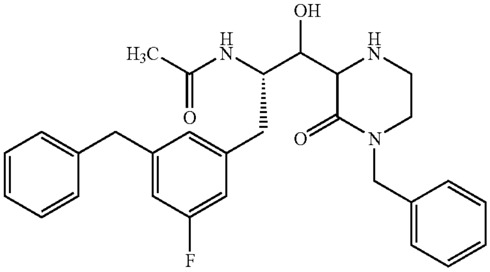
,
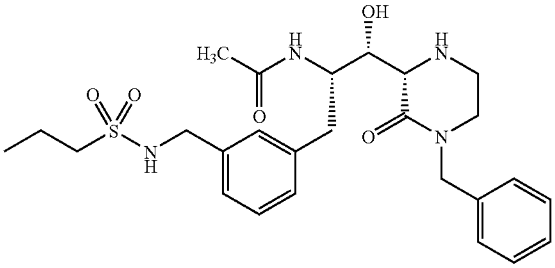
,
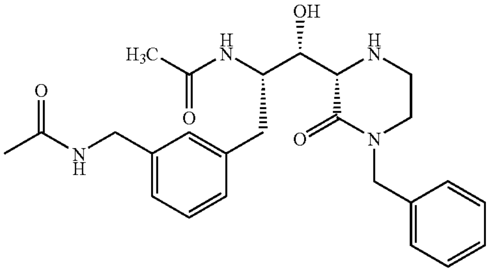
,
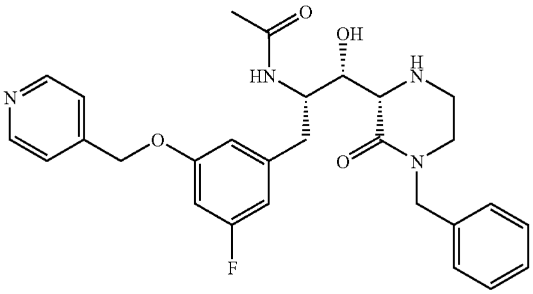
,
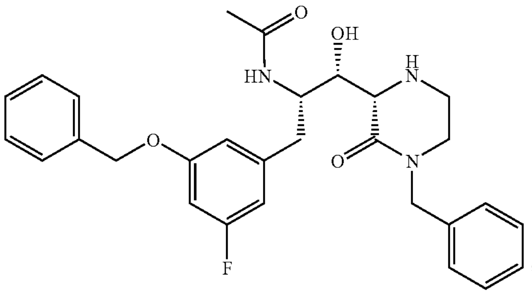
,
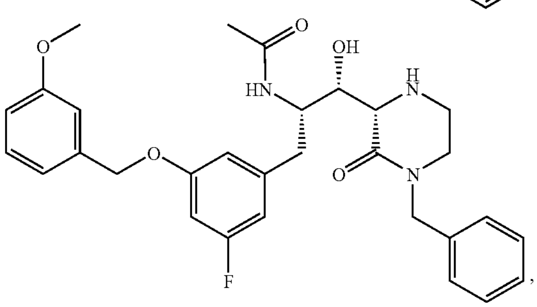
, -continued
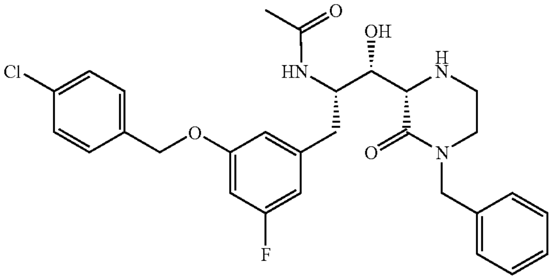
,
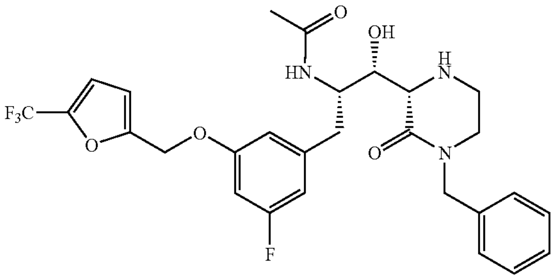
,
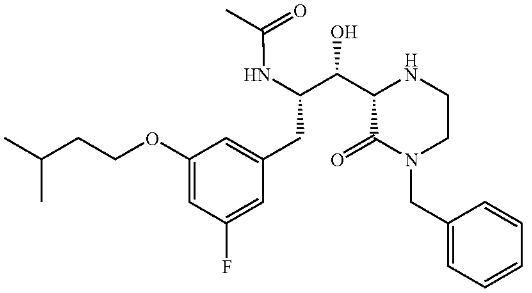
,
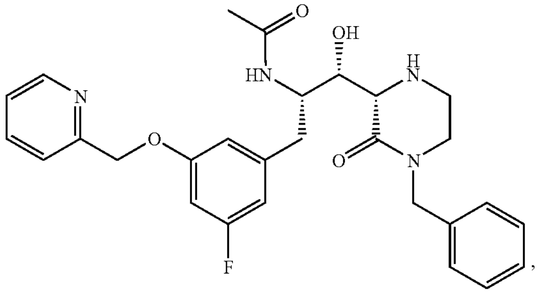
,
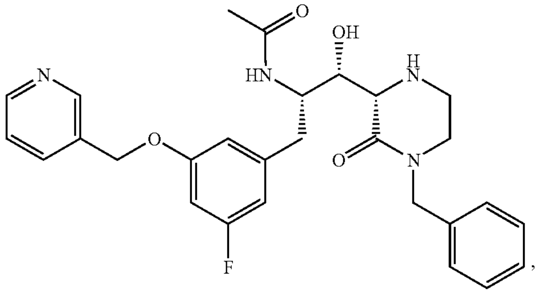
,
-continued
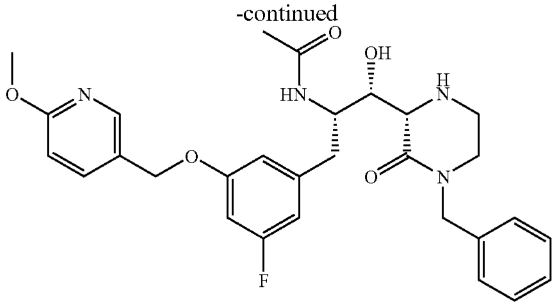
,
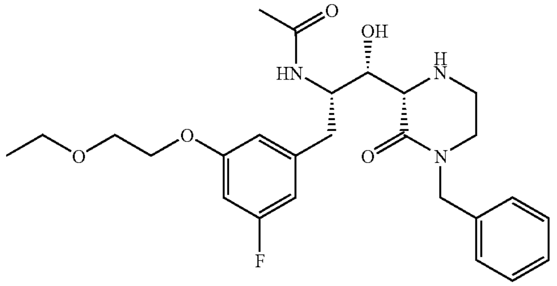
,
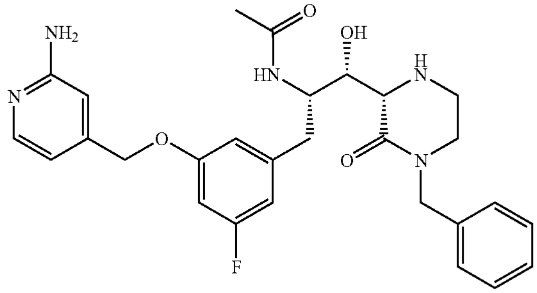
,
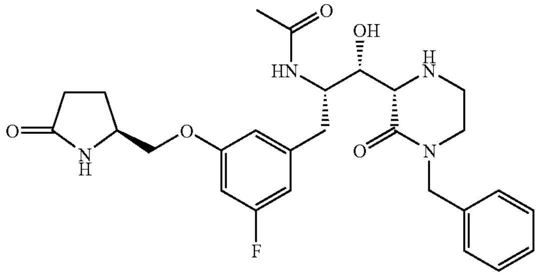
,
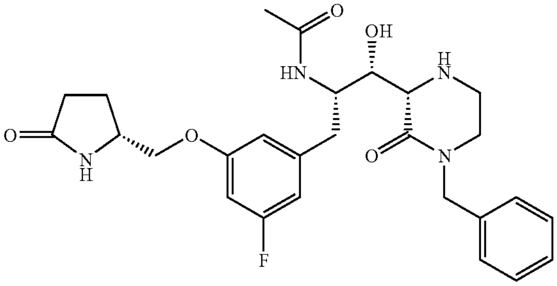
,
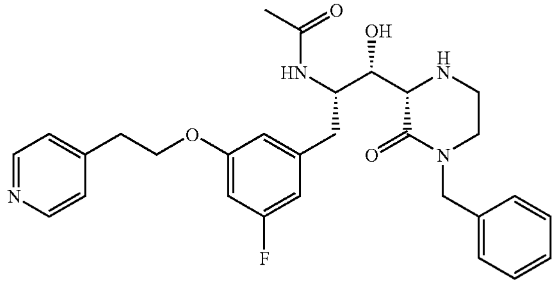
, -continued
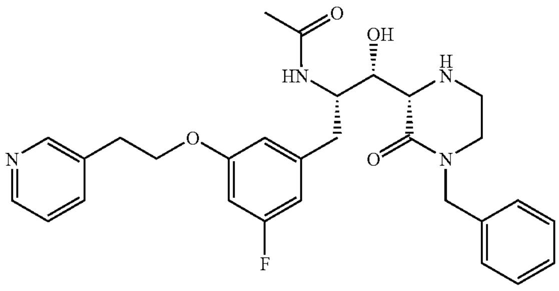
,
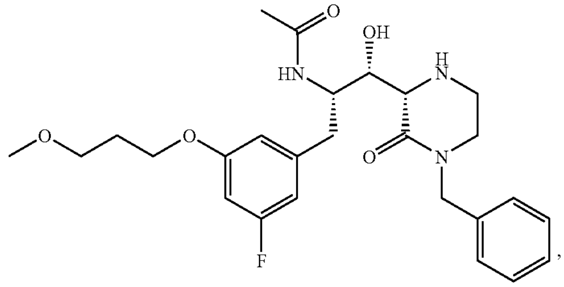
,
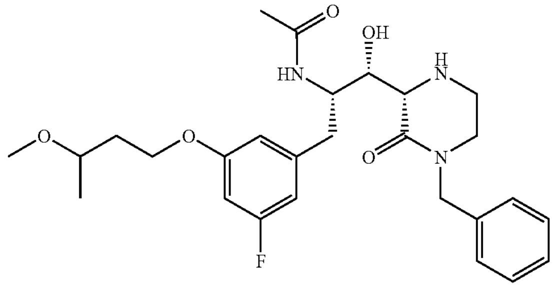
,
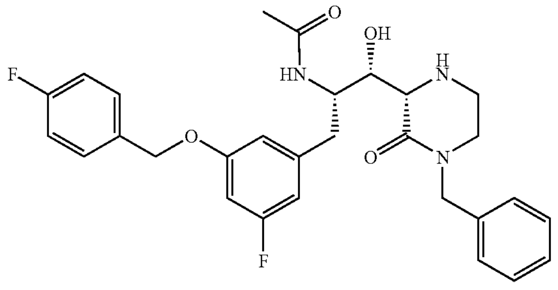
,
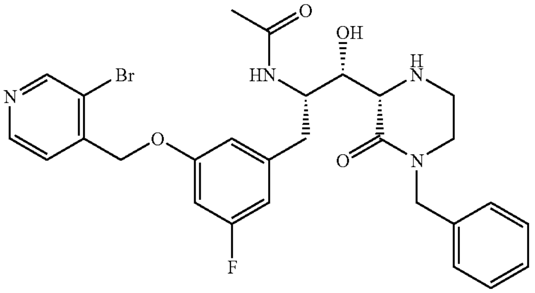
,
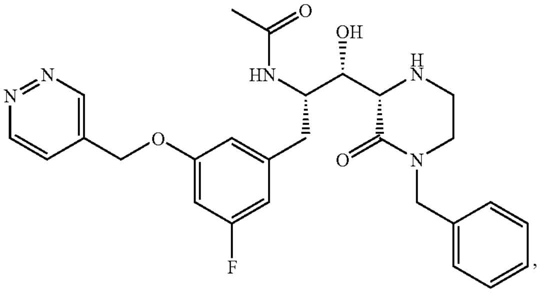
,
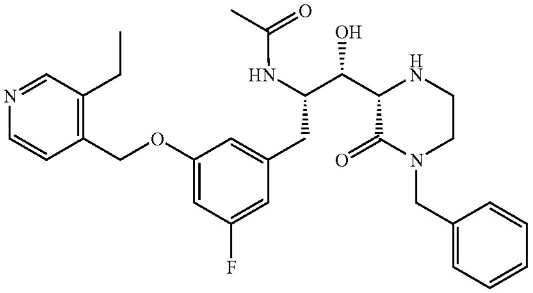
,
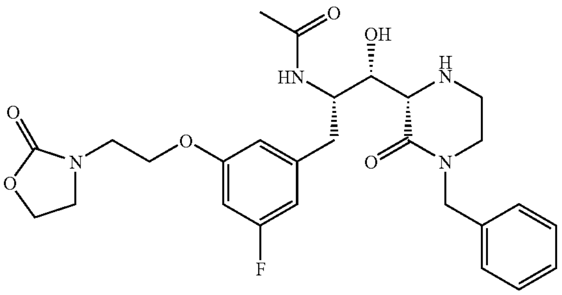
,
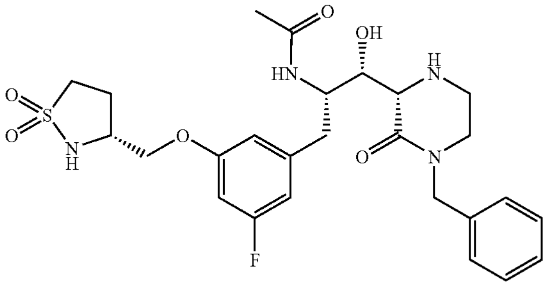
,
-continued
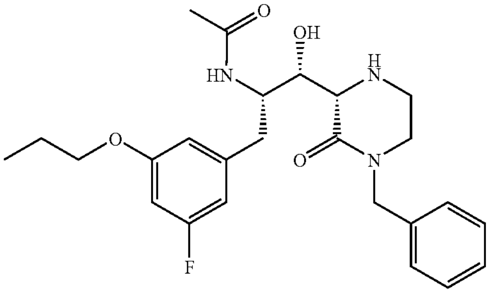
, -continued
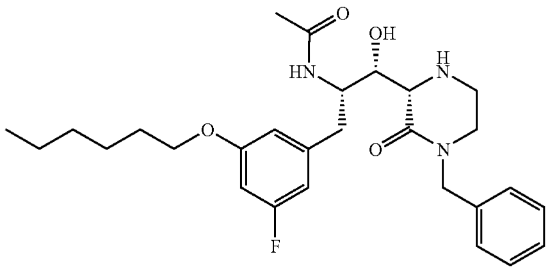
,
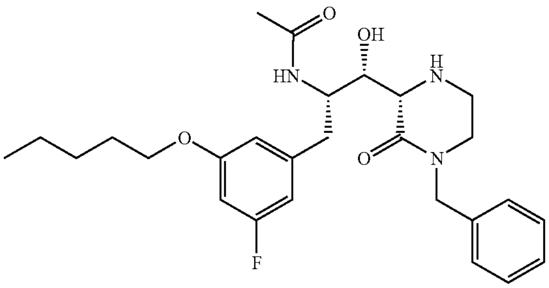
,
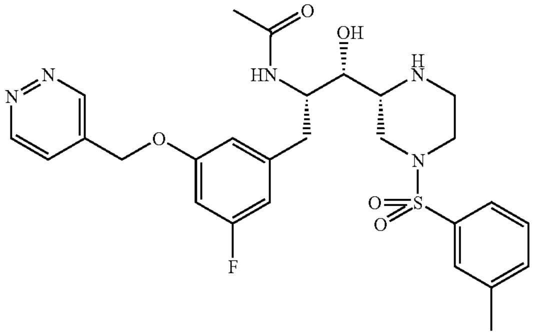
,
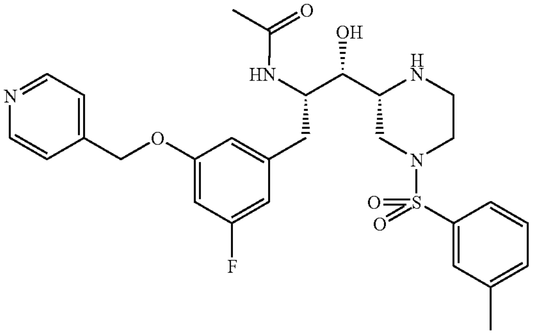
,
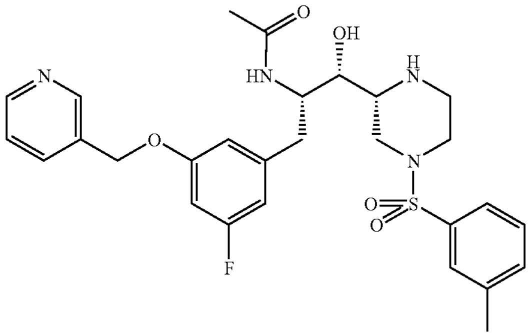
,
-continued
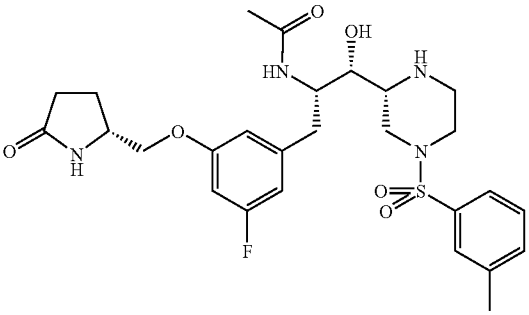
,
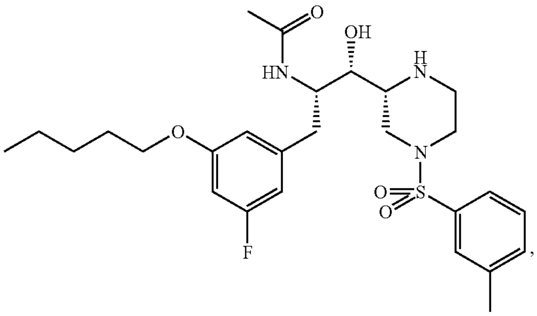
,
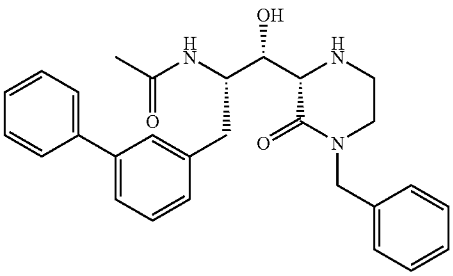
,
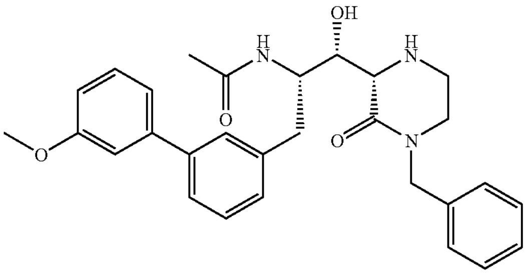
,
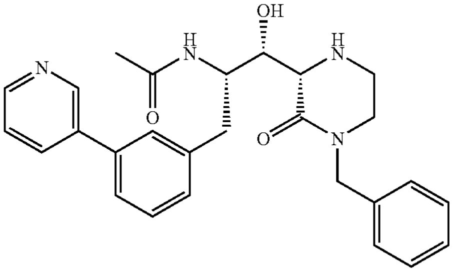
, -continued
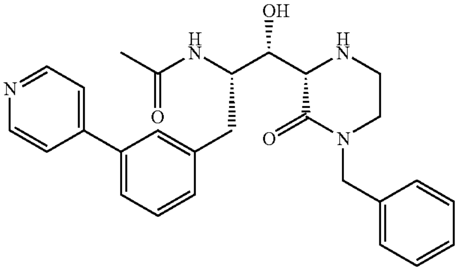
,
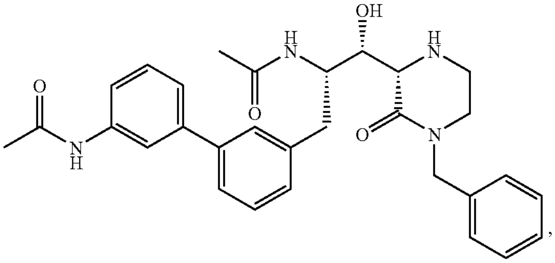
,
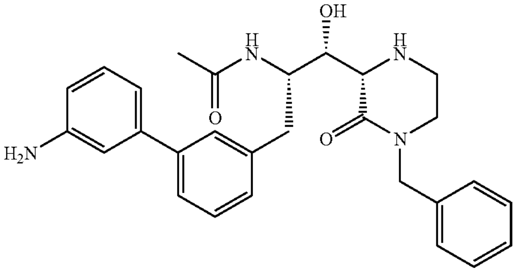
,
-continued
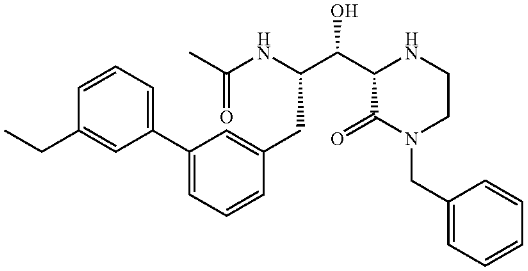
,
and
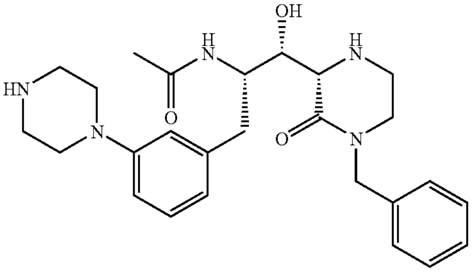
.
18. A pharmaceutical composition comprising a compound of claim 1 and a pharmaceutically effective carrier.
19. A compound of claim 1 in isolated or purified form.
* * * * *